United States Patent
Strobel et al.

(10) Patent No.: US 6,949,556 B2
(45) Date of Patent: Sep. 27, 2005

(54) ACYLATED 1,2,3,4-TETRAHYDRONAPHTHYL AMINES AND THEIR USE AS PHARMACEUTICAL AGENTS

(75) Inventors: Hartmut Strobel, Liederbach (DE); Paulus Wohlfart, Bensheim (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 10/073,307

(22) Filed: Feb. 13, 2002

(65) Prior Publication Data

US 2003/0022935 A1 Jan. 30, 2003

(30) Foreign Application Priority Data

Feb. 13, 2001 (EP) .............................. 01102851

(51) Int. Cl.[7] ..................... C07D 213/56; A61K 31/435
(52) U.S. Cl. .................. 514/255.06; 514/301; 514/344; 514/352; 514/359; 514/365; 514/336; 514/379; 514/350; 514/354; 514/394; 514/403; 544/406; 544/407; 546/114; 546/280.4; 546/298; 546/310; 546/323; 548/200; 548/241; 548/261; 548/309; 548/374.1; 548/503
(58) Field of Search ................................ 544/406, 407; 546/114, 298, 280.4, 310, 323; 548/200, 241, 261, 309, 374.1, 503; 514/255.06, 301, 344, 352, 359, 365, 336, 379, 403, 354, 350, 394

(56) References Cited

U.S. PATENT DOCUMENTS 4,192,888 A    3/1980   Bondinell et al. .......... 424/321

FOREIGN PATENT DOCUMENTS

| EP | 0253357 | 1/1988 |
|----|---------|--------|
| EP | 0420064 | 4/1991 |
| EP | 0 467 614 A1 | 1/1992 |
| WO | WO 96/01817 | 1/1996 |
| WO | WO 97/04775 | * 2/1997 |
| WO | WO 97/04779 | 2/1997 |
| WO | WO 99/47153 | 9/1999 |
| WO | WO 00/03746 | 1/2000 |
| WO | WO 00/51970 | 9/2000 |
| WO | WO 01/85675 A2 | 11/2001 |
| WO | WO 02/20530 A1 | 3/2002 |

OTHER PUBLICATIONS

Albrecht et al., Chem. Abstract 77:88182, 1972.*
Cannon et al., Centrally Acting Emetics. 6. Derivatives of β–Naphthylamine and 2–Indanamine, Journal of Medicinal Chemistry, 1972, vol. 15, No. 4, 348–350.
Cannon et al., Rigid Amino Acids Related to α–Methyldopa, Journal of Medicinal Chemistry, 1974, vol. 17, No. 5, 565–568.

Cannon et al., Conformationally Restricted Congeners of Dopamine Derived from 2–Aminoindan, Journal of Medicinal Chemistry, 1982, 25, 1442–1446.
Colette, et al., Étude Des Nitrosochlorures De L'Indéne Et De Ses Homologues, Ann. Chim. 1976, p. 269–276.
Copinga et al., 2–Amido–8–methoxytetralins: A Series of Nonindolic Melatonin–like Agents, J. Med. Chem. 1993, 36, 2891–2898.
Peter A. Crooks, A new synthesis of 2–aminoindanes, Chemistry and Industry, Jun. 15, 1974, 495.
Devocelle et al., Alternative synthesis of the chiral atypical β–adrenergic phenylethanolaminotetraline agonist SR58611A using enantioselective hydrogenation, Tetrahedron Letters 40 (1999) 4551–4554.
Endres et al., Stroke protection by 3–hydroxy–3–methylglutaryl (HMG)–CoA reductase inhibitors mediated by endothelial nitric oxide synthase, Proc. Natl. Acad. Sci. USA, vol. 95, 8880–8885, Jul. 1998.

(Continued)

*Primary Examiner*—Deepak Rao
(74) *Attorney, Agent, or Firm*—Julie Anne Knight; Raymond S. Parker, III

(57) ABSTRACT

The present invention relates to compounds of general formula (I),

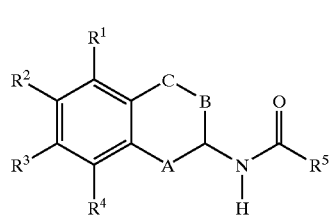

wherein $R^1$–$R^4$ have the meanings given in the specification, A is $CH_2$, CHOH or CH—($C_1$–$C_3$-alkyl), B and C are independently $CH_2$ or CH—($C_1$–$C_3$-alkyl), and $R^5$ is an aryl or heteroaryl group optionally substituted by the substituents listed in the specification. The compounds are useful for the manufacture of medicaments for the treatment of cardiovascular diseases, stable or unstable angina pectoris, coronary heart disease, Prinzmetal angina, acute coronary syndrome, heart failure, myocardial infarction, stroke, thrombosis, peripheral artery occlusive disease, endothelial dysfunction, atherosclerosis, restenosis, endothelial damage after PTCA, hypertension, essential hypertension, pulmonary hypertension, secondary hypertension, renovascular hypertension, chronic glomerulonephritis, erectile dysfunction, ventricular arrhythmia, diabetes or diabetes complications, nephropathy or retinopathy, angiogenesis, asthma bronchiale, chronic renal failure, cirrhosis of the liver, osteoporosis, and restricted memory performance or a restricted ability to learn, or the lowering of cardiovascular risk of postmenopausal women or after intake of contraceptives.

42 Claims, No Drawings

OTHER PUBLICATIONS

Hillver et al., (S)–5–Fluoro–8–hydroxy–2–(dipropyl-amino)tetralin: A Putative 5–HT$_{1A}$–Receptor Antagonist, J. Med. Chem., 1990, 33, 1541–1544.

Itoh et al., The Syntheses and β–Adrenoceptor Activities of N–Substituted 2–Amino–5,6–dihydroxy–1,2,3,4–tetrahydro–1–naphthalenols, Chem. Pharm. Bull. 25(11) 2917–2928 (1977).

Li et al., Activation of Protein Kinase Cα and/or ε Enhances Transcription of the Human Endothelial Nitric Oxide Synthase Gene, Molecular Pharmacology, 53:630–637 (1998).

Malapel–Andrieu et al., Palladium–Catalyzed Reactions of Indolic Triflate with Allylic Alcohols, Tetrahedron Letters 39 (1998) 39–42.

Masui et al., Stereoselective Synthesis of 1,2–Amino Alcohols by Asymmetric Borane Reduction of α–Oxoketoxime Ethers, Tetrahedron Letters 39 (1998) 5195–5198.

Moroi, et al., Interaction of Genetic Deficiency of Endothelial Nitric Oxide, Gender, and Pregnancy in Vascular Response to Injury in Mice, The Journal of Clinical Investigation, vol. 101, No. 6, Mar. 1998, 1225–1232.

Nakayama, et al., T$^{-786}$→C Mutation in the 5' –Flanking Region of the Endothelial Nitric Oxide Synthase Gene Is Associated With Coronary Spasm, Clinical Investigation and Reports, 2864–2870 (1999).

Sessa et al., Chronic Exercise in Dogs Increases Coronary Vascular Nitric Oxide Production and Endothelial Cell Nitril Oxide Synthase Gene Expression, Circulation Research, 74(2):349–353, 1994.

Trillat et al., (–)–5–Methyl–8–hydroxy–(di–n–propyl-amino)tetralin: A new 5–HT$_{1A}$ receptor antagonist, Eur. J. Med. Chem. 33 (1998) 437–444.

Tschaen et al., Asymmetric Synthesis of MK–0499, J. Org. Chem. 60 (1995) 4324–4330.

Varenne et al., Percutaneous Gene Therapy Using Recombinant Adenoviruses Encoding Human Herpes Simplex Virus Thymidine Kinase, Human PAI–1, and Human NOS3 in Balloon–Injured Porcine Coronary Arteries, Human Gene Therapy 11:1329–1339 (Jun. 10, 2000).

Windaus, Chem.Ber. 57 (1924) 1735–1737.

Ozaki et al., 5–Fluorouracil Derivatives XXIII. Synthesis and Antitumor Activities of 1–carbamoyl–5–fluorouracils Having Aromatic Ring, Chinese Journal of Chemistry, 1998, vol. 16, No. 2, 171–177.

* cited by examiner

ACYLATED 1,2,3,4-TETRAHYDRONAPHTHYL AMINES AND THEIR USE AS PHARMACEUTICAL AGENTS

The present invention relates to acylated 1,2,3,4-tetrahydronaphthyl amines of the general formula (I), with the definitions of $R^1$ to $R^5$ and A, B and C given below in the text, in any of their stereoisomeric forms or mixtures thereof in any ratio or the pharmaceutically acceptable salts thereof and their use as pharmaceutical agents.

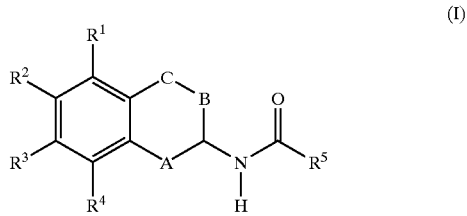

(I)

Endothelial NO synthase (eNOS, NOS-III) belongs to a group of three isoenzymes which produce nitric oxide (NO) by oxidation of arginine. Endothelially released NO is of central importance in a number of key cardiovascular mechanisms. It has a vasodilating effect and inhibits the aggregation of platelets, the adhesion of leukocytes to the endothelium and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are, extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349–353) were able by means of exercise training and the increase in shear stress associated therewith to obtain a marked increase in ecNOS.

Whether regulation at the post-transcriptional level is relevant in vivo, is not unambiguously proved. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides the lipid lowering, also in part to an increase in eNOS expression in vivo (Endres et al., Proc. Natl. Acad. Sci. USA 95 (1998) 8880–8885). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864–2870).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension, which may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329).

Some low molecular weight compounds which, in cell cultures, may lead to a direct effect on eNOS transcription and expression are disclosed in the literature. The statins which have already been mentioned are, however, the only substances for which it has been possible to date to show such an increase in eNOS in vivo as a side effect. In view of the known range of side effects of this class of substances, however, it is unclear how far this effect is present in a toxicologically unproblematic dose.

Liao et al. claim in WO 99/47153 and WO 00/03746 the use of rhoGTPase inhibitors and agents which influence the organization of the actin cytoskeleton for increasing eNOS in endothelial cells and for the therapy of various disorders such as, for example, strokes or pulmonary hypertension, without, however, indicating a specific way of achieving this.

Thus, there exists a strong need for compounds which upregulate eNOS-expression in endothelial cells. The object of the present invention is to provide compounds showing this ability.

This object is attained by acylated 1,2,3,4-tetrahydronaphthyl amines according to the general formula (I) in any of their stereoisomeric forms or mixtures thereof in any ratio or the pharmaceutically acceptable salts thereof.

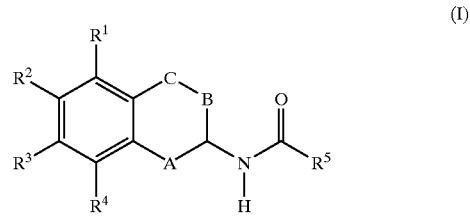

(I)

In the above formula (I),
$R^1$ and $R^4$ are independently of each other selected from the group consisting of: H; unsubstituted and at least mono-substituted $C_1$–$C_{10}$-alkyl, $C_2$–$C_{10}$-alkenyl and $C_2$–$C_{10}$-alkynyl, the substituents of which are selected from the group consisting of F, OH, $C_1$–$C_8$-alkoxy, ($C_1$–$C_8$-alkyl)

mercapto, CN, COOR$^6$, CONR$^7$R$^8$, and unsubstituted and at least monosubstituted phenyl and heteroaryl, the substituents of which are selected from the group consisting of halogens, pseudohalogens, C$_1$–C$_3$-alkyl, C$_1$–C$_3$-alkoxy and CF$_3$; unsubstituted and at least monosubstituted phenyl and heteroaryl, the substituents of which are selected from the group consisting of halogens, pseudohalogens, C$_1$–C$_3$-alkyl, C$_1$–C$_3$-alkoxy and CF$_3$; R$^9$CO; CONR$^{10}$R$^{11}$; COOR$^{12}$; CF$_3$; halogens; pseudohalogens; NR$^{13}$R$^{14}$; OR$^{15}$; S(O)$_m$R$^{16}$; SO$^2$NR$^{17}$R$^{18}$; and NO$_2$;

R$^2$ and R$^3$ are independently from each other selected from the group consisting of: H; halogens; pseudohalogens; unsubstituted and at least monosubstituted C$_1$–C$_{10}$-alkyl the substituents of which are selected from the group consisting of OH, phenyl, and heteroaryl; OH; C$_1$–C$_{10}$-alkoxy; phenoxy; S(O)$_m$R$^{19}$; CF$_3$; CN; NO$_2$; (C$_1$–C$_{10}$-alkyl)amino; di(C$_1$–C$_{10}$-alkyl)amino; (C$_1$–C$_6$-alkyl)-CONH—; unsubstituted and at least monosubstituted phenyl-CONH— and phenyl-SO$_2$—O—, the substituents of which are selected from the group consisting of halogens, pseudohalogens, CH$_3$ and methoxy; (C$_1$–C$_6$-alkyl)SO$_2$—O—, unsubstituted and at least monosubstituted (C$_1$–C$_6$-alkyl)CO, the substituents, of which are selected from the group consisting of F, di(C$_1$–C$_3$-alkyl)amino, pyrrolidinyl and piperidinyl; and phenyl-CO, the phenyl part of which can be substituted by one or more substituents from the group consisting of C$_1$–C$_3$-alkyl, halogens and methoxy;

A is selected from the group consisting of CH$_2$, CHOH and CH—(C$_1$–C$_3$-alkyl);

B is selected from the group consisting of CH$_2$ and CH—(C$_1$–C$_3$-alkyl);

C independently has the same meaning as B;

R$^5$ is a group Hetar which can be unsubstituted or carry one or more substituents selected from the group consisting of: halogens; pseudohalogens; NH$_2$; unsubstituted and at least monosubstituted C$_1$–C$_{10}$-alkyl, C$_2$–C$_{10}$-alkenyl, C$_2$–C$_{10}$-alkynyl, C$_1$–C$_{10}$-alkoxy, (C$_1$–C$_{10}$-alkyl)amino, di(C$_1$–C$_{10}$-alkyl)amino, the substituents of which are selected from the group consisting of F, OH, C$_1$–C$_8$-alkoxy, aryloxy, (C$_1$–C$_8$-alkyl)mercapto, NH$_2$, (C$_1$–C$_8$-alkyl)amino, and di(C$_1$–C$_8$-alkyl)amino; C$_3$–C$_5$-alkandiyl; phenyl; heteroaryl; aryl- or heteroaryl-substituted C$_1$–C$_4$-alkyl; CF$_3$; NO$_2$; OH; phenoxy; benzyloxy; (C$_1$–C$_{10}$-alkyl)COO; S(O)$_m$R$^{20}$; SH; phenylamino; benzylamino; (C$_1$–C$_{10}$-alkyl)-CONH—; (C$_1$–C$_{10}$-alkyl)-CON(C$_1$–C$_4$-alkyl)-; phenyl-CONH—; phenyl-CON(C$_1$–C$_4$-alkyl)-; heteroaryl-CONH—; heteroaryl-CON(C$_1$–C$_4$-alkyl)-; (C$_1$–C$_{10}$-alkyl)-CO; phenyl-CO; heteroaryl-CO; CF$_3$—CO; —OCH$_2$O—; —OCF$_2$O—; —OCH$_2$CH$_2$O—; —CH$_2$CH$_2$O—; COOR$^{21}$; CONR$^{22}$R$^{23}$; CNH(NH$_2$); SO$_2$NR 24R$^{25}$; R$^{26}$SO$_2$NH—; R$^{27}$SO$_2$N(C$_1$–C$_6$-alkyl)-; and saturated or at least monounsaturated aliphatic, mononuclear 5- to 7-membered heterocycles containing 1 to 3 heteroatoms selected from the group consisting of N, O and S, which heterocycles can be substituted by one or more substituents selected from the group consisting of halogens, C$_1$–C$_3$-alkyl, C$_1$–C$_3$-alkoxy, OH, oxo and CF$_3$, where said heterocycles can optionally be condensed to the said group Hetar; wherein all aryl, heteroaryl, phenyl, aryl-containing, heteroaryl-containing and phenyl-containing groups, which are optionally present in the said substituents of the said group Hetar, can be substituted by one or more substituents selected from the group consisting of halogens, pseudohalogens, C$_1$–C$_3$-alkyl, OH, C$_1$–C$_3$-alkoxy, and CF$_3$;

R$^6$ is selected from the group consisting of:
H; C$_1$–C$_{10}$-alkyl, which can be substituted by one or more substituents selected from the group consisting of F, C$_1$–C$_8$-alkoxy, and di(C$_1$–C$_8$-alkyl)amino; aryl-(C$_1$–C$_4$-alkyl) and heteroaryl-(C$_1$–C$_4$-alkyl), which can be substituted by one or more substituents selected from the group consisting of halogens, C$_1$–C$_4$-alkoxy, and di(C$_1$–C$_6$-alkyl)amino;

R$^7$ is selected from the group consisting of:
H; C$_1$–C$_{10}$-alkyl which can be substituted by one or more substituents selected from the group consisting of F, C$_1$–C$_8$-alkoxy, di(C$_1$–C$_8$-alkyl)amino and phenyl; phenyl; indanyl; and heteroaryl; and wherein each of the aforementioned aromatic groups can be unsubstituted or carry one or more substituents from the group consisting of halogens, pseudohalogens, C$_1$–C$_3$-alkyl, C$_1$–C$_3$-alkoxy and CF$_3$;

R$^8$ is H or C$_1$–C$_{10}$-alkyl;

R$^9$ is selected from the group consisting of: C$_1$–C$_{10}$-alkyl which can be unsubstituted or carry one or more substituents from the group consisting of: F, (C$_1$–C$_4$)-alkoxy, di(C$_1$–C$_3$-alkyl)amino; and unsubstituted and at least monosubstituted phenyl and heteroaryl, the substituents of which are selected from the group consisting of C$_1$–C$_3$-alkyl, C$_1$–C$_3$-alkoxy, halogens, pseudohalogens, and CF$_3$;

R$^{10}$ independently has the same meaning as R$^7$;

R$^{11}$ independently has the same meaning as R$^8$;

R$^{12}$ independently has the same meaning as R$^6$;

R$^{13}$ is selected from the group consisting of: H; C$_1$–C$_6$-alkyl; unsubstituted and substituted phenyl, benzyl, heteroaryl, (C$_1$–C$_6$-alkyl)-CO, phenyl-CO, and heteroaryl-CO, the substituents of which are selected from the group consisting of halogens, pseudohalogens, C$_1$–C$_3$-alkyl, C$_1$–C$_3$-alkoxy, and CF$_3$, and wherein one or more of these substituents can be present;

R$^{14}$ independently has the same meaning as R$^{13}$;

R$^{15}$ is selected from the group consisting of: H; C$_1$–C$_{10}$-alkyl; (C$_1$–C$_3$-alkoxy)-C$_1$–C$_3$-alkyl; and substituted and unsubstituted benzyl, phenyl and heteroaryl, the substituents of which are selected from the group consisting of halogens, pseudohalogens, C$_1$–C$_3$-alkyl, C$_1$–C$_3$-alkoxy, and CF$_3$, and wherein one or more of these substituents can be present;

R$^{16}$ is selected from the group consisting of: C$_1$–C$_{10}$-alkyl which can be substituted by one or more substituents selected from the group consisting of F, OH, C$_1$–C$_8$-alkoxy, aryloxy, (C$_1$–C$_8$-alkyl)mercapto, (C$_1$–C$_8$-alkyl)amino and di(C$_1$–C$_8$-alkyl)amino; CF$_3$; and substituted and unsubstituted phenyl and heteroaryl, the substituents of which are selected from the group consisting of halogens, pseudohalogens, C$_1$–C$_3$-alkyl, C$_1$–C$_3$-alkoxy and CF$_3$, and wherein one or more of these substitutents can be present;

R$^{17}$ independently has the same meaning as R$^7$;

R$^{18}$ independently has the same meaning as R$^8$;

R$^{19}$ independently has the same meaning as R$^{16}$;

R$^{20}$ independently has the same meaning as R$^{16}$;

R$^{21}$ independently has the same meaning as R$^6$;

R$^{22}$ independently has the same meaning as R$^7$;

R$^{23}$ independently has the same meaning as R$^8$;

R$^{24}$ independently has the same meaning as R$^7$;

R$^{25}$ independently has the same meaning as R$^8$;

R$^{26}$ independently has the same meaning as R$^{16}$;

R$^{27}$ independently has the same meaning as R$^{16}$;

heteroaryl is a 5 to 10-membered, aromatic, mono- or bicyclic heterocycle containing one or more heteroatoms selected from the group consisting of N, O and S;

the group Hetar is a 5 to 10-membered, aromatic, mono- or bicyclic heterocycle containing one or more heteroatoms selected from the group consisting of N, O and S;

aryl is phenyl, naphth-1-yl or naphth-2-yl; and m is 0, 1 or 2;

with the proviso that, in case $R^1$, $R^2$, $R^3$ and $R^4$ are hydrogen or one of the substituents, $R^1$, $R^2$, $R^3$ or $R^4$ is $C_1$–$C_6$-alkoxy, $R^5$ is not unsubstituted pyridyl or unsubstituted or substituted 4-oxoquinolinyl.

If, in the compounds of formula (I), groups or substituents such as, for example, aryl, heteroaryl, alkyl etc., can be present several times, they all independently from each other have the meanings indicated and can hence, in each individual case, be identical with or different from each other. One example is the di($C_1$–$C_{10}$-alkyl)amino group in which the alkyl substitutents can be identical or different.

Alkyl, alkenyl and alkynyl residues can be linear or branched, acyclic or cyclic. This also applies when they are part of other groups, for example in alkoxy groups, alkoxycarbonyl groups or amino groups, or when they are substituted.

Examples for alkyl groups are methyl, ethyl, propyl, butyl, pentyl, hexyl, heptyl, octyl, nonyl, decyl, the n-isomers of these residues, isopropyl, isobutyl, isopentyl, sec-butyl, tert-butyl, neopentyl, 3,3-dimethylbutyl. The term alkyl here also expressly includes cycloalkyl residues and cycloalkyl-alkyl-residues (alkyl substituted by cycloalkyl) containing at least three carbon atoms. Examples for such cycloalkyl residues are cyclopropyl, cyclobutyl, cyclopentyl, cyclohexyl, cycloheptyl and cyclooetyl. All cycloalkyl groups can be substituted by one or more identical or different ($C_1$–$C_4$)-alkyl residues, in particular by methyl. Examples for substituted cycloalkyl residues are 4-methylcyclohexyl, 4-tert-butylcyclohexyl or 2,3-dimethylcyclopentyl. Furthermore, unless stated otherwise, the term alkyl here also includes unsubstituted alkyl residues as well as alkyl residues which are substituted by one or more, for example one, two, three or four, identical or different residues, for example, aryl groups. In substituted alkyl residues, for example arylalkyl, hydroxyalkyl such as —($C_1$–$C_3$)-alkyl-OH or alkoxyalkyl such as —($C_1C_3$)-alkyl-O—($C_1$–$C_4$)-alkyl, the substituents can be present in any desired position.

Examples for alkenyl and alkynyl groups are the vinyl residue, the 1-propenyl residue, the 2-propenyl residue (allyl residue), the 2-butenyl residue, the 2-methyl-2-propenyl residue, the 3-methyl-2-butenyl residue, the ethynyl residue, the 2-propynyl residue (propargyl residue), the 2-butynyl residue or the 3-butynyl residue. The term alkenyl here also expressly includes cycloalkenyl residues and cycloalkenyl-alkyl-residues (alkyl substituted by cycloalkenyl) containing at least three carbon atoms. Examples for cycloalkenyl residues are cyclopentenyl, cyclohexenyl, cycloheptenyl and cyclooctenyl. All cycloalkenyl groups can be substituted by one or more identical or different ($C_1$–$C_4$)-alkyl residues, in particular by methyl. Furthermore, unless stated otherwise, the term alkenyl and alkynyl here also includes unsubstituted alkenyl and alkynyl residues as well as alkenyl and alkynyl residues which are substituted by one or more, for example one, two, three or four, identical or different residues, for example aryl groups. In substituted alkenyl and alkynyl residues, for example, arylalkyl, hydroxyalkenyl such as —($C_2$–$C_3$)alkenyl-OH or alkoxyalkenyl such as ($C_1$–$C_3$-alkyl)-O—($C_2$–$C_4$-alkenyl)-, the substituents can be present in any desired position.

Examples for $C_3$–$C_5$-alkandiyl are —$CH_2CH_2CH_2$—, —$CH_2$—$CH(CH_3)$, —$CH_2CH_2CH_2CH_2$— and —$CH_2CH_2CH_2CH_2CH_2$— groups.

If not stated otherwise, the above-mentioned phenyl residues, naphthyl and indanyl residues and heterocyclic residues (including heteroaryl residues) can be unsubstituted or can carry one or more, for example one, two, three or four, of the substituents indicated in the above definition which can be in any desired position. If in compounds of the formula (I) nitro groups are present as substituents, in total only up to two nitro groups are preferably present in the molecule. In monosubstituted phenyl residues the substituent can be in the 2-position, the 3-position or the 4-position, in disubstituted phenyl residues the substituents can be in 2,3-position, 2,4-position, 2,5-position, 2,6-position, 3,4-position or 3,5-position. In trisubstituted phenyl residues the substituents can be in 2,3,4-position, 2,3,5-position, 2,3,6-position, 2,4,5-position, 2,4,6-position or 3,4,5-position. In fourfold substituted phenyl residues, the substituents can be in the 2,3,4,5-position, the 2,3,4,6-position, or the 2,3,5,6-position. Tolyl (=methylphenyl) can be 2-tolyl, 3-tolyl or 4-tolyl. Naphthyl can be 1-naphthyl or 2-naphthyl. In monosubstituted 1-naphthyl residues the substituent can be in the 2-position, the 3-position, the 4-position, the 5-position, the 6-position, the 7-position or the 8-position; in monosubstituted 2-naphthyl residues in the 1-position, the 3-position, the 4-position, the 5-position, the 6-position, the 7-position or the 8-position. In higher substituted naphthyl radicals, for example 1-naphthyl radicals or 2-naphthyl radicals which carry two or three substituents, the substituents can also be situated in all possible positions. Indanyl residues include indan-1-yl residues and indan-2-yl residues which can be unsubstituted or carry one or more of the substituents indicated. In case the indanyl residues are substituted, the substituent or substituents can be in any of the positions possible.

The above definitions as well as the following definitions relating to monovalent residues equally apply to the divalent residues phenylene, naphthylene and heteroarylene. Those divalent residues can be attached to the adjacent groups by any ring carbon atom. In the case of a phenylene residue, these can be in 1,2-position (ortho-phenylene), 1,3-position (meta-phenylene) or 1,4-position (para-phenylene). In the case of a naphthylene residue the free bonds can be in 1,2-position (=1,2-naphthylene or 1,2-naphthalinediyl) or in 1,3position, 1,4-position, 1,5-position, 1,6-position, 1,7-position, 1,8-position, 2,3-position, 2,6-position or 2,7-position. In the case of 5-membered ring aromatics containing one heteroatom such as, for example, thiophene or furan, the two free bonds can be in 2,3 position, 2,4-position, 2,5-position or 3,4-position. A divalent residue derived from pyridine can be a 2,3-, 2,4-, 2,5-, 2,6-, 3,4- or 3,5-pyridinediyl residue. In the case of unsymmetrical divalent residues, the present invention includes all positional isomers, i.e., in the case of a 2,3-pyridinediyl residue, for example, it includes the compound in which the one adjacent group is present in the 2-position and the other adjacent group is present in the 3-position as well as the compound in which the one adjacent group is present in the 3-position and the other adjacent group is present in the 2-position.

Unless stated otherwise, heteroaryl residues, heteroarylene residues, heterocyclyl residues and rings which are formed by two groups bonded to a nitrogen are preferably derived from heterocycles which contain one, two, three or four heteroatoms which can be identical or different; more preferably they are derived from heterocycles which contain one, two, or three, in particular one or two, heteroatoms which can be identical or different. Unless stated otherwise, the heterocycles can be monocyclic or polycyclic, for example monocyclic, bicyclic or tricyclic. Preferably they are monocyclic or bicyclic. The rings preferably are 5-membered rings, 6-membered rings or 7-membered rings. Examples of monocyclic and bicyclic heterocyclic systems from which residues occurring in the compounds of the formula (I) can be derived, are pyrrole, furan, thiophene, imidazole, pyrazole, 1,2,3-triazole, 1,2,4-triazole, 1,3-dioxole, 1,3-oxazole (=oxazole), 1,2-oxazole (=isoxazole), 1,3-thiazole (=thiazole), 1,2-thiazole (=isothiazole), tetrazole, pyridine, pyridazine, pyrimidine, pyrazine, pyran, thiopyran, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzimidazole, benzodioxol, quinoline, isoquinoline, cinnoline, quinazoline, quinoxaline, phthalazine, thienothiophenes, 1,8-naphthyridine and other naphthyridines, pteridin, or phenothiazine, each of them in saturated form (perhydro form) or in partially unsaturated form (for example in the dihydro form or the tetrahydro form) or in maximally unsaturated form, in case the respective forms are known and stable. The term "aryl" and the term "heteroaryl" as used herein comprise bicyclic residues in which both cycles are aromatic as well as bicyclic residues in which only one cycle is aromatic. Independently, the same applies to the term "group Ar" or the term "group Hetar", respectively. Suitable heterocycles include, for example, for example, the saturated heterocycles pyrrolidine, piperidine, piperazine, morpholine and thiomorpholine. The degree of saturation of heterocyclic groups is indicated in their individual definitions. Unsaturated heterocycles can contain, for example, one, two or three double bonds within the ring system. 5-membered rings and 6-membered rings can in particular also be aromatic.

Substituents which may be derived from these heterocycles can be attached via any suitable carbon atom. Residues derived from nitrogen heterocycles can carry a hydrogen atom or a substituent on a ring nitrogen atom, and examples include pyrrole, imidazole, pyrrolidine, morpholine, piperazine residues, etc. Those nitrogen heterocyclic residues can also be attached via a ring nitrogen atom, in particular if the respective heterocyclic residue is bonded to a carbon atom. For example, a thienyl residue can be present as 2-thienyl residue or 3-thienyl residue, a furyl residue as 2-furyl residue or 3-furyl residue, a pyridyl residue as 2-pyridyl residue, 3-pyridyl residue or 4-pyridyl residue, a piperidinyl residue as 1-piperidinyl residue (=piperidino residue), 2-piperidinyl residue, 3-piperidinyl residue or 4-piperidinyl residue, a (thio)morpholinyl residue as 2-(thio)morpholinyl residue, 3-(thio)morpholinyl residue or 4-(thio)morpholinyl residue (=thiomorpholino residue). A residue derived from 1,3-thiazole or imidazole which is attached via a carbon atom can be attached via the 2-position, the 4-position or the 5-position.

In case a heterocyclic group is substituted, it can carry one or more, for example one, two, three or four, identical or different substituents. Substituents in heterocycles can be present in any desired positions, for example in a 2-thienyl residue or 2-furyl residue in the 3-position and/or in the 4-position and/or in the 5-position, in a 3-thienyl residue or 3-furyl residue in the 2-position and/or in the 4-position and/or in the 5-position, in a 2-pyridyl residue in the 3-position and/or in the 4-position and/or in the 5-position and/or in the 6-position, in a 3-pyridyl residue in the 2-position and/or in the 4-position and/or in the 5-position and/or in the 6-position, in a 4-pyridyl residue in the 2-position and/or in the 3-position and/or in the 5-position and/or in the 6-position. Suitable nitrogen heterocycles can also be present as N-oxides or as quarternary salts containing a counterion which is derived from a pharmaceutically acceptable acid. Pyridyl residues, for example, can be present as pyridine-N-oxides.

Halogen is fluorine, chlorine, bromine or iodine, preferably fluorine or chlorine.

Examples for pseudohalogens are CN and $N_3$, a preferred pseudohalogen is CN.

The present invention includes all stereoisomeric forms of the compounds of the formula (I). Centers of asymmetry that are present in the compounds of formula (I) all independently of one another have S configuration or R configuration. The invention includes all possible enantiomers and diastereomers and mixtures of two or more stereoisomers, for example mixtures of enantiomers and/or diastereomers, in all ratios. Thus, compounds according to the present invention which can exist as enantiomers can be present in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. All these forms are an object of the present invention. The preparation of individual stereoisomers can be carried out, if desired, by separation of a mixture by customary methods, for example by chromatography or crystallization, by the use of stereochernically uniform starting materials for the synthesis or by stereoselective synthesis. Optionally a derivatization can be carried out before a separation of stereoisomers. The separation of a mixture of stereoisomers can be carried out at the stage of the compounds of the formula (I) or at the stage of an intermediate during the synthesis. The present invention also includes all tautomeric forms of the compounds of formula (I).

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be present on these groups and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art.

If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art as, for example, by contacting these with an organic or inorganic acid or base in a solvent or dispersant, or by anion exchange or cation exchange with other salts.

The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

The present invention furthermore includes all solvates of compounds of the formula (I), for example hydrates or adducts with alcohols, active metabolites of the compounds of the formula (II), and also derivatives and prodrugs of the compounds of the formula (I) which contain physiologically tolerable and cleavable groups, for example esters, amides and compounds in which the N—H group depicted in formula (I) is replaced with an N-alkyl group, such as N-methyl, or with an N-acyl group, such as N-acetyl or N-argininyl, including pharmaceutically acceptable salts formed on functional groups present in the Nacyl group.

Preferred compounds of the formula (I) are those compounds in which one or more, including all, of the residues contained therein have the meanings given below, with all combinations of preferred substituent definitions being a subject of the present invention. With respect to all preferred compounds of the formula (I) the present invention also includes all stereoisomeric forms and mixtures thereof in all ratios, and their pharmaceutically acceptable salts.

In preferred embodiments of the present invention, the substituents $R^1$ to $R^5$, A, B and C and the groups aryl and heteroaryl of the formula (I) independently of each other have the following meanings. Hence, one or more of the substituents $R^1$ to $R^5$ and A, B and C can have the preferred meanings, the more preferred meanings, the even more preferred meanings, the most preferred meanings, or the particularly preferred meanings given below.

$R^1$ is preferably selected from the group consisting of: H; $C_1$–$C_4$-alkyl; $C_1$–$C_4$-alkoxy; $CF_3$; halogens; pseudohalogens; ($C_1$–$C_4$-alkyl)-S(O)$_m$—; and unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$, where heteroaryl is selected from the group consisting of 5- and 6-membered heterocycles containing one or more heteroatoms selected from the group consisting of N, O, and S; $R^1$ is more preferably H, halogen or $C_1$–$C_4$-alkyl.

$R^2$ is preferably selected from the group consisting of: H; halogens; pseudohalogens; and $C_1$–$C_3$-alkyl; $R^2$ is more preferably H.

$R^3$ is preferably selected from the group consisting of: H; halogens; pseudohalogens; and $C_1$–$C_3$-alkyl; $R^3$ is more preferably H.

$R^4$ is preferably selected from the group consisting of: —H; $C_1$–$C_4$-alkyl; $C_1$–$C_4$-alkoxy; $CF_3$; halogens; pseudohalogens; ($C_1$–$C_4$-alkyl)-S(O)$_m$—; and unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$, where heteroaryl is selected from the group consisting of 5- and 6-membered heterocycles containing one or more heteroatoms selected from the group consisting of N, O, and S; $R^4$ is more preferably H, halogen or $C_1$–$C_4$-alkyl; $R^4$ is most preferably H.

$R^1$ to $R^4$ are in particular each H.

A is preferably selected from the group consisting of $CH_2$ and $CHOH$; A is in particular $CH_2$.

B and C are preferably independently of each other selected from the group consisting of $CH_2$ and CH—$CH_3$; more preferably B is a $CH_2$ unit while C is $CH_2$ or CH—$CH_3$; Most preferably B and C are $CH_2$.

$R^5$ is preferably a group Hetar which can be unsubstituted or carry one or more substituents selected from the group consisting of: halogens; CN; $NH_2$; unsubstituted and at least monosubstituted $C_1$–$C_8$-alkyl, $C_2$–$C_8$-alkenyl, $C_2$–$C_8$-alkynyl, $C_1$–$C_8$-alkoxy, ($C_1$–$C_8$-alkyl)amino, di($C_1$–$C_8$-alkyl)amino, the substituents of which are selected from the group consisting of F, $C_1$–$C_6$-alkoxy, phenoxy, ($C_1$–$C_6$-alkyl)mercapto, $NH_2$, ($C_1$–$C_6$-alkyl)amino, and di($C_1$–$C_6$-alkyl)amino; $C_3$–$C_5$-alkandiyl; phenyl; heteroaryl; phenyl- or heteroaryl-substituted $C_1$–$C_2$-alkyl; $CF_3$; OH; phenoxy; benzyloxy; ($C_1$–$C_6$-alkyl)COO; S(O)$_m$($C_1$–$C_6$)-alkyl; S(O)$_m$-phenyl; S(O)$_m$-heteroaryl; SH; phenylamino; benzylamino; ($C_1$–$C_6$-alkyl)-CONH—; ($C_1$–$C_6$-alkyl)-CON($C_1$–$C_4$-alkyl)-; phenyl-CONH—; phenyl-CON($C_1$–$C_4$-alkyl)-, heteroaryl-CONH—; heteroaryl-CON($C_1$–$C_4$-alkyl)-; ($C_1$–$C_6$-alkyl)-CO; phenyl-CO; heteroaryl-CO; $CF_3$—CO; —OCH$_2$O—; —OCF$_2$O—; —OCH$_2$CH$_2$O—; —CH$_2$CH$_2$O—; COO($C_1$–$C_6$alkyl); —CONH$_2$; —CONH ($C_1$–$C_6$-alkyl); —CON(di($C_1$–$C_6$-alkyl)); CNH(NH$_2$); —SO$_2$NH$_2$; —SO$_2$NH($C_1$–$C_6$-alkyl); —SO$_2$NH(phenyl); —SO$_2$N(di($C_1$–$C_6$-alkyl)); ($C_1$–$C_6$-alkyl)SO$_2$NH—; ($C_1$–$C_6$-alkyl)SO$_2$N($C_1$–$C_6$-alkyl)-; phenyl-SO$_2$NH—; phenyl-SO$_2$N($C_1$–$C_6$-alkyl)-; heteroaryl-SO$_2$NH—; heteroaryl-SO$_2$N($C_1$–$C_6$-alkyl)-; and saturated or at least monounsaturated aliphatic, mononuclear 5- to 7-membered heterocycles containing 1 to 3 heteroatoms selected from the group consisting of N, O, and S, which heterocycles can be substituted by one or more substituents selected from the group consisting of halogens, $C_1$–$C_3$-alkyl, $C_1$–$C_3$-alkoxy, OH, oxo and $CF_3$, where said heterocycles can optionally be condensed to the said group Ar or the said group Hetar; wherein all heteroaryl, phenyl, heteroaryl-containing and phenyl-containing groups, which are optionally present in the said substituents of the said group Ar or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^5$ is more preferably a group Hetar which can be unsubstituted or carry one or more substituents selected from the group consisting of: halogens; CN; $NH_2$; unsubstituted and at least monosubstituted $C_1$–$C_6$-alkyl, $C_2$–$C_6$-alkenyl, $C_2$–$C_6$-alkynyl, $C_1$–$C_3$-alkoxy, ($C_1$–$C_4$alkyl)amino, di($C_1$–$C_4$-alkyl)amino, the substituents of which are selected from the group consisting of F, $C_1$–$C_3$-alkoxy, ($C_1$–$C_3$-alkyl)mercapto, and $NH_2$; $C_3$–$C_5$-alkandiyl; phenyl; heteroaryl; phenyl- or heteroaryl-substituted $C_1$–$C_2$-alkyl; $CF_3$; OH; ($C_1$–$C_4$-alkyl)COO; S(O)$_m$($C_1$–$C_4$)-alkyl; ($C_1$–$C_4$-alkyl)-CONH—; ($C_1$–$C_4$-alkyl)-CON($C_1$–$C_4$-alkyl)-; ($C_1$–$C_4$alkyl)-CO; phenyl-CO; heteroaryl-CO; $CF_3$—CO; —OCH$_2$O—; —OCF$_2$O—; —OCH$_2$CH$_2$O—; —CH$_2$CH$_2$O—; COO($C_1$–$C_6$-alkyl); —CONH$_2$; —CONH ($C_1$–$C_4$-alkyl); —CON(di($C_1$–$C_4$-alkyl)); CNH(NH$_2$); —SO$_2$NH$_2$; —SO$_2$NH($C_1$–$C_4$-alkyl); —SO$_2$NH(phenyl); —SO$_2$N(di($C_1$–$C_4$-alkyl)); ($C_1$–$C_4$-alkyl)SO$_2$NH—; ($C_1$–$C_4$-alkyl)SO$_2$N($C_1$–$C_4$-alkyl)-; and saturated or at least monounsaturated aliphatic, mononuclear 5- to 7-membered heterocycles containing 1 to 3 heteroatoms selected from the group consisting of N, O, and S, which heterocycles can be substituted by one or more substituents selected from the group consisting of halogens, $C_1$–$C_3$-alkyl, $C_1$–$C_3$-alkoxy, OH, oxo and $CF_3$, where said heterocycles can optionally be condensed to the said phenyl or the said group Hetar; wherein all heteroaryl, phenyl, heteroaryl-containing and phenyl-containing groups, which are optionally present in the said substituents of the said phenyl or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^5$ is even more preferably a group Hetar which can be unsubstituted or carry one or more substituents selected from the group consisting of. F; Cl; Br; $C_1$–$C_3$-alkyl; $C_1$–$C_3$-alkoxymethyl; 2-amino-3,3,3-trifluoro-propyl-; $CF_3$; $C_3$–$C_5$-alkandiyl; phenyl; heteroaryl; benzyl; heteroarylmethyl; OH; $C_1$–$C_3$-alkoxy; phenoxy; trifluoromethoxy; 2,2,2-trifluoroethoxy; ($C_1$–$C_4$-alkyl)COO; ($C_1$–$C_3$-alkyl) mercapto; phenylmercapto; ($C_1$–$C_3$-alkyl)sulfonyl; phenylsulfonyl; $NH_2$; ($C_1$–$C_4$-alkyl)amino; di($C_1$–$C_4$-alkyl) amino; ($C_1$–$C_3$-alkyl)-CONH—; ($C_1$–$C_3$-alkyl)-$SO_2$NH—; ($C_1$–$C_3$-alkyl)-CO; phenyl-CO; —$OCH_2O$—; —$OCF_2O$—; —$CH_2CH_2O$—; COO($C_1$–$C_4$-alkyl); —$CONH_2$; —CONH ($C_1$–$C_4$-alkyl); —CON(di($C_1$–$C_4$-alkyl)); CN; —$SO_2NH_2$; —$SO_2$NH($C_1$–$C_4$-alkyl); —$SO_2$N(di($C_1$–$C_4$-alkyl)); pyrrolidinyl; piperidinyl; morpholinyl; and thiomorpholinyl; wherein all heteroaryl, phenyl, heteroaryl-containing and phenyl-containing groups, which are optionally present in the said substituents of the said phenyl or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^5$ is most preferably selected from the group consisting of. benzo[1,3]dioxol-5-yl, 2,2-difluoro-benzo[1,3]dioxol-5-yl, 2,3-dihydrobenzofuran-5-yl, 1-(4-chloro-phenyl)-5-trifluoromethyl-1H-pyrazole-4-yl, 1-(4-fluoro-phenyl)-3,5-dimethyl-1H-pyrazole-4-yl, 1H-benzotriazole-5-yl, 1H-indole-4-yl, 1H-indole-6-yl, 1-isopropyl-2-trifluoromethyl-1H-benzoimidazole-5-yl, 1-methyl-3-oxo-1,2,3,4-tetrahydro-quinoxaline-6-yl, 1-phenyl-5-trifluoromethyl-1H-pyrazole-4-yl, 2-(2-hydroxy-pyridin-4-yl)-1H-benzoimidazole-5-yl, 2-(4-cyano-phenyl)-1H-benzoimidazole-5-yl, 2,4-dimethyl-oxazole-5-yl, 2,4-dimethyl-pyrimidine-5-yl, 2,4-dimethyl-thiazole-5-yl, 2,5-dimethyl-1H-pyrrole-3-yl, 2,5-dimethyl-1-phenyl-1H-pyrrole-3-yl, 2,5-dimethyl-1-pyridin-4-ylmethyl-1H-pyrrolyl, 2,5-dimethyl-2H-pyrazole-3-yl, 2,6-dichloro-pyrid-3-yl, 2,6-dimethoxy-pyrid-3-yl, 2,6-dimethyl-pyrid-3-yl, 2-amino-4,6-dimethyl-pyrid-3-yl, 2-amino-6-chloro-pyrid-3-yl, 2-amino-pyrid-3-yl, 2-chloro-6-methyl-pyrid-3-yl, 2-chloro-pyrid-4-yl, 2-cyclopropyl-4-methyl-thiazole-5-yl, 2-dimethylamino-4-methyl-thiazole-5-yl, 2-dimethylamino-pyrid-4-yl, 2-ethyl-5-methyl-2H-pyrazole-3-yl, 2-hydroxy-6-methyl-pyrid-3-yl, 2-methyl-1H-benzoimidazole-5-yl, 2-methyl-3H-benzoimidazole-5-yl, 2-methyl-pyrid-3-yl, 2-methyl-6-trifluoromethyl-pyrid-3-yl, 2-methyl-thiazole-5-yl, 2-morpholin-4-yl-pyridin-4-yl, 2-morpholin-4-yl-pyrimidine-5-yl, 2-pyrrolidin-1-yl-pyridin-4-yl, 3,5-dimethyl-1H-pyrazole-4-yl, 3-amino-5,6-dimethyl-pyrazine-2-yl, 3-amino-5-methyl-pyrazine-2-yl, 3-amino-pyrazine-2-yl, 3H-benzoimidazole-5-yl, 1H-benzoimidazole-5-yl, 3-methyl-isoxazole-4-yl, 4,6-dimethylpyrid-3-yl, 4-amino-2-ethylsulfanyl-pyrimidine-5-yl, 4-amino-2-methyl-pyrimidine-5-yl, 4-methyl-thiazole-5-yl, pyridine-2-yl, pyridine-3-yl, pyridine-4-yl, 5-thiophen-2-yl-pyrid-3-yl, 2-methyl-4-trifluoromethyl-thiazol-5-yl, 5,6,7,8-tetrahydro-quinoline-3-yl, 5-amino-1-phenyl-1H-pyrazole-4-yl, 5-methyl-1-phenyl-1H-pyrazole-4-yl, 5-methyl-isoxazole-3-yl, 5-methyl-pyrid-3-yl, 5-methyl-pyrazine-2-yl, 6-chloro-pyrid-3-yl, 6-cyano-pyrid-3-yl, 6-dimethylamino-pyrid-3-yl, 6-ethynyl-pyrid-3-yl, 6-methoxymethyl-pyrid-3-yl, 6-methoxypyrid-3-yl, 6-methyl-2-methylamino-pyrid-3-yl, 6-methylamino-pyrazine-2-yl, 6-methylpyrid-3-yl, 6-morpholin-4-yl-pyrid-3-yl, 6-pyrrolidin-1-yl-pyrid-3-yl, imidazo[1,2a]pyridine-2-yl, 6-trifluoromethyl-pyrid-3-yl, and pyrimidine-4-yl.

Heteroaryl is preferably a 5 to 10-membered, aromatic, mono- or bicyclic heterocycle containing one, two or three heteroatoms selected from the group consisting of N, O, and S; heteroaryl is most preferably selected from the group consisting of: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl.

The group Hetar is preferably a 5 to 10-membered, aromatic, mono- or bicyclic heterocycle containing one, two or three heteroatoms selected from the group consisting of N, O, and S; the group Hetar is most preferably selected from the group consisting of: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofaranyl, benzothiophenyl, and indazolyl.

Aryl is preferably phenyl.

m is preferably 0 or 2.

Compounds of the formula (I) in which some or all of the above-mentioned groups have the preferred meanings, the more preferred meanings, the even more preferred meanings, the most preferred meanings, or the particularly preferred meanings defined above are also an object of the present invention.

In another embodiment of the present invention, the substituents $R^1$ to $R^5$, A, B and C and the groups aryl and heteroaryl according to the formula (I) have the following meanings.

$R^1$ and $R^4$ are independently from each other selected from the group consisting of: H; unsubstituted and at least monosubstituted $C_1$–$C_{10}$-alkyl, $C_2$–$C_{10}$-alkenyl and $C_2$–$C_{10}$-alkynyl, the substituents of which are selected from the group consisting of F, OH, $C_1$–$C_6$-alkoxy, ($C_1$–$C_6$-alkyl) mercapto, CN, $COOR^6$, $CONR^7R^8$, unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; $R^9CO$; $CONR^{10}, R^{11}$, $COOR^{12}$; $CF_3$; halogens; pseudohalogens; $NR^{13}R^{14}$; $OR^{15}$; $S(O)_m R^{16}$; $SO_2NR^{17}R^{18}$; and $NO_2$;

$R^2$ and $R^3$ are independently of each other selected from the group consisting of: H; halogens; pseudohalogens; unsubstituted and at least monosubstituted $C_1$–$C_6$-alkyl, the substituents of which are selected from the group consisting of OH, phenyl, and heteroaryl; OH; $C_1$–$C_6$-alkoxy; phenoxy; $S(O)_m R^{19}$; $CF_3$; CN; $NO_2$; ($C_1$–$C_6$-alkyl)amino; di($C_1$–$C_6$-alkyl)amino; ($C_1$–$C_6$-alkyl)-CONH—; unsubstituted and at least monosubstituted phenyl-CONH and phenyl-$SO_2$—O—, the substituents of which are selected from the group consisting of halogens, pseudohalogens, $CH_3$ and methoxy; ($C_1$–$C_6$-alkyl)$SO_2$—O—, unsubstituted and at least monosubstituted ($C_1$–$C_6$-alkyl)CO, the substituents of which are selected from the group consisting of F, di($C_1$–$C_3$-alkyl)amino, pyrrolidinyl and piperidinyl; and phenyl-CO, the phenyl part of which can be substituted by one or more substituents from the group consisting of $C_1$–$C_3$-alkyl, halogens and methoxy;

A is $CH_2$, CHOH or CH—($C_1$–$C_3$-alkyl);

B is $CH_2$ or CH—($C_1$–$C_3$-alkyl);

C independently has the same meaning as B;

$R^5$ is an aryl or a heteroaryl group which can be unsubstituted or carry one or more substituents selected from the group consisting of: halogens; pseudohalogens; $C_1$–$C_{10}$alkyl; $C_3$–$C_5$-alkandiyl; phenyl; phenyl substituted $C_1$–$C_4$-alkyl; $CF_3$; OH; $C_1$–$C_{10}$-alkoxy; phenoxy; benzyloxy; $CF_3O$; ($C_1$–$C_{10}$-alkyl)COO; $S(O)_mR^{20}$; ($C_1$–$C_{10}$-alkyl)amino; di($C_1C_{10}$-alkyl)amino; ($C_1$–$C_{10}$-alkyl)-CONH—; ($C_1$–$C_{10}$-alkyl)-CON($C_1$–$C_3$-alkyl)-; ($C_1$–$C_{10}$alkyl)-CO; $CF_3$—CO; —$OCH_2O$—; —$OCF_2O$—; —$OCH_2CH2O$—; —$CH_2CH2O$—; phenylamino; phenyl-CO; $COOR^{21}$; $CONR^{22}R^{23}$; $SO_2NR^{24}R^{25}$; and aromatic or aliphatic, mononuclear 5-to-7-membered heterocycles containing 1 to 3 heteroatoms from the group consisting of N, O, and S which can be substituted by one or more substituents from the group consisting of halogens, $C_1$–$C_3$-alkyl, $C_1$–$C_3$-alkoxy and $CF_3$; wherein all phenyl groups and phenyl-containing groups which may be present in the said substituents of the said aryl or heteroaryl groups can be substituted by one or more groups selected from halogens, pseudohalogens, $C_1$–$C_3$-alkyl, $C_1$–$C_3$-alkoxy, and $CF_3$; where with respect to the group $R_5$ which can be an aryl or a heteroaryl group, a heteroaryl group is generally preferred over an aryl group, and said heteroaryl group can be unsubstituted or substituted and carry at least one of the substituents mentioned above in the definition relating to $R^5$;

$R^6$ is H, $C_1$–$C_6$-alkyl or benzyl;

$R^7$ is selected from the group consisting of:
H; $C_1$–$C_6$-alkyl which can be phenyl-substituted; phenyl; indanyl; and heteroaryl; and wherein each of the aforementioned aromatic groups can be unsubstituted or carry one or more substituents from the group consisting of halogens, pseudohalogens, $C_1$–$C_3$-alkyl, $C_1$–$C_3$-alkoxy and $CF_3$;

$R^8$ is H or $C_1$–$C_6$-alkyl;

$R^9$ is $C_1$–$C_6$-alkyl which can be unsubstituted or carry one or more substituents from the group consisting of: F; di($C_1$–$C_3$-alkyl)amino; and unsubstituted and at least monosubstituted phenyl and heteroaryl, the substituents of which are selected from the group consisting of $C_1$–$C_3$-alkyl, $C_1$–$C_3$-alkoxy, halogens, pseudohalogens, and $CF_3$;

$R^{10}$ independently has the same meaning as $R^7$;

$R^{11}$ independently has the same meaning as $R^8$;

$R^{12}$ independently has the same meaning as $R^6$;

$R^{13}$ is selected from the group consisting of: H; $C_1$–$C_6$-alkyl; and unsubstituted and substituted phenyl, benzyl, heteroaryl, phenyl-CO, and heteroaryl-CO, the substituents of which are selected from the group consisting of halogens, pseudohalogens, $C_1$–$C_3$-alkyl, $C_1$–$C_3$-alkoxy, and $CF_3$, and wherein one or more of these substituents can be present;

$R^{14}$ is H or $C_1$–$C_6$-alkyl;

$R^{15}$ is selected from the group consisting of: H; $C_1$–$C_6$-alkyl; and substituted and unsubstituted benzyl, phenyl and heteroaryl, the substituents of which are selected from the group consisting of halogens, pseudohalogens, $C_1$–$C_3$-alkyl, $C_1$–$C_3$-alkoxy, and $CF_3$, and wherein one or more of these substituents can be present;

$R^{16}$ is selected from the group consisting of: —$C_1$–$C_6$-alkyl; $CF_3$; and substituted and unsubstituted phenyl and heteroaryl, the substituents of which are selected from the group consisting of halogens, pseudohalogens, $C_1$–$C_3$-alkyl, $C_1$–$C_3$-alkoxy, and $CF_3$, and wherein one or more of these substitutents can be present;

$R^{17}$ independently has the same meaning as $R^7$;
$R^{18}$ independently has the same meaning as $R^8$;
$R^{19}$ independently has the same meaning as $R^{16}$;
$R^{20}$ independently has the same meaning as $R^{16}$;
$R^{21}$ independently has the same meaning as $R^6$;
$R^{22}$ independently has the same meaning as $R^7$;
$R^{23}$ independently has the same meaning as $R^8$;
$R^{24}$ independently has the same meaning as $R^7$;
$R^{25}$ independently has the same meaning as $R^8$;

heteroaryl is a 5 to 10-membered, mono- or bicyclic aromatic heterocycle containing one or more heteroatoms from the group consisting of N, O, and S;

aryl is phenyl, naphth-1-yl or naphth-2-yl;

m is 0, 1 or 2, with the proviso that, in case $R^1$, $R^2$, $R^3$ and $R^4$ are hydrogen, $R^5$ is not phenyl, 5-chloro-2-ethoxyphenyl, 5-chloro-2-methoxyphenyl, 5-bromo-2-methoxyphenyl, 5-fluoro-2-methoxyphenyl, 2-methoxy-5-methylphenyl, 3-alkylcarbonylamino-2-hydroxyphenyl or unsubstituted or substituted 4-oxoquinolinyl; and that, in case $R^5$ is phenyl, A is not CHOH; and that, in case $R^5$ is phenyl, $R^1$ is not hydroxy or methoxy; and that, in case $R^5$ is phenyl, $R^2$ is not Br, hydroxy or methoxy; and that, in case $R^5$ is 3-pyridyl, $R^2$ is not hydroxy.

The compounds according to general formula (I) and their precursors can be prepared according to methods published in the literature or, respectively, analogous methods. Appropriate methods have been published in, for example, Windaus; Chem. Ber. 57 (1924) 1735, Cannon, J. G. et al, J. Med. Chem. 17 (1974) 565, Itoh, K. et al., Chem. Pharm. Bull. 25 (1977) 2917, Hillver et al, J. Med. Chem. 33 (1990) 1541, Copinga et al., J. Med. Chem. 36 (1993) 2891 and Trillat et al., Eur. J. Med. Chem. Chim. Ther. 33 (1998) 437. 1,2,3,4-Tetrahydronaphthyl amines prepared according to the disclosed methods can be dissolved in a solvent such as, for example, dichloromethane, THF, toluene or dioxane and reacted in the presence of base such as, for example, triethylamine, with an appropriate carboxylic acid derivative, for example, a carboxylic acid chloride. This reaction is preferably carried out at room temperature.

Alternatively, the compounds according to the general formula (I) are obtained by a coupling reaction of the respective 1,2,3,4-tetrahydronaphthyl amines with an acid, which 1,2,3,4-tetrahydronaphthyl amines and/or acid may be substituted and/or functionalized, in the presence of a base like, for example, diisopropylethylamine, and the use of an appropriate coupling reagent like, for example, carbodiimides, HATU or TOTU. The thus obtained acyl 1,2,3,4-tetrahydronaphthyl amines can then be functionalized, in order to obtain further desired compounds according to the general formula (I). The reaction leading to the above-mentioned acyl 1,2,3,4-tetrahydronaphthyl amines and the reactions used in the functionalization are known to the person skilled in the art.

All reactions for the synthesis of the compounds of the formula (I) are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a compound of the formula (I), it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the compounds of the formula (I) can be purified by customary purification procedures, for example by recrystallization or chromatography. The starting compounds for the preparation of the compounds of the formula (I) are commercially available or can be prepared according to or analogously to literature procedures. The compounds obtained with the above-mentioned synthesis methods are a further object of the present invention.

Some of the compounds falling under formula (I) and their use as pharmaceutical agents are disclosed in the literature.

EP-A 0 253 257 discloses various acylated 1,2,3,4-tetrahydronaphthyl amines falling under the general formula I and their use as precursors for the synthesis of pharmacologically active compounds.

EP-A 0 420 064 discloses the use of various compounds according to the general formula I for therapeutic and diagnostic purposes like insomnia and psychic diseases. The treatment of cardiovascular diseases is not disclosed. Compounds disclosed by EP-A 0 420 064 include 2-amidotetralin derivatives of the general formula (II).

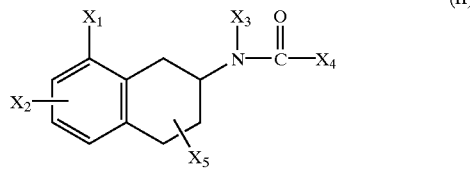

(II)

In the above formula, $X_1$–$X_5$ have the following meaning:

$X_1$ is hydrogen, halogen, amino, amido, a $C_{1-4}$ alkyl, alkoxyl, or alkoxylaryl;

$X_2$ is hydrogen, hydroxyl, halogen, amino, amido, aryl, mono- or di-$C_{1-4}$ alkylamino, $C_{1-4}$ alkylaryl, or alkoxylaryl, or $C_{1-4}$ alkyl, alkenyl, alkynl, alkoxyl;

$X_3$ is hydrogen, aryl, $C_{1-4}$ alkylaryl, or $C_{1-4}$ alkyl, alkenyl, or alkynl;

$X_4$ is aryl, $C_{1-4}$ alkylaryl, or $C_{1-4}$ alkyl, haloalkyl, or cycloalkyl;

$X_5$ is hydrogen, hydroxyl, halogen, oxo, aryl, $C_{1-4}$ alkylaryl, or $C_{1-4}$ alkyl;

wherein aryl substitutents of $X_2$, $X_3$, $X_4$ and $X_5$ may optionally be halogen, hydroxyl, amino, mono- or di-$C_{1-4}$ alkylamino, or $C_{1-4}$ alkyl or alkoxyl substituted, provided that when $X_1$ is methoxy, and $X_2$, $X_3$, and $X_5$ are hydrogen, $X_4$ is not methyl.

Compounds explicitly disclosed by EP-A 0 420 064 are not an object of the present invention.

WO 00/51970 discloses compounds according to the general formula (III) and their use for the potentiation of cholinergic activity.

$$Z^1\!\!\diagdown\!\!\underset{Z^2\!\!\diagup}{X}\!\!-\!Y\!-\!Q\!-\!Z^3$$

(III)

In the above formula:

$Z^1$ and $Z^2$ are each aryl or ar(lower)alkyl, or are taken together to form lower alkylene or lower alkenylene, each of which may be substituted with aryl or may be condensed with a cyclic hydrocarbon optionally substituted with lower alkyl, lower alkoxy, aryl, aryloxy or halogen, $Z^3$ is lower alkyl, lower alkoxy, aryl, arylamino or aryloxy, each of which may be substituted with lower alkoxy or halogen, pyridyl, or pyridylamino, X is CH or N, Y is a single bond or —NH—, and Q is

Referring to the definition of $Z^1$ and $Z^2$ in formula (III), it is stated that preferred lower alkylenes are tetramethylene or pentamethylene, preferred lower alkenylenes are butenylene, pentenylene or methylpentenylene, a preferred cyclic hydrocarbon is benzene and a preferred aryl is phenyl.

Furthermore, it is stated that, among other preferred compounds according to the general formula (III) are those having lower alkenylene which may be substituted with aryl or may be condensed with benzene optionally substituted with lower alkoxy for $Z^1$ and $Z^2$ to be taken together to form, aryl or arylamino, each of which may be substituted with halogen, pyridyl, or pyridylamino for $Z^3$, CH or N for X, a single bond or —NH— for Y, and

for Q.

More preferred compounds according to the general formula (III) are those having $Z^1$ and $Z^2$ taken together to form methylpentenylene, butenylene condensed with benzene or pentenylene which may be condensed with benzene optionally substituted with lower alkoxy.

As examples, there are provided 2-(4-fluorobenzoylamino)-1,2,3,4,-tetrahydronaphthalene, 2-(pyridin-4-ylcarbonylamino)-1,2,3,4-tetrahydronaphthalene, (R)-4-fluoro-N-(1,2,3,4tetrahydronaphthalen-2-yl)-benzamide, (S)-4-fluoro-N-(1,2,3,4-tetrahydronaphthalen-2-yl)-benzamide, 4-fluoro-N-(7-methoxy-1,2,3,4-tetrahydronaphthalen-2-yl)-benzamide and 4-fluoro-N-(6-methoxy-1,2,3,4-tetrahydronaphthalen-2-yl)-benzamide.

Compounds explicitly disclosed by WO 00/51970 are not an object of the present invention.

The object of the present invention is furthermore attained by the use of acylated 1,2,3,4-tetrahydronaphthyl amines according to the general formula (I) in any of their stereoisomeric forms or mixtures thereof in any ratio or the pharmaceutically acceptable salts thereof for the manufacture of a medicament for the stimulation of the expression of endothelial NO-synthase.

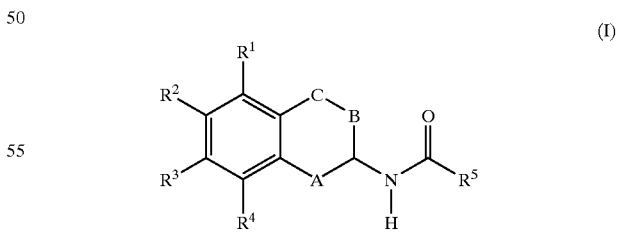

(I)

In the above formula, $R^1$ and $R^4$ are independently from each other selected from the group consisting of:

H; unsubstituted and at least monosubstituted $C_1$–$C_{10}$-alkyl, $C_2$–$C_{10}$-alkenyl and $C_2$–$C_{10}$-alkynyl, the substituents of which are selected from the group consisting of F, OH, $C_1$–$C_8$-alkoxy, ($C_1$–$C_8$-alkyl)mercapto, CN, COOR$^6$, CONR$^7$R$^8$, and unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; $R^9$CO; CONR$^{10}$R$^{11}$; COOR$^{12}$; $CF_3$; halogens; pseudohalogens; NR$^{13}$R$^{14}$; OR$^{15}$; S(O)$_m$R$^{16}$; SO$_2$NR$^{17}$R$^{18}$; and NO$_2$;

$R^2$ and $R^3$ are independently from each other selected from the group consisting of:

H; halogens; pseudohalogens; unsubstituted and at least monosubstituted $C_1$–$C_{10}$-alkyl the substituents of which are selected from the group consisting of OH, phenyl, and heteroaryl; OH; $C_1$–$C_{10}$-alkoxy; phenoxy; S(O)$_m$R$^{19}$; $CF_3$; CN; NO$_2$; ($C_1$–$C_{10}$-alkyl)amino; di($C_1$–$C_{10}$-alkyl) amino; ($C_1$–$C_6$-alkyl)-CONH—; unsubstituted and at least monosubstituted phenyl-CONH— and phenyl-SO$_2$—O—, the substituents of which are selected from the group consisting of halogens, pseudohalogens, $CH_3$ and methoxy; ($C_1$–$C_6$-alkyl)SO$_2$—O—; unsubstituted and at least monosubstituted ($C_1$–$C_6$-alkyl)CO, the substituents of which are selected from the group consisting of F, di($C_1$–$C_3$-alkyl)amino, pyrrolidinyl and piperidinyl; and phenyl-CO, the phenyl part of which can be substituted by one or more substituents from the group consisting of $C_1$–$C_3$-alkyl, halogens and methoxy;

A is selected from the group consisting of $CH_2$, CHOH and CH—($C_1$–$C_3$-alkyl);

B is selected from the group consisting of $CH_2$ and CH—($C_1$–$C_3$-alkyl);

C independently has the same meaning as B;

$R^5$ is a group Ar or a group Hetar both of which can be unsubstituted or carry one or more substituents selected from the group consisting of: halogens; pseudohalogens; NH$_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, ($C_1$–$C_{10}$-alkyl)amino, di($C_1$–$C_{10}$-alkyl)amino, the substituents of which are selected from the group consisting of F, OH, $C_1$–$C_8$-alkoxy, aryloxy, ($C_1$–$C_8$-alkyl)mercapto, NH$_2$, ($C_1$–$C_8$-alkyl)amino, and di($C_1$–$C_8$-alkyl)amino; $C_3$–$C_5$-alkandiyl; phenyl; heteroaryl; aryl- or heteroaryl-substituted $C_1$–$C_4$-alkyl; $CF_3$; NO$_2$; OH; phenoxy; benzyloxy; ($C_1$–$C_{10}$-alkyl)COO; S(O)$_m$R$^{20}$; SH; phenylamino; benzylamino; ($C_1$–$C_{10}$-alkyl)-CONH—; ($C_1$–$C_{10}$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_{10}$-alkyl)-CO; phenyl-CO; heteroaryl-CO; $CF_3$—CO; —OCH$_2$O—; —OCF$_2$O—; —OCH$_2$CH$_2$O—; —CH$_2$CH$_2$O—; COOR$^{21}$; CONR$^{22}$R$^{23}$; CNH(NH$_2$); SO$_2$NR$^{24}$R$^{25}$; R$^{26}$SO$_2$NH—; R$^{27}$SO$_2$N($C_1$–$C_6$-alkyl)-; and saturated or at least monounsaturated aliphatic, mononuclear 5- to 7-membered heterocycles containing 1 to 3 heteroatoms selected from the group consisting of N, O and S, which heterocycles can be substituted by one or more substituents selected from the group consisting of halogens, $C_1$–$C_3$-alkyl, $C_1$–$C_3$-alkoxy, OH, oxo and $CF_3$, where said heterocycles can optionally be condensed to the said group Ar or the said group Hetar; wherein all aryl, heteroaryl, phenyl, aryl-containing, heteroaryl-containing and phenyl-containing groups, which are optionally present in the said substituents of the said group Ar or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^6$ is selected from the group consisting of:

H; $C_1$–$C_{10}$-alkyl, which can be substituted by one or more substituents selected from the group consisting of F, $C_1$–$C_8$-alkoxy, and di($C_1$–$C_8$-alkyl)amino; aryl-($C_1$–$C_4$-alkyl) and heteroaryl-($C_1$–$C_4$-alkyl), which can be substituted by one or more substituents selected from the group consisting of halogens, $C_1$–$C_4$-alkoxy, and di($C_1$–$C_6$-alkyl)amino;

$R^7$ is selected from the group consisting of:

H; $C_1$–$C_{10}$-alkyl which can be substituted by one or more substituents selected from the group consisting of F, $C_1$–$C_8$-alkoxy, di($C_1$–$C_8$-alkyl)amino and phenyl; phenyl; indanyl;

and heteroaryl; and wherein each of the aforementioned aromatic groups can be unsubstituted or carry one or more substituents from the group consisting of halogens, pseudohalogens, $C_1$–$C_3$-alkyl, $C_1$–$C_3$-alkoxy and $CF_3$;

$R^8$ is H or $C_1$–$C_{10}$-alkyl;

$R^9$ is selected from the group consisting of: $C_1$–$C_{10}$-alkyl which can be unsubstituted or carry one or more substituents from the group consisting of: F, ($C_1$–$C_4$)-alkoxy, di($C_1$–$C_3$-alkyl)amino; and unsubstituted and at least monosubstituted phenyl and heteroaryl, the substituents of which are selected from the group consisting of $C_1$–$C_3$-alkyl, $C_1$–$C_3$-alkoxy, halogens, pseudohalogens, and $CF_3$;

$R^{10}$ independently has the same meaning as $R^7$;

$R^{11}$ independently has the same meaning as $R^8$;

$R^{12}$ independently has the same meaning as $R^6$;

$R^{13}$ is selected from the group consisting of: H; $C_1$–$C_6$-alkyl; unsubstituted and substituted phenyl, benzyl, heteroaryl, ($C_1$–$C_6$-alkyl)-CO, phenyl-CO, and heteroaryl-CO, the substituents of which are selected from the group consisting of halogens, pseudohalogens, $C_1$–$C_3$-alkyl, $C_1$–$C_3$-alkoxy, and $CF_3$, and wherein one or more of these substituents can be present;

$R^{14}$ independently has the same meaning as $R^{13}$;

$R^{15}$ is selected from the group consisting of: H; $C_1$–$C_{10}$-alkyl; ($C_1$–$C_3$-alkoxy)-$C_1$–$C_3$-alkyl; and substituted and unsubstituted benzyl, phenyl and heteroaryl, the substituents of which are selected from the group consisting of halogens, pseudohalogens, $C_1$–$C_3$-alkyl, $C_1$–$C_3$-alkoxy, and $CF_3$, and wherein one or more of these substituents can be present;

$R^{16}$ is selected from the group consisting of: $C_1$–$C_{10}$-alkyl which can be substituted by one or more substituents selected from the group consisting of F, OH, $C_1$–$C_8$-alkoxy, aryloxy, ($C_1$–$C_8$-alkyl)mercapto, ($C_1$–$C_8$-alkyl)amino and di($C_1$–$C_8$-alkyl)amino; $CF_3$; and substituted and unsubstituted phenyl and heteroaryl, the substituents of which are selected from the group consisting of halogens, pseudohalogens, $C_1$–$C_3$-alkyl, $C_1$–$C_3$-alkoxy and $CF_3$, and wherein one or more of these substitutents can be present;

$R^{17}$ independently has the same meaning as $R^7$;

$R^{18}$ independently has the same meaning as $R^8$;

$R^{19}$ independently has the same meaning as $R^{16}$;

$R^{20}$ independently has the same meaning as $R^{16}$;

$R^{21}$ independently has the same meaning as $R^6$;

$R^{22}$ independently has the same meaning as $R^7$;

$R^{23}$ independently has the same meaning as $R^8$;

$R^{24}$ independently has the same meaning as $R^7$;

$R^{25}$ independently has the same meaning as $R^8$;

$R^{26}$ independently has the same meaning as $R^{16}$;

$R^{27}$ independently has the same meaning as $R^{16}$;

heteroaryl is a 5 to 10-membered, aromatic, mono- or bicyclic heterocycle containing one or more heteroatoms selected from the group consisting of N, O, and S;

the group Hetar is a 5 to 10-membered, aromatic, mono- or bicyclic heterocycle containing one or more heteroatoms selected from the group consisting of N, O, and S;

aryl is phenyl, naphth-1-yl or naphth-2-yl;
the group Ar is phenyl, naphth-1-yl or naphth-2-yl; and
m is 0, 1 or 2.

Furthermore, with respect to the definitions given above in the context of the compounds according to the general formula (I) for use in the manufacture of a medicament, the same explanations as laid out above in the context with the compounds as such apply.

In preferred embodiments, the object of the present invention is attained by the use of acylated 1,2,3,4-tetrahydronaphthyl amines according to the general formula (I) in any of their stereoisomeric forms or mixtures thereof in any ratio or the pharmaceutically acceptable salts thereof for the manufacture of a medicament for the stimulation of the expression of endothelial NO-synthase, wherein the substituents $R^1$ to $R^5$, A, B and C and the groups aryl and heteroaryl of the formula (I) independently from each other have the following meanings. Hence, one or more of the substituents $R^1$ to $R^5$ and A, B and C can have the preferred, the more preferred, the even more preferred, the most preferred or particularly preferred meanings specified below.

$R^1$ is preferably selected from the group consisting of: H; $C_1$–$C_4$-alkyl; $C_1$–$C_4$-alkoxy; $CF_3$; halogens; pseudohalogens; $(C_1$–$C_4$-alkyl)-$S(O)_m$—; and unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$, where heteroaryl is selected from the group consisting of 5- and 6-membered heterocycles containing one or more heteroatoms selected from the group consisting of N, O, and S; $R^1$ is more preferably H, halogen or $C_1$–$C_4$-alkyl.

$R^2$ is preferably selected from the group consisting of: H; halogens; pseudohalogens; and $C_1$–$C_3$-alkyl; $R_2$ is more preferably H.

$R^3$ is preferably selected from the group consisting of: H; halogens; pseudohalogens; and $C_1$–$C_3$-alkyl; $R^3$ is more preferably H.

$R^4$ is preferably selected from the group consisting of: H; $C_1$–$C_4$-alkyl; $C_1$–$C_4$-alkoxy; $CF_3$; halogens; pseudohalogens; $(C_1$–$C_4$-alkyl)-$S(O)_m$—; and unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$, where heteroaryl is selected from the group consisting of 5- and 6-membered heterocycles containing one or more heteroatoms selected from the group consisting of N, O, and S; $R^4$ is more preferably H, halogen or $C_1$–$C_4$-alkyl; $R^4$ is most preferably H.

$R^1$ to $R^4$ are in particular each H.

A is preferably selected from the group consisting of $CH_2$ and CHOH; A is in particular $CH_2$.

B and C are preferably independently from each other selected from the group consisting of $CH_2$ and CH—$CH_3$; more preferably B is a $CH_2$ unit while C is $CH_2$ or CH—$CH_3$; most preferably B and C are $CH_2$.

$R^5$ is preferably selected from the group consisting of: a group Ar or a group Hetar both of which can be unsubstituted or carry one or more substituents selected from the group consisting of: halogens; CN; $NH_2$; unsubstituted and at least monosubstituted $C_1$–$C_8$-alkyl, $C_2$–$C_8$-alkenyl, $C_2$–$C_8$-alkynyl, $C_1$–$C_8$-alkoxy, $(C_1$–$C_8$-alkyl)amino, di($C_1$–$C_8$-alkyl)amino, the substituents of which are selected from the group consisting of F, $C_1$–$C_6$-alkoxy, phenoxy, $(C_1$–$C_6$-alkyl)mercapto, $NH_2$, $(C_1$–$C_6$-alkyl)amino, and di($C_1$–$C_6$-alkyl)amino; $C_3$–$C_5$-alkandiyl; phenyl; heteroaryl; phenyl- or heteroaryl-substituted $C_1$–$C_2$-alkyl; $CF_3$; OH; phenoxy; benzyloxy; $(C_1$–$C_6$-alkyl)COO; $S(O)_m$ $(C_1$–$C_6$)-alkyl; $S(O)_m$-phenyl; $S(O)_m$-heteroaryl; SH; phenylamino; benzylamino; $(C_1$–$C_6$-alkyl)-CONH—; $(C_1$–$C_6$-alkyl)-CON($C_1$–$C_4$-alkyl)-; phenyl-CONH—; phenyl-CON$(C_1$–$C_4$-alkyl)-; heteroaryl-CONH—; heteroaryl-CON$(C_1$–$C_4$-alkyl)-; $(C_1$–$C_6$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; $COO(C_1$–$C_6$-alkyl); —$CONH_2$; —$CONH(C_1$–$C_6$-alkyl)$; —$CON(di(C_1$–$C_6$-alkyl))$; $CNH(NH_2)$; —$SO_2NH_2$; —$SO_2NH(C_1$–$C_6$-alkyl)$; —$SO_2NH(phenyl)$; —$SO_2N(di(C_1$–$C_6$-alkyl))$; $(C_1$–$C_6$-alkyl)$SO_2NH$—; $(C_1$–$C_6$-alkyl)$SO_2N(C_1$–$C_6$-alkyl)-; phenyl-$SO_2NH$—; phenyl-$SO_2N(C_1$–$C_6$-alkyl)-; heteroaryl-$SO_2NH$—; heteroaryl-$SO_2N(C_1$–$C_6$-alkyl)-; and saturated or at least monounsaturated aliphatic, mononuclear 5- to 7-membered heterocycles containing 1 to 3 heteroatoms selected from the group consisting of N, O, and S, which heterocycles can be substituted by one or more substituents selected from the group consisting of halogens, $C_1$–$C_3$-alkyl, $C_1$–$C_3$-alkoxy, OH, oxo and $CF_3$, where said heterocycles can optionally be condensed to the said group Ar or the said group Hetar; wherein all heteroaryl, phenyl, heteroaryl-containing and phenyl-containing groups, which are optionally present in the said substituents of the said group Ar or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^5$ is more preferably selected from the group consisting of: phenyl or a group Hetar both of which can be unsubstituted or carry one or more substituents selected from the group consisting of: halogens; CN; $NH_2$; unsubstituted and at least monosubstituted $C_1$–$C_6$-alkyl, $C_2$–$C_6$-alkenyl, $C_2$–$C_6$-alkynyl, $C_1$–$C_3$-alkoxy, $(C_1$–$C_4$-alkyl)amino, di($C_1$–$C_4$-alkyl)amino, the substituents of which are selected from the group consisting of F, $C_1$–$C_3$-alkoxy, $(C_1$–$C_3$-alkyl)mercapto, and $NH_2$; $C_3$–$C_5$-alkandiyl; phenyl; heteroaryl; phenyl- or heteroaryl-substituted $C_1$–$C_2$-alkyl; $CF_3$; OH; $(C_1$–$C_4$-alkyl)COO; $S(O)(C_1$–$C_4)$-alkyl; $(C_1$–$C_4$-alkyl)-CONH—; $(C_1$–$C_4$-alkyl)-CON($C_1$–$C_4$-alkyl)-; $(C_1$–$C_4$-alkyl)-CO; phenyl-CO; heteroaryl-CO; $CF_3$—CO; —$OCH_2O$—; —$OCF_2O$—; —$OCH_2CH_2OO$—; —$CH_2CH_2O$—; $COO(C_1$–$C_6$-alkyl); —$CONH_2$; —$CONH(C_1$–$C_4$-alkyl)$; —$CON(di(C_1$–$C_4$-alkyl))$; $CNH(NH_2)$; —$SO_2NH_2$; —$SO_2NH(C_1$–$C_4$-alkyl)$; —$SO_2NH(phenyl)$; —$SO_2N(di(C_1$–$C_4$-alkyl))$; $(C_1$–$C_4$-alkyl)$SO_2NH$—; $(C_1$–$C_4$-alkyl)$SO_2N(C_1$–$C_4$-alkyl)-; and saturated or at least monounsaturated aliphatic, mononuclear 5- to 7-membered heterocycles containing 1 to 3 heteroatoms selected from the group consisting of N, O, and S, which heterocycles can be substituted by one or more substituents selected from the group consisting of halogens, $C_1$–$C_3$-alkyl, $C_1$–$C_3$-alkoxy, OH, oxo and $CF_3$, where said heterocycles can optionally be condensed to the said phenyl or the said group Hetar; wherein all heteroaryl, phenyl, heteroaryl-containing and phenyl-containing groups, which are optionally present in the said substituents of the said phenyl or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^5$ is even more preferably selected from the group consisting of: phenyl or a group Hetar both of which can be unsubstituted or carry one or more substituents selected from the group consisting of: F; Cl; Br; $C_1$–$C_3$-alkyl; Cl—$C_3$-alkoxymethyl; 2-amino-3,3,3-trifluoropropyl; $CF_3$; $C_3$–$C_5$-alkandiyl; phenyl; heteroaryl; benzyl; heteroarylmethyl; OH; $C_1$–$C_3$-alkoxy; phenoxy; trifluoromethoxy; 2,2,2-trifluoroethoxy; $(C_1$–$C_4$-alkyl)COO; $(C_1$–$C_3$-alkyl) mercapto; phenylmercapto; $(C_1$–$C_3$-alkyl)sulfonyl;

phenylsulfonyl; $NH_2$; ($C_1$–$C_4$-alkyl)amino; di($C_1$–$C_4$-alkyl) amino; ($C_1$–$C_3$-alkyl)-CONH—; ($C_1$–$C_3$-alkyl)-$SO_2$NH—; ($C_1$–$C_3$-alkyl)-CO; phenyl-CO; —$OCH_2O$—; —$OCF_2O$—; —$CH_2CH_2O$—; COO($C_1$–$C_4$-alkyl); —$CONH_2$; —CONH ($C_1$–$C_4$-alkyl); —CON(di($C_1$–$C_4$-alkyl)); CN; —$SO_2NH_2$; —$SO_2$NH($C_1$–$C_4$-alkyl); —$SO_2$N(di($C_1$–$C_4$-alkyl)); pyrrolidinyl; piperidinyl; morpholinyl; and thiomorpholinyl; wherein all heteroaryl, phenyl, heteroaryl-containing and phenyl-containing groups, which are optionally present in the said substituents of the said phenyl or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^5$ is most preferably selected from the group consisting of: 4-fluorophenyl, 4-chlorophenyl, 4-bromophenyl, 4-($C_1$–$C_3$-alkoxy)-phenyl, 4-trifluoromethoxyphenyl, 2-bromo-4-fluorophenyl, 2-chloro-4-fluorophenyl, 3,4-dimethylphenyl, 2,4-dimethylphenyl, 4-chloro-2-methylphenyl, 2-hydroxy-4-methylphenyl, 2-hydroxy-4-ethoxyphenyl, 2-methoxy-4-methylphenyl, 4-phenoxyphenyl, 3-fluoro-4-methylphenyl, benzo[1,3]dioxol-5-yl, 2,2-difluoro-benzo[1,3]dioxol-5-yl, 2,3-dihydrobenzofuran-5-yl, 1-(4-chloro-phenyl)-5-trifluoromethyl-1H-pyrazole-4-yl, 1-(4-fluoro-phenyl)-3,5-dimethyl-1H-pyrazole-4-yl, 1H-benzotriazole-5-yl, 1H-indole-4-yl, 1H-indole-6-yl, 1-isopropyl-2-trifluoromethyl-1H-benzoimidazole-5-yl, 1-methyl-3-oxo-1,2,3,4-tetrahydro-quinoxaline-6-yl, 1-phenyl-5-trifluoromethyl-1H-pyrazole-4-yl, 2-(2-hydroxy-pyridin-4-yl)-1H-benzoimidazole-5-yl, 2-(4-cyano-phenyl)-1H-benzoimidazole-5-yl, 2,4-dimethyl-oxazole-5-yl, 2,4-dimethyl pyrimidine-5-yl, 2,4-dimethyl-thiazole-5-yl, 2,5-dimethyl-1H-pyrrole-3-yl, 2,5-dimethyl-1-phenyl-1H-pyrrole-3-yl, 2,5-dimethyl-1pyridin-4-ylmethyl-1H-pyrrolyl, 2,5-dimethyl-2H-pyrazole-3-yl, 2,6-dichloro-pyrid-3-yl, 2,6-dimethoxy-pyrid-3-yl, 2,6-dimethyl-pyrid-3-yl, 2-amino-4,6-dimethyl-pyrid-3-yl, 2-amino-6-chloro-pyrid-3-yl, 2-amino-pyrid-3-yl, 2-chloro-6-methyl-pyrid-3-yl, 2-chloro-pyrid-4-yl, 2-cyclopropyl-4-methyl-thiazole-5-yl, 2-dimethylamino-4-methyl-thiazole-5-yl, 2-dimethylamino-pyrid-4-yl, 2-ethyl-5-methyl-2H-pyrazole-3-yl, 2-hydroxy-6-methyl-pyrid-3-yl, 2-methyl-IH-benzoimidazole-5-yl, 2-methyl-3H-benzoimidazole-5-yl, 2-methyl-pyrid-3-yl, 2-methyl-6-trifluoromethyl-pyrid-3-yl, 2-methyl-thiazole-5-yl, 2-morpholin-4-yl-pyridin-4-yl, 2-morpholin-4-yl-pyrimidine-5-yl, 2-pyrrolidin-1-yl-pyridin-4-yl, 3,5-dimethyl-1H-pyrazole-4-yl, 3-amino-5,6-dimethyl-pyrazine-2-yl, 3-amino-5-methyl-pyrazine-2-yl, 3-amino-pyrazine-2-yl, 3-dimethylamino-4-methyl-phenyl, 3-dimethylamino-phenyl, 3H-benzoimidazole-5-yl, 1H-benzoimidazole-5-yl, 3-methanesulfonylaininio-2-methyl-phenyl, 3-methanesulfonylamino-phenyl, 3-methyl-isoxazole-4-yl, 3-morpholin-4-yl-phenyl, 3-piperidin-1-yl-phenyl, 3-pyrrolidin-1-yl-phenyl, 4-(2,2,2-trifluoro-ethoxy)-phenyl, 4,6-dimethyl-pyrid-3-yl, 4-amino-2-ethylsulfanyl-pyrimidine-5-yl, 4-amino-2-methyl-pyrimidine-5-yl, 4-chloro-3-methanesulfonylamino-phenyl, 4-chloro-3-sulfamoyl-phenyl, 4-methyl-3-methylamino-phenyl, 4-methyl-thiazole-5-yl, pyridine-2-yl, pyridine-3-yl, pyridine-4-yl, 5-thiophen-2-yl-pyrid-3-yl, 2-methyl-4-trifluoromethyl-thiazol-5-yl, 5,6,7,8-tetrahydro-quinoline-3-yl, 5-amino-1-phenyl-1H-pyrazole-4-yl, 5-methanesulfonyl-2-methyl-phenyl, 5-methyl-1-phenyl-1H-pyrazole-4-yl, 5-methyl-isoxazole-3-yl, 5-methyl-pyrid-3-yl, 5-methyl-pyrazine-2-yl, 6-chloro-pyrid-3-yl, 6-cyano-pyrid-3-yl, 6-dimethylamino-pyrid-3-yl, 6-ethynyl-pyrid-3-yl, 6-methoxymethyl-pyrid-3-yl, 6-methoxy-pyrid-3-yl, 6-methyl-2-methylamino-pyrid-3-yl, 6-methylamino-pyrazine-2-yl, 6-methyl-pyrid-3-yl, 6-morpholin-4-yl-pyrid-3-yl, 6-pyrrolidin-1-yl-pyrid-3-yl, imidazo[1,2-a]pyridine-2-yl, 6-trifluoromethyl-pyrid-3-yl, and pyrimidine-4-yl.

Heteroaryl is preferably a 5 to 10-membered, aromatic, mono- or bicyclic heterocycle containing one, two or three heteroatoms selected from the group consisting of N, O, and S; heteroaryl is most preferably selected from the group consisting of: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzthiazolyl, benzoxazolyl, quinolinyl, isoquinolinyl, quinoxalinyl, quinazolyl, indolyl, benzofaranyl, benzothiophenyl, and indazolyl.

The group Hetar is preferably a 5 to 10-membered, aromatic, mono- or bicyclic heterocycle containing one, two or three heteroatoms selected from the group consisting of N, O and S; the group Hetar is most preferably selected from the group consisting of. furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl.

Aryl is preferably phenyl.

m is preferably 0 or 2.

Compounds of the formula (I) used for the manufacture of a medicament for the stimulation of the expression of endothelial NO-synthase, in which one or more, including all of the above-mentioned groups have the preferred meanings, the more preferred meanings, the even more preferred meanings, the most preferred meanings or the particularly preferred meanings defined above are also an object of the present invention.

In a further embodiment, the object of the present invention is attained by compounds of the formula (I) in any of their stereoisomeric forms or mixtures thereof in any ratio or the pharmaceutically acceptable salts thereof used for the manufacture of a medicament for the stimulation of the expression of endothelial NO-synthase wherein the substituents $R^1$ to $R^5$, A, B and C and the groups aryl and heteroaryl have the following meanings.

$R^1$ and $R^4$ are independently from each other selected from the group consisting of:

H; unsubstituted and at least monosubstituted $C_1$–$C_{10}$-alkyl, $C_2$–$C_{10}$-alkenyl and $C_2$–$C_{10}$-alkynyl, the substituents of which are selected from the group consisting of F, OH, $C_1$–$C_6$-alkoxy, ($C_1$–$C_6$-alkyl)mercapto, CN, $COOR^6$, $CONR^7R^8$, unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; $R^9CO$; $CONR^{10}R^{11}$; $COOR^{12}$; $CF_3$; halogens; pseudohalogens; $NR^{13}R^{14}OR^{15}$; $S(O)_mR^{16}$; $SO_2NR^{17}R^{18}$; and $NO_2$;

$R^2$ and $R^3$ are independently from each other selected from the group consisting of:

H; halogens; pseudohalogens; unsubstituted and at least monosubstituted $C_1$–$C_6$-alkyl. the substituents of which are selected from the group consisting of OH, phenyl, and heteroaryl; OH; $C_1$–$C_6$-alkoxy; phenoxy; $S(O)_mR^{19}$; $CF_3$; CN; $NO_2$; ($C_1$–$C_6$-alkyl)amino; di($C_1$–$C_6$-alkyl)amino; ($C_1$–$C_6$-alkyl)-CONH—; unsubstituted and at least monosubstituted phenyl-CONH and phenyl-$SO_2$—O—, the substituents of which are selected from the group consisting of halogens, pseudohalogens, $CH_3$ and methoxy; $(C_1-C_6\text{-alkyl})SO_2$—O—; unsubstituted and at least monosubstituted $(C_1-C_6\text{-alkyl})CO$, the substituents of which are selected from the group consisting of F, $di(C_1-C_3\text{-alkyl})amino$, pyrrolidinyl and piperidinyl; and phenyl-CO, the phenyl part of which can be substituted by one or more substituents from the group consisting of $C_1-C_3\text{-alkyl}$, halogens and methoxy;

A is $CH_2$, CHOH or CH—$(C_1-C_3\text{-alkyl})$;

B is $CH_2$ or CH—$(C_1-C_3\text{-alkyl})$;

C independently has the same meaning as B;

$R^5$ is an aryl or a heteroaryl group which can be unsubstituted or carry one or more substituents selected from the group consisting of: halogens; pseudohalogens; $C_1-C_{10}$-alkyl; $C_3-C_5$-alkandiyl; phenyl; phenyl substituted $C_1-C_4$-alkyl; $CF_3$; OH; $C_1-C_{10}$-alkoxy; phenoxy; benzyloxy; $CF_3O$; $(C_1-C_{10}\text{-alkyl})COO$; $S(O)_mR^{20}$; $(C_1-C_{10}\text{-alkyl})amino$; $di(C_1-C_{10}\text{-alkyl})amino$; $(C_1-C_{10}\text{-alkyl})\text{-}CONH$—; $(C_1-C_{10}\text{-alkyl})\text{-}CON(C_1-C_3\text{-alkyl})$-; $(C_1-C_{10}\text{-alkyl})\text{-}CO$; $CF_3$—CO; —$OCH_2O$—; —$OCF_2O$—; —$OCH_2CH_2O$—; —$CH_2CH_2O$—; phenylamino; phenyl-CO; $COOR^{21}$; $CONR^{22}R^{23}$; $SO_2NR^{24}R^{25}$; and aromatic or aliphatic, mononuclear 5- to 7-membered heterocycles containing 1 to 3 heteroatoms from the group consisting of N, O, and S which can be substituted by one ore more substituents from the group consisting of halogens, $C_1-C_3$-alkyl, $C_1-C_3$-alkoxy and $CF_3$; wherein all phenyl groups and phenyl-containing groups which may be present in the said substituents of the said aryl or heteroaryl groups can be substituted by one or more groups selected from halogens, pseudohalogens, $C_1-C_3$-alkyl, $C_1-C_3$-alkoxy, and $CF_3$; where with respect to the group $R^5$ which can be an aryl or a heteroaryl. group, a heteroaryl group is generally preferred over an aryl group, and said heteroaryl group can be unsubstituted or substituted and carry at least one of the substituents mentioned above in the definition relating to $R^5$;

$R^6$ is H, $C_1-C_6$-alkyl or benzyl;

$R^7$ is selected from the group consisting of:

H; $C_1-C_6$-alkyl which can be phenyl-substituted; phenyl; indanyl; and heteroaryl; and wherein each of the aforementioned aromatic groups can be unsubstituted or carry one or more substituents from the group consisting of halogens, pseudohalogens, $C_1-C_3$-alkyl, $C_1-C_3$-alkoxy and $CF_3$;

$R^8$ is H or $C_1-C_6$-alkyl;

$R^9$ is $C_1-C_6$-alkyl which can be unsubstituted or carry one or more substituents from the group consisting of: F; $di(C_1-C_3\text{-alkyl})amino$; and unsubstituted and at least monosubstituted phenyl and heteroaryl, the substituents of which are selected from the group consisting of $C_1-C_3$-alkyl, $C_1-C_3$-alkoxy, halogens, pseudohalogens, and $CF_3$;

$R^{10}$ independently has the same meaning as $R^7$;

$R^{11}$ independently has the same meaning as $R^8$;

$R^{12}$ independently has the same meaning as $R^6$;

$R^{13}$ is selected from the group consisting of: H; $C_1-C_6$-alkyl; and unsubstituted and substituted phenyl, benzyl, heteroaryl, phenyl-CO, and heteroaryl-CO, the substituents of which are selected from the group consisting of halogens, pseudohalogens, $C_1-C_3$-alkyl, $C_1-C_3$-alkoxy, and $CF_3$, and wherein one or more of these substituents can be present;

$R^{14}$ is H or $C_1-C_6$-alkyl;

$R^{15}$ is selected from the group consisting of: H; $C_1-C_6$-alkyl; and substituted and unsubstituted benzyl, phenyl and heteroaryl, the substituents of which are selected from the group consisting of halogens, pseudohalogens, $C_1-C_3$-alkyl, $C_1-C_3$-alkoxy, and $CF_3$, and wherein one or more of these substituents can be present;

$R^{16}$ is selected from the group consisting of: $C_1-C_6$-alkyl; $CF_3$; and substituted and unsubstituted phenyl and heteroaryl, the substituents of which are selected from the group consisting of halogens, pseudohalogens, $C_1-C_3$-alkyl, $C_1-C_3$-alkoxy, and $CF_3$, and wherein one or more of these substitutents can be present;

$R^{17}$ independently has the same meaning as $R^7$;

$R^{18}$ independently has the same meaning as $R^8$;

$R^{19}$ independently has the same meaning as $R^{16}$;

$R^{20}$ independently has the same meaning as $R^{16}$;

$R^{21}$ independently has the same meaning as $R^6$;

$R^{22}$ independently has the same meaning as $R^7$;

$R^{23}$ independently has the same meaning as $R^8$;

$R^{24}$ independently has the same meaning as $R^7$;

$R^{25}$ independently has the same meaning as $R^8$;

heteroaryl is a 5 to 10-membered, mono- or bicyclic aromatic heterocycle containing one or more heteroatoms from the group consisting of N, O, and S;

aryl is phenyl, naphth-1-yl or naphth-2-yl;

m is 0, 1 or 2.

The compounds according to the general formula (I) can be used to upregulate the expression of the endothelial NO synthase and are helpful pharmaceutical compounds for the treatment of various diseases. In the context of the present invention, treatment includes the therapy as well as the prophylaxis of the respective diseases.

Examples of diseases which can be treated with the compounds according to the present invention include cardiovascular diseases like stable and unstable angina pectoris, coronary heart disease, Prinzmetal angina (spasm), acute coronary syndrome, heart failure, myocardial infarction, stroke, thrombosis, peripheral artery occlusive disease (PAOD), endothelial dysfunction, atherosclerosis, restenosis, endothelial damage after PTCA, hypertension including essential hypertension, pulmonary hypertension, and secondary hypertension (renovascular hypertension, chronic glomerulonephritis), erectile dysfunction, ventricular arrhythmia, and the lowering of cardiovascular risk of postmenopausal women or after intake of contraceptives.

Compounds of the formula (I) can additionally be used in the therapy and prophylaxis of diabetes and diabetes complications (nephropathy, retinopathy), angiogenesis, asthma bronchiale, chronic renal failure, cirrhosis of the liver, osteoporosis, restricted memory performance or a restricted ability to learn.

Preferred indications are stable angina pectoris, coronary heart disease, hypertension, endothelial dysfunction, atherosclerosis and diabetes complications.

The compounds according to the formula (I) can also be used in combination with other pharmaceutically active compounds, preferably compounds which are able to enhance the effect of the compounds according to the general formula (I). Examples of such compounds include: statins; ACE-inhibitors; AT1-antagonists; argininase-inhibitors; PDE V-inhibitors; Ca-antagonists; alpha-blockers; beta-blockers; metimazol and analogous compounds; arginine; tetrahydrobiopterin; vitamins, in particular vitamin C and vitamin B6; and niacin.

The compounds of the formula (I) and their pharmaceutically acceptable salts, optionally in combination with other pharmaceutically active compounds, can be administered to animals, preferably to mammals, and in particular to humans, as pharmaceuticals by themselves, in mixtures with one another or in the form of pharmaceutical preparations. Further subjects of the present invention therefore also are the compounds of the formula (I) and their pharmaceutically acceptable salts for use as pharmaceuticals, their use as transcription stimulating agent for endothelial NO synthase and in particular their use in the therapy and prophylaxis of the above-mentioned syndromes as well as their use for preparing medicaments for these purposes. Furthermore, subjects of the present invention are pharmaceutical preparations (or pharmaceutical compositions) which comprise an effective dose of at least one compound of the formula (I) and/or a pharmaceutically acceptable salt thereof and a pharmaceutically acceptable carrier, i.e. one or more pharmaceutically acceptable carrier substances and/or additives.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of compounds of the formula (I) and/or its pharmaceutically acceptable salts in the pharmaceutical preparations normally ranges from 0.2 to 800 mg, preferably from 0.5 to 500 mg, in particular from 1 to 200 mg, per dose, but depending on the type of the pharmaceutical preparation it may also be higher. The pharmaceutical preparations usually comprise 0.5 to 90 percent by weight of the compounds of the formula (I) and/or their pharmaceutically acceptable salts. The preparation of the pharmaceutical preparations can be carried out in a manner known per se. To this end, one or more compounds of the formula (I) and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formula (I) and their pharmaceutically acceptable salts and to use the resulting lyophilizates, for example, for preparing preparations for injection or infusion. Suitable carriers for microcapsules, implants or rods are, for example, copolymers of glycolic acid and lactic acid.

Besides the compound or compounds according to the invention and carriers, the pharmaceutical preparations can also contain additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formula (I) to be administered and/or of a pharmaceutically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the formula (I). In general, a daily dose of approximately 0.01 to 100 mg/kg, preferably 0.1 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compounds according to the formula (I) can also be used for other purposes than those indicated in the foregoing. Non-limiting examples include diagnostic purposes, use as biochemical tools, and as intermediates for the preparation of further compounds, e.g. pharmaceutically active compounds.

The present invention will now be illustrated in the following examples:

EXAMPLES

General Procedures

Method A 0.5 mmol of the respective tetrahydronaphthyl amine were dissolved in 10 ml 1,2-dichloroethane, 41 µl (0.5 mmol) of pyridine were added, and then 1 ml of a 0.55 molar solution of the respective acid chloride in 1,2-dichloroethane was added at 0° C., followed by stirring over night at RT. The thus-obtained mixture was filtered, washed with 5% NaHCO$_3$— and 5% NaCl-solution, dried over sodium sulfate and concentrated. The thus-obtained residue was fractionated with prep. HPLC (RP18, acetonitrile/water, 0.1% trifluoroacetic acid).

Unless indicated otherwise, the retention times indicated were obtained on an Aglint HP 1100 MSD HPLC-system with an Alltech 33×7 mm EPS C18 100 Å 1.5 µm-column and a water/acetonitrile-gradient (start: 5% H$_2$0/95% of a mixture or H$_2$O and acetonitrile (10:90); 4.25 min: 5% H$_2$0/95% of a mixture or H$_2$O and acetonitrile (10:90); 4.5 min: 5% H$_2$0/95% of a mixture or H$_2$O and acetonitrile (10:90); 5 min: 5% H$_2$0/95% of a mixture or H$_2$O and acetonitrile (10:90) and a flow of 0.75 ml/min.

There were thus obtained:

Ex 1

4-Fluoro-N-(1,2,3,4-tetrahydro-naphth-2-yl)-benzamide

[M+H$^+$] measured: 270.0 retention time: 5.07 min (gradient: from 10% acetonitrile to 90% acetonitrile in 10 min)

Ex 2

(R)-N-(6-Bromo-1,2,3,4-tetrahydro-naphth-2-yl)-4-fluoro-benzamide

[M+H$^+$] measured: 347.9
retention time: 3.26

Ex 3

(S)-N-(6-Bromo-1,2,3,4-tetrahydro-naphth-2-yl)-4-fluoro-benzamide

[M+H$^+$] measured: 347.9
retention time: 3.26

Ex 4

(R)-N-(8-Bromo-1,2,3,4-tetrahydro-naphth-2-yl)-4-fluoro-benzamide

[M+H$^+$] measured: 347.9
retention time: 3.25

Ex 5

(S)-N-(8-Bromo-1,2,3,4-tetrahydro-naphth-2-yl)-4-fluoro-benzamide

[M+H$^+$] measured: 347.9
retention time: 3.25

Ex 6

(R)-N-(5-Methoxy-1,2,3,4-tetrahydro-naphth-2-yl)-4-fluoro-benzamide

[M+H$^+$] measured: 300.0
retention time: 3.12

Ex 7

(S)-N-(5-Methoxy-1,2,3,4-tetrahydro-naphth-2-yl)-4-fluoro-benzamide

[M+H$^+$] measured: 300.0
retention time: 3.12

Ex 8

(S)-N-(7-Methoxy-1,2,3,4-tetrahydro-naphth-2-yl)-4-fluoro-benzamide

[M+H$^+$] measured: 300.0
retention time: 3.11

Ex 9

(R)-N-(8-Methoxy-1,2,3,4-tetrahydro-naphth-2-yl)-4-fluoro-benzamide

[M+H$^+$] measured: 300.0
retention time: 3.13

Method B:

To 0.75 mmol of the respective acid and 271 μl (1.575 mmole) diisopropylethylamine (DIPEA) in 5 ml tetrahydrofuran were added 271 mg (0.825 mmol) O-[(cyanoethoxycarbonylmethylene)-amino]-N,N,N',N'-tetramethyluronium tetrafluoroborate (TOTU) (dissolved in 1 ml DMF). After 15 min stirring at room temperature a mixture of 168 mg (0.900 mmol), 2-amino-1,2,3,4-tetrahydronaphthalene hydrochloride in the form of the R- or S-enantiomer and 172 μl (1.000 mmol) DIPEA in 1 ml DMF was added. After stirring for 6 h the mixture was filtered and evaporated. The residue was taken up in ethyl acetate and washed successively with 20 ml 1 n HCL and 20 ml 5% sodium hydrogencarbonate solution. The resulting organic phase was evaporated and purified via prep. HPLC. (RP 18, Acetonitrile/Water).

The chromatographic conditions (HPLC) were as follows: LiChroCart 55-2, PuroSpher STAR; RP 18 e (MERCK), solvent A: acetonitrile/water (90:10)+0.5% formic acid; solvent B: acetonitrile/water (10:90)+0.5% formic acid; gradient: 95% B 0.5 min, 95% B to 5% B in 1.75 min, 5% B 2.5 min; 1 ml/min.

Ex 10

3-Dimethylamino-N-(R)-1,2,3,4-tetrahydro-naphthalen-2-yl-benzamide

[M+H$^+$] measured: 295
retention time: 3.020

Ex 11

3-Dimethylamino-N-(S)-1,2,3,4-tetrahydro-naphthalen-2-yl-benzamide

[M+H$^+$] measured: 295
retention time: 3.02

Ex 12

3-Amino-pyrazine-2-carboxylic acid N-(R)-(1,2,3,4-tetrahydro-naphthalen-2-yl)-amide (salt with formic acid)

[M+H$^+$] measured: 269
retention time: 3.03

Ex 13

3-Amino-pyrazine-2-carboxylic acid N-(S)-(1,2,3,4-tetrahydro-naphthalen-2-yl)-amide (salt with formic acid)

[M+H$^+$] measured: 269
retention time: 3.03

Ex 14

6-Chloro-N-(R)-1,2,3,4-tetrahydro-naphthalen-2-yl-nicotinamide (salt with formic acid)

[M+H$^+$] measured: 287
retention time: 2.98

Ex 15

6-Chloro-N-(S)-1,2,3,4-tetrahydro-naphthalen-2-yl-nicotinamide (salt with formic acid)

[M+H$^+$] measured: 287
retention time: 2.99

Ex 16

2-Hydroxy-6-methyl-N-(S)-1,2,3,4-tetrahydro-naphthalen-2-yl-nicotinamide (salt with formic acid)

[M+H$^+$] measured: 283
Rf-value: 2.80

Ex 17

2-Amino-N-(R)-1,2,3,4-tetrahydro-naphthalen-2-yl-nicotinamide (salt with formic acid)

[M+H$^+$] measured: 283
retention time: 2.480

Ex 18

2-Amino-N-(S)-1,2,3,4-tetrahydro-naphthalen-2-yl-nicotinamide (salt with formic acid)

[M+H$^+$] measured: 268
retention time: 2.50

Ex 19

6-Methyl-N-(R)-1,2,3,4-tetrahydro-naphthalen-2-yl-nicotinamide

[M+H$^+$] measured: 267
retention time: 2.61

Ex 20

6-Methyl-N-(S)-1,2,3,4-tetrahydro-naphthalen-2-yl-nicotinamide

[M+H$^+$] measured: 267
retention time: 2.63

Ex 21

1H-Indole-4-carboxylic acid-N-(R)-(1,2,3,4-tetrahydro-naphthalen-2-yl)-amide

[M+H$^+$] measured: 291
retention time: 2.963

Ex 22

1H-Indole-4-carboxylic acid-N-(S)-(1,2,3,4-tetrahydro-naphthalen-2-yl)-amide

[M+H$^+$] measured: 291
retention time: 2.97

Ex 23

1H-Benzoimidazole-5-carboxylic acid N-(R)-(1,2,3,4-tetrahydro-naphthalen-2-yl)-amide

[M+H$^+$] measured: 292
retention time: 2.523

Ex 24

1H-Benzoimidazole-5-carboxylic acid N-(S)-(1,2,3,4-tetrahydro-naphthalen-2-yl)-amide

[M+H$^+$] measured: 292
retention time: 2.54

Ex 25

1H-Benzotriazole-5-carboxylic acid N-(R)-(1,2,3,4-tetrahydro-naphthalen-2-yl)-amide

[M+H$^+$] measured: 293
retention time: 2.806

Ex 26

1H-Benzotriazole-5-carboxylic acid N-(S)-(1,2,3,4-tetrahydro-naphthalen-2-yl)-amide

[M+H$^+$] measured: 293
retention time: 2.78

Ex 27

2-Methyl-N-(R)-1,2,3,4-tetrahydro-naphthalen-2-yl-nicotinamide; salt with formic acid

[M+H$^+$] measured: 267
retention time: 2.509

Ex 28

2-Methyl-N-(S)-1,2,3,4-tetrahydro-naphthalen-2-yl-nicotinamide

[M+H$^+$] measured: 267
retention time: 2.46

Ex 29

2,4-Dimethyl-thiazole-5-carboxylic acid N-(R)-(1,2,3,4-tetrahydro-naphthalen-2-yl)-amide

[M+H$^+$] measured: 287
retention time: 2.920

Ex 30

2,4-Dimethyl-thiazole-5-carboxylic acid N-(S)-(1,2,3,4-tetrahydro-naphthalen-2-yl)-amide

[M+H$^+$] measured: 287
retention time: 2.93

Ex 31

5-Methyl-1-phenyl-1H-pyrazole-4-carboxylic acid N-(R)-(1,2,3,4-tetrahydro-naphthalen-2-yl)-amide

[M+H$^+$] measured: 332
retention time: 3.065

Ex 32

5-Methyl-1-phenyl-1H-pyrazole-4-carboxylic acid N-(S)-(1,2,3,4-tetrahydro-naphthalen-2-yl)-amide

[M+H$^+$] measured: 332
retention time: 3.08

Ex 33

1-(4-Chloro-phenyl)-5-trifluoromethyl-1H-pyrazole-4-carboxylic acid N-(R)-(1,2,3,4-tetrahydro-naphthalen-2-yl)-amide

[M+H$^+$] measured: 420
retention time: 3.294

Ex 34

1-(4-Chloro-phenyl)-5-trifluoromethyl-1H-pyrazole-4-carboxylic acid N-(S)-(1,2,3,4-tetrahydro-naphthalen-2-yl)-amide

[M+H$^+$] measured: 420
retention time: 3.28

Ex 35

5-Methyl-pyrazine-2-carboxylic acid N-(R)-(1,2,3,4-tetrahydro-naphthalen-2-yl)-amide (salt with formic acid)

[M+H$^+$] measured: 268
retention time: 2.987

Ex 36

5-Methyl-pyrazine-2-carboxylic acid N-(S)-(1,2,3,4-tetrahydro-naphthalen-2-yl)-amide (salt with formic acid)

[M+H$^+$] measured: 268
retention time: 3.00

Ex 37

2,6-Dimethoxy-N-(R)-1,2,3,4-tetrahydro-naphthalen-2-yl-nicotinamide

[M+H$^+$] measured: 313
retention time: 3.283

Ex 38

2,6-Dimethoxy-N-(S)-1,2,3,4-tetrahydro-naphthalen-2-yl-nicotinamide

[M+H$^+$] measured: 313
retention time: 3.24

Ex 39

2-Chloro-6-methyl-N-(R)-1,2,3,4-tetrahydro-naphthalen-2-yl-nicotinamide (salt with formic acid)

[M+H$^+$] measured: 301
retention time: 2.941

Ex 40

2-Chloro-6-methyl-N-(S)-1,2,3,4-tetrahydro-naphthalen-2-yl-nicotinamide (salt with formic acid)

[M+H$^+$] measured: 301
retention time: 2.97

Ex 41

4-Methyl-2-phenyl-thiazole-5-carboxylic acid N-(R)-(1,2,3,4-tetrahydro-naphthalen-2-yl)-amide

[M+H$^+$] measured: 349
retention time: 3.285

Ex 42

4-Methy)-2-phenyl-thiazole-5-carboxylic acid N-(S)-(1,2,3,4-tetrahydro-naphthalen-2-yl)-amide

[M+H$^+$] measured: 349
retention time: 3.31

Ex 43

2-Amino-4,6-dimethyl-N-(R)-1,2,3,4-tetrahydro-naphthalen-2-yl-nicotinamide

[M+H$^+$] measured: 296
retention time: 2.410

Ex 44

2-Amino-4,6-dimethyl-N-(S)-1,2,3,4-tetrahydro-naphthalen-2-yl-nicotinamide (salt with formic acid)

[M+H$^+$] measured: 296
retention time: 2.40

Ex 45

2-Methyl-4-trifluoromethyl-thiazole-5-carboxylic acid N-(R)-(1,2,3,4-tetrahydro-naphthalen-2-yl)-amide

[M+H$^+$] measured: 341
retention time: 3.076

Ex 46

2-Methyl-4-trifluoromethyl-thiazole-5-carboxylic acid-N-(S)-(1,2,3,4-tetrahydro-naphthalen-2-yl)-amide

[M+H$^+$] measured: 341
retention time: 3.07

Ex 47

5-Trifluoromethyl-thieno[3,2-b]pyridine-6-carboxylic acid-N-(R)-(1,2,3,4-tetrahydro-naphthalen-2-yl)-amide (salt with formic acid)

[M+H$^+$] measured: 377
retention time: 3.083

Ex 48

1H-Indole-6-carboxylic acid N-(R)-(1,2,3,4-tetrahydro-naphthalen-2-yl)-amide

[M+H$^+$] measured: 291
retention time: 2.990

Ex 49

1H-Indole-6-carboxylic acid N-(S)-(1,2,3,4-tetrahydro-naphthalen-2-yl)-amide

[M+H$^+$] measured: 291
retention time: 3.02

Ex 50

N-(R)-1,2,3,4-Tetrahydro-naphthalen-2-yl-6-trifluoromethyl-nicotinamide (salt with formic acid)

[M+H$^+$] measured: 321
retention time: 3.075

Ex 51

N-(S)-1,2,3,4-Tetrahydro-naphthalen-2-yl-6-trifluoromethyl-nicotinamide (salt with formic acid)

[M+H$^+$] measured: 321
Rf-value: 3.09

Ex 52

2-Methyl-1H-benzoimidazole-5-carboxylic acid N-(R)-(1,2,3,4-tetrahydro-naphthalen-2-yl)-amide

[M+H$^+$] measured: 306
retention time: 2.507

Ex 53

2-Methyl-1H-benzoimidazole-5-carboxylic acid N-(S)-(1,2,3,4-tetrahydro-naphthalen-2-yl)-amide

[M+H$^+$] measured: 306
retention time: 2.46

Ex 54

2-Methyl-N-(R)-1,2,3,4-tetrahydro-naphthalen-2-yl-6-trifluoromethyl-nicotinamide (salt with formic acid)

[M+H$^+$] measured: 335
retention time: 3.095

Ex 55

2-Methyl-N-(S)-1,2,3,4-tetrahydro-naphthalen-2-yl-6-trifluoromethyl-nicotinamide (salt with formic acid)

[M+H$^+$] measured: 335
retention time: 3.10

Ex 56

6-Cyano-N-(R)-1,2,3,4-tetrahydro-naphthalen-2-yl-nicotinamide (salt with formic acid)

[M+H$^+$] measured: 278
retention time: 2.946

Ex 57

6-Cyano-N-(S)-1,2,3,4-tetrahydro-naphthalen-2-yl-nicotinamide (salt with formic acid)

[M+H$^+$] measured: 278
retention time: 2.93

Ex 58

3,5-Dimethyl-1H-pyrazole-4-carboxylic acid N-(R)-(1,2,3,4-tetrahydro-naphthalen-2-yl)-amide

[M+H$^+$] measured: 270
retention time: 2.735

Ex 59

3,5-Dimethyl-1H-pyrazole-4-carboxylic acid N-(S)-(1,2,3,4-tetrahydro-naphthalen-2-yl)-amide

[M+H$^+$] measured: 270
retention time: 2.76

Ex 60

1-(4-Methoxy-phenyl)-5-methyl-1H-pyrazole-4-carboxylic acid N-(R)-(1,2,3,4-tetrahydro-naphthalen-2-yl)-amide

[M+H$^+$] measured: 362
retention time: 3.053

Ex 61

1-(4-Methoxy-phenyl)-5-methyl-1H-pyrazole-4-carboxylic acid N-(S)-(1,2,3,4-tetrahydro-naphthalen-2-yl)-amide

[M+H$^+$] measured: 362
retention time: 3.06

Ex 62

N-(R)-1,2,3,4-Tetrahydro-naphthalen-2-yl-5-thiophen-2-yl-nicotinamide

[M+H$^+$] measured: 335
retention time: 3.063

Ex 63

N-(S)-1,2,3,4-Tetrahydro-naphthalen-2-yl-5-thiophen-2-yl-nicotinamide (salt with formic acid)

[M+H$^+$] measured: 335
retention time: 3.08

Ex 64

Benzo[c]isoxazole-3-carboxylic acid N-(R)-(1,2,3,4-tetrahydro-naphthalen-2-yl)-amide

[M+H$^+$] measured: 293
retention time: 3.149

Ex 65

Benzo[c]isoxazole-3-carboxylic acid N-(S)-(1,2,3,4-tetrahydro-naphthalen-2-yl)-amide

[M+H$^+$] measured: 293
retention time: 3.17

Ex 66

1-(3,5-Dichloro-phenyl)-5-propyl-1H-pyrazole-4-carboxylic acid N-(R)-(1,2,3,4-tetrahydro-naphthalen-2-yl)-amide

[M+H$^+$] measured: 429
retention time: 3.558

Ex 67

1-(3,5-Dichloro-phenyl)-5-propyl-1H-pyrazole-4-carboxylic acid N-(S)-(1,2,3,4-tetrahydro-naphthalen-2-yl)-amide

[M+H$^+$] measured: 429
retention time: 3.54

Ex 68

(R)-N-(1,2,3,4-Tetrahydro-naphthalen-2-yl)-isonicotinamide (salt with formic acid)

[M+H$^+$] measured: 335
retention time: 2.695

Ex 69

(S)-N-(1,2,3,4-Tetrahydro-naphthalen-2-yl)-isonicotinamide (salt with formic acid)

[M+H$^+$] measured: 335
retention time: 3.08

Measurement of Activation of eNOS Transcription

Activation of eNOS transcription was measured as described in detail in Li et al. "Activation of protein kinase C alpha and/or epsilon enhances transcription of the human endothelial nitric oxide synthase gene", Mol. Pharmacol. 1998; 53: 630–637. Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with compounds.

All compounds were dissolved in sterile DMSO. A final concentration of 0.5% DMSO in complete medium was allowed. Induction of reporter gene expression in these cells was measured using a standard luciferase assay system (Promega, Cat. No E150) according to the manufacturer's instructions. Luciferase induction in cells incubated with compounds were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. EC50 values of transcription induction ratios as a function of compound concentration were determined graphically.

The effect of compounds on eNOS-transcription was confirmed in a second assay based on eNOS protein detection. Primary human umbilical vein cord endothelial cells (HUVEC) were isolated and cultivated according to standard procedures. Confluent cells were incubated with compounds for 18 h and the effect on eNOS protein expression determined by a quantitative Western blotting procedure. After incubation with the compounds, HUVEC were lyzed in ice-cold lysis buffer containing 10 mM Tris-HCl, pH 8.0, 1% SDS and protease inhibitors. The lyzate was subjected to a standard denaturating polyacrylamid gel electropheresis and blotted to nitrocellulose membranes. Using a specific primary monoclonal antibody (Transduction Laboratories, UK) and alkaline phosphatase labelled secondary antibody (Jackson Labs), a specific eNOS protein band was visualized and quantified based on a chemifluorescence detection method.

The results are shown in the table below

| Compound No: | EC-50 ($\mu$M) |
|---|---|
| 1 | 2.2 |
| 4 | >30 |
| 5 | 10 |
| 6 | 1.5 |
| 7 | 6 |
| 10 | 9.56 |
| 11 | 12.80 |
| 14 | 5.93 |
| 17 | 1.96 |
| 19 | 10.89 |
| 20 | 24.71 |
| 22 | 8.82 |
| 23 | 11.50 |
| 25 | 4.55 |
| 26 | 15.05 |
| 27 | 0.18 |
| 29 | 10.46 |
| 30 | 81.83 |
| 31 | 10.92 |
| 32 | 1.13 |
| 33 | 7.00 |
| 34 | 9.97 |
| 35 | 14.87 |
| 36 | 0.33 |
| 39 | 28.30 |
| 40 | 13.55 |
| 41 | 20.35 |
| 42 | 15.97 |
| 43 | 20.59 |
| 45 | 0.29 |
| 46 | 0.41 |
| 47 | 35.25 |
| 48 | 15.64 |
| 50 | 24.56 |
| 51 | 1.60 |
| 52 | 24.35 |
| 54 | 16.33 |
| 55 | 1.10 |
| 56 | 2.75 |
| 57 | 0.50 |
| 60 | 4.12 |
| 62 | 4.47 |
| 63 | 0.30 |
| 64 | 15.19 |
| 66 | 5.86 |
| 67 | 23.48 |
| 69 | 0.19 |

The effect of the compounds according to the invention can also be investigated in the following animal models. (Animal experiments are performed in accordance to the German animal protection law and to the guidelines for the use of experimental animals as given by the Guide for the Care and Use of Laboratory Animals of the US National Institutes of Health.)

Animals and Treatment (Experiments A–C)

ApoE and eNOS deficient mice (C57BL/6J background, Jackson Laboratory, Bar Harbor, Me.) are used. All animals are 10–12 weeks of age and weigh 22 to 28 g. Three days before surgery mice are divided into 4 groups (apoE control, n=10–12; apoE with test compounds, n=10–12; eNOS control, n=10–12; eNOS with test compounds, n=10–12) and receive either a standard rodent chow (containing 4% fat and 0.001% cholesterol; in the following designated as placebo group) or a standard rodent chow+test compound (10 or 30 mg/kg/d p.o.).

A Anti-hypertensive Effect in ApoE Knockout Mice

Blood-pressure is determined in conscious mice using a computerized tail-cuff system (Visitech Systems, Apex, N.C.). After treatment of ApoE deficient mice and eNOS deficient mice with the test compounds the blood pressure is compared to the results obtained with a placebo treatment.

B Inhibition of Neointima Formation and Atherogenesis (femoral artery cuff)

After a 3 day treatment of ApoE deficient mice with the respective compound, (10 mg/kg/d pressed in chow), animals are anesthetized with an intraperitoneal injection of pentobarbital (60 mg/kg) followed by an intramuscular injection of xylazin (2 mg/kg) and a cuff is placed around the femoral artery as described in Moroi et al.(J Clin Invest. 101:1225–32, 1998). Briefly, the left femoral artery is dissected. A non-occlusive 2.0 mm polyethylene cuff made of PE-50 tubing (inner diameter 0.56 mm, outer diameter 0.965 mm, Becton Dickinson, Mountain View, Calif.) is placed around the artery and tied in place with two 7-0 sutures. The right femoral artery is isolated from the surrounding tissues but a cuff is not placed. Treatment with the respective compound is continued for 14 days after surgery. Then the animals are sacrificed. The aorta are taken for determination of vascular eNOS expressions by quantitative western blotting. Both femoral arteries are harvested, fixed in formalin and embedded in paraffin. 20 cross sections (10 $\mu$m) are cut from the cuffed portion of the left femoral artery and from the corresponding segment of the right artery. Sections are subjected to standard hematoxylin and eosin staining. Morphometric analyses are performed using an image analysis computer program (LeicaQWin, Leica Imaging Systems, Cambridge, GB). For each cross section the area of the lumen, the neointima and the media are determined. To this end, the neointima is defined as the area between the lumen and the internal elastic lamina and the media is defined as the area between the internal and the external elastic lamina. The ratio between the area of the neointima and the area of the media is expressed as the neointima/media ratio. The results obtained in the compound group are compared to those obtained in the placebo group.

C Prevention of Atherosclerotic Plaque Formation in Chronic Treatment

ApoE deficient mice are treated for 16 weeks with the respective compound pressed in chow and finally sacrificed. Aortas are removed from each mouse, fixed in formalin and embedded in paraffin. Plaque formation is measured via lipid lesions formation in the aortas (from aortic arch to diaphragm) and is analyzed by oil red O staining. For quantifying the effect of the respective compound on vascular eNOS expression the femoral arteries are used in this experiment. The results obtained in the compound group are compared to those obtained in the placebo group.

D Improvement of Coronary Function in Diseased ApoE Deficient Mice

Old Male wild-type C57BL/6J mice (Charles River Wiga GmbH, Sulzfeld), and apoE deficient mice (C57BL/6J background, Jackson Laboratory, Bar Harbor, Me.) 6 month of age and weighing 28 to 36 g are used in the experiments. Mice are divided into 3 groups (C57BL/6, n=8; apoE control, n=8; apoE with respective compound, n=8) and receive for 8 weeks either a standard rodent chow (containing 4% fat and 0.001% cholesterol) or a standard rodent chow+respective compound (30 mg/kg/d p.o.).

Mice are anesthetized with sodium pentobarbitone (100 mg/kg i.p.), and the hearts are rapidly excised and placed into ice-cold perfusion buffer. The aorta is cannulated and connected to a perfusion apparatus (HUGO SACHS ELECTRONICS, Freiburg, Germany) which is started immediately at a constant perfusion pressure of 60 min Hg. Hearts are perfused in a retrograde fashion with modified Krebs bicarbonate buffer, equilibrated with 95% $O_2$ and 5% $CO_2$ and maintained at 37.5° C.

A beveled small tube (PE 50) is passed through a pulmonary vein into the left ventricle and pulled through the ventricular wall, anchored in the apex by a fluted end, and connected to a tip-micromanometer (Millar 1.4 French). The left atrium is cannulated through the same pulmonary vein and the heart switched to the working mode with a constant preload pressure of 10 mm Hg and an afterload pressure of 60 mm Hg. Aortic outflow and atrial inflow are continuously measured using ultrasonic flow probes (HSE/Transonic Systems Inc.). Coronary flow is calculated as the difference between atrial flow and aortic flow. All hemodynamic data are digitized at a sampling rate of 1000 Hz and recorded with a PC using specialized software (HEM, Notocord).

Hearts are allowed to stabilize for 30 min. All functional hemodynamic data are measured during steady state, and during volume- and pressure loading.

Left ventricular function curves are constructed by varying pre-load pressure. For acquisition of preload curves, afterload is set at 60 mm Hg and preload is adjusted in 5 mm Hg steps over a range of 5 to 25 mm Hg. Hearts are allowed to stabilize at baseline conditions between pressure- and volume-loading.

We claim:
1. An acylated 1,2,3,4-tetrahydronaphthyl amine according to the general formula (I) in any of its stereoisomeric forms or a mixture thereof in any ratio or a pharmaceutically acceptable salt thereof

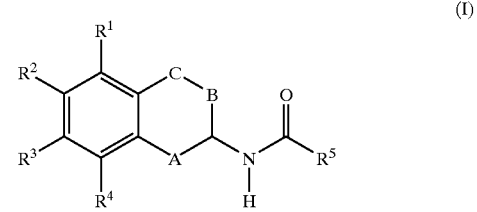

(I)

wherein $R^1$ and $R^4$ are independently of each other chosen from:
H; unsubstituted and at least monosubstituted $C_1$–$C_{10}$-alkyl, $C_2$–$C_{10}$-alkenyl and $C_2$–$C_{10}$-alkynyl, the substituents of which are chosen from F, OH, $C_1$–$C_8$-alkoxy, ($C_1$–$C_8$-alkyl)mercapto, CN, $COOR^6$, $CONR^7R^8$, and unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; $R^9CO$; $CONR^{10}R^{11}$; $COOR^{12}$; $CF_3$; halogens; pseudohalogens; $NR^{13}R^{14}$; $OR^{15}$; $S(O)_mR^{16}$; $SO_2NR^{17}R^{18}$; and $NO_2$;

$R_2$ and $R_3$ are independently of each chosen from:
H; halogens; pseudohalogens; unsubstituted and at least monosubstituted $C_1$–$C_{10}$-alkyl the substituents of which are chosen from OH, phenyl, and heteroaryl; OH; $C_1$–$C_{10}$-alkoxy; phenoxy; $S(O)_mR^{19}$; $CF_3$; CN; $NO_2$; ($C_1$–$C_{10}$-alkyl)amino; di($C_1$–$C_{10}$-alkyl)amino; ($C_1$–$C_6$-alkyl)-CONH—; unsubstituted and at least monosubstituted phenyl-CONH— and phenyl-$SO_2$—O—, the substituents of which are chosen from halogens, pseudohalogens, $CH_3$ and methoxy; ($C_1$–$C_6$-alkyl)$SO_2$—O—; unsubstituted and at least monosubstituted ($C_1$–$C_6$-alkyl)CO, the substituents of which are chosen from F, di($C_1$–$C_3$-alkyl)amino, pyrrolidinyl and piperidinyl; and phenyl-CO, the phenyl part of which can be substituted by one or more substituents chosen from $C_1$–$C_3$-alkyl, halogens and methoxy;

A is chosen from $CH_2$, CHOH and CH—($C_1$–$C_3$-alkyl);
B is chosen from $CH_2$ and CH—($C_1$–$C_3$-alkyl);
C independently has the same meaning as B;
$R^5$ is a group Hetar which can be unsubstituted or carry one or more substituents chosen from: halogens; pseudohalogens; $NH_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, ($C_1$–$C_{10}$-alkyl)amino, and di($C_1$–$C_{10}$-alkyl)amino, the substituents of which are chosen from F, OH, $C_1$–$C_8$-alkoxy, aryloxy, ($C_1$–$C_8$-alkyl)mercapto, $NH_2$, ($C_1$–$C_8$-alkyl)amino, and di($C_1$–$C_8$-alkyl)amino; $C_3$–$C_5$-alkandiyl; phenyl; heteroaryl; aryl-substituted $C_1$–$C_4$-alkyl; heteroaryl-substituted $C_1$–$C_4$-alkyl; $CF_3$; $NO_2$; OH; phenoxy; benzyloxy; ($C_1$–$C_{10}$-alkyl)COO; $S(O)_mR^{20}$; SH; phenylamino; benzylamino; ($C_1$–$C_{10}$-alkyl)-CONH—; ($C_1$–$C_{10}$-alkyl)-CON($C_1$–$C_4$-alkyl)-; phenyl-CONH—; phenyl-CON($C_1$–$C_4$-alkyl)-; heteroaryl- CONH—; heteroaryl-CON($C_1$–$C_4$-alkyl)-; ($C_1$–$C_{10}$-alkyl)-CO; phenyl-CO; heteroaryl-CO; $CF_3$—CO; —O$CH_2$O—; —O$CF_2$O—; —O$CH_2$$CH_2$O—; —$CH_2$$CH_2$O—; COO$R^{21}$; CON$R^{22}$$R^{23}$; CNH(N$H_2$); S$O_2$N$R^{24}$$R^{25}$; $R^{26}$S$O_2$NH—; $R^{27}$S$O_2$N($C_1$–$C_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said group Hetar; and wherein all aryl, heteroaryl, phenyl, aryl-containing, heteroaryl-containing and phenyl-containing groups, which are optionally present in said substituents of said group Hetar, can be substituted by one or more substituents chosen from halogens, pseudohalogens, $C_1$–$C_3$-alkyl, OH, $C_1$–$C_3$-alkoxy, and $CF_3$;

$R^6$ is chosen from:

H; $C_1$–$C_{10}$-alkyl, which can be substituted by one or more substituents chosen from F, $C_1$–$C_8$-alkoxy, and di($C_1$–$C_8$-alkyl)amino; aryl-($C_1$–$C_4$-alkyl) and heteroaryl-($C_1$–$C_4$-alkyl), which can be substituted by one or more substituents chosen from halogens, $C_1$–$C_4$-alkoxy, and di($C_1$–$C_6$-alkyl)amino;

$R^7$ is chosen from:

H; $C_1$–$C_{10}$-alkyl which can be substituted by one or more substituents, chosen from F, $C_1$–$C_8$-alkoxy, di($C_1$–$C_8$-alkyl)amino and phenyl; phenyl; indanyl; and heteroaryl; and wherein each of the aforementioned aromatic groups can be unsubstituted or carry one or more substituents chosen from halogens, pseudohalogens, $C_1$–$C_3$-alkyl, $C_1$–$C_3$-alkoxy and $CF_3$;

$R^8$ is H or $C_1$–$C_{10}$-alkyl;

$R^9$ is chosen from: $C_1$–$C_{10}$-alkyl which can be unsubstituted or carry one or more substituents chosen from F, ($C_1$–$C_4$)-alkoxy, di($C_1$–$C_3$-alkyl)amino; and unsubstituted and at least monosubstituted phenyl and heteroaryl, the substituents of which are chosen from $C_1$–$C_3$-alkyl, $C_1$–$C_3$-alkoxy, halogens, pseudohalogens, and $CF_3$;

$R^{10}$ independently has the same meaning as $R^7$;

$R^{11}$ independently has the same meaning as $R^8$;

$R^{12}$ independently has the same meaning as $R^6$;

$R^{13}$ is chosen from H; $C_1$–$C_6$-alkyl; unsubstituted and substituted phenyl, benzyl, heteroaryl, ($C_1$–$C_6$-alkyl)-CO, phenyl-CO, and heteroaryl-CO, the substituents of which are chosen from halogens, pseudohalogens, $C_1$–$C_3$-alkyl, $C_1$–$C_3$-alkoxy, and $CF_3$, and wherein one or more of these substituents can be present;

$R^{14}$ independently has the same meaning as $R^{13}$;

$R^{15}$ is chosen from H; $C_1$–$C_{10}$-alkyl; ($C_1$–$C_3$-alkoxy)-$C_1$–$C_3$-alkyl; and substituted and unsubstituted benzyl, phenyl and heteroaryl, the substituents of which are chosen from halogens, pseudohalogens, $C_1$–$C_3$-alkyl, $C_1$–$C_3$-alkoxy, and $CF_3$, and wherein one or more of these substituents can be present;

$R^{16}$ is chosen from $C_1$–$C_{10}$-alkyl which can be substituted by one or more substituents chosen from F, OH, $C_1$–$C_8$-alkoxy, aryloxy, ($C_1$–$C_8$-alkyl)mercapto, ($C_1$–$C_8$-alkyl)amino and di($C_1$–$C_8$-alkyl)amino; $CF_3$, and substituted and unsubstituted phenyl and heteroaryl, the substituents of which are chosen from halogens, pseudohalogens, $C_1$–$C_3$-alkyl, $C_1$–$C_3$-alkoxy and $CF_3$, and wherein one or more of these substituents can be present;

$R^{17}$ independently has the same meaning as $R^7$;

$R^{18}$ independently has the same meaning as $R^8$;

$R^{19}$ independently has the same meaning as $R^{16}$;

$R^{20}$ independently has the same meaning as $R^{16}$;

$R^{21}$ independently has the same meaning as $R^6$;

$R^{22}$ independently has the same meaning as $R^7$;

$R^{23}$ independently has the same meaning as $R^8$;

$R^{24}$ independently has the same meaning as $R^7$;

$R^{25}$ independently has the same meaning as $R^8$;

$R^{26}$ independently has the same meaning as $R^{16}$;

$R^{27}$ independently has the same meaning as $R^{16}$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O, and S; aryl is phenyl, naphth-1-yl or naphth-2-yl;

m is 0, 1 or 2;

with the proviso that, in case $R^1$, $R^2$, $R^3$ and $R^4$ are hydrogen or one of the substituents, $R^1$ $R^2$, $R^3$ or $R^4$ is $C_1$–$C_6$-alkoxy, $R^5$ is not unsubstituted pyridyl or unsubstituted or substituted 4-oxoquinolinyl;

where one of the groups $R^1$ and $R^2$ is hydroxy and the other groups of $R^1$, $R^2$, $R^3$, and $R^4$ are hydrogen, $R^5$ is not unsubstituted pyridyl; and where groups A, B, and C are each $CH^2$, $R^5$ is not 5-nitrofuryl.

2. An acylated 1,2,3,4-tetrahydronaphthyl amine in any of its stereoisomeric forms or a mixture thereof in any ratio or a pharmaceutically acceptable salt thereof according to claim 1, wherein in the formula (I)

$R^1$ is chosen from H; $C_1$–$C_4$-alkyl; $C_1$–$C_4$-alkoxy; $CF_3$; halogens; pseudohalogens; ($C_1$–$C_4$-alkyl)-S(O)$_m$—; and unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$, and wherein heteroaryl is chosen from 5- and 6-membered heterocycles containing one or more heteroatoms chosen from N, O, and S;

$R^2$ and $R^3$ are independently of each other chosen from: H; halogens; pseudohalogens; and $C_1$–$C_3$-alkyl;

$R^4$ independently has the same meaning as $R^1$;

A is chosen from $CH_2$ and CHOH;

B and C are independently of each other chosen from $CH_2$ and CH—$CH_3$;

$R^5$ is a group Hetar which can be unsubstituted or carry one or more substituents chosen from: halogens; CN; $NH_2$; unsubstituted and at least monosubstituted $C_1$–$C_8$-alkyl, $C_2$–$C_8$-alkenyl, $C_2$–$C_8$-alkynyl, $C_1$–$C_8$-alkoxy, ($C_1$–$C_8$-alkyl)amino, and di($C_1$–$C_8$-alkyl)amino, the substituents of which are chosen from F, $C_1$–$C_6$-alkoxy, phenoxy, ($C_1$–$C_6$-alkyl)mercapto, $NH_2$, ($C_1$–$C_6$-alkyl)amino, and di($C_1$–$C_6$-alkyl)amino; $C_3$–$C_5$-alkandiyl; phenyl; heteroaryl; phenyl-substituted $C_1$–$C_2$-alkyl; heteroaryl-substituted $C_1$–$C_2$-alkyl; $CF_3$; OH; phenoxy; benzyloxy; ($C_1$–$C_6$-alkyl)COO; S(O)$_m$($C_1$–$C_6$)-alkyl; S(O)$_m$-phenyl; S(O)$_m$-heteroaryl; SH; phenylamino; benzylamino; ($C_1$–$C_6$-alkyl)-CONH—; ($C_1$–$C_6$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_6$-alkyl)-CO; phenyl-CO; heteroaryl-CO; $CF_3$—

CO; —OCH$_2$O—; —OCF$_2$O—; —OCH$_2$CH$_2$O—; —CH$_2$CH$_2$O—; COO(C$_1$–C$_6$-alkyl); —CONH$_2$; —CONH(C$_1$–C$_6$-alkyl); —CON(di(C$_1$–C$_6$-alkyl)); CNH(NH$_2$); —SO$_2$NH$_2$; —SO$_2$NH(C$_1$–C$_6$-alkyl); —SO$_2$NH(phenyl); —SO$_2$N(di(C$_1$–C$_6$-alkyl)); (C$_1$–C$_6$-alkyl)SO$_2$NH—; (C$_1$–C$_6$-alkyl)SO$_2$N(C$_1$–C$_6$-alkyl)-; phenyl-SO$_2$NH—; phenyl-SO$_2$N(C$_1$–C$_6$-alkyl)-; heteroaryl-SO$_2$NH—; heteroaryl-SO$_2$N(C$_1$–C$_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, C$_1$–C$_3$-alkyl, C$_1$–C$_3$-alkoxy, OH, oxo, and CF$_3$, and wherein said heterocycles can optionally be condensed to said group Hetar; and wherein all heteroaryl, phenyl, heteroaryl-containing and phenyl-containing groups, which are optionally present in said substituents of said group Hetar, can be substituted by one or more substituents chosen from halogens, pseudohalogens, C$_1$–C$_3$-alkyl, OH, C$_1$–C$_3$-alkoxy, and CF$_3$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O and S; and m is 0 or 2.

3. An acylated 1,2,3,4-tetrahydronaphthyl amine in any of its stereoisomeric forms or a mixture thereof in any ratio or a pharmaceutically acceptable salt thereof according to claim 1, wherein in the formula (I)

R$^1$ is H, halogen or C$_1$–C$_4$-alkyl;

R$^2$ and R$^3$ are each H;

R$^4$ independently has the same meaning as R$^1$;

A is CH$_2$;

R$^5$ is a group Hetar which can be unsubstituted or carry one or more substituents chosen from: halogens; CN; NH$_2$; unsubstituted and at least monosubstituted C$_1$–C$_6$-alkyl, C$_2$–C$_6$-alkenyl, C$_2$–C$_6$-alkynyl, C$_1$–C$_3$-alkoxy, (C$_1$–C$_4$-alkyl)amino, and di(C$_1$–C$_4$-alkyl)amino, the substituents of which are chosen from F, C$_1$–C$_3$-alkoxy, (C$_1$–C$_3$-alkyl)mercapto, and NH$_2$; C$_3$–C$_5$-alkandiyl; phenyl; heteroaryl; phenyl-substituted C$_1$–C$_2$-alkyl; heteroaryl-substituted C$_1$–C$_2$-alkyl; CF$_3$; OH; (C$_1$–C$_4$-alkyl)COO; S(O)$_m$(C$_1$–C$_4$)-alkyl; (C$_1$–C$_4$-alkyl)-CONH—; (C$_1$–C$_4$-alkyl)-CON(C$_1$–C$_4$-alkyl)-; (C$_1$–C$_4$-alkyl)-CO; phenyl-CO; heteroaryl-CO; CF$_3$—CO; —OCH$_2$O—; —OCF2O—; —OCH$_2$CH$_2$O—; —CH$_2$CH$_2$O—; COO(C$_1$–C$_6$-alkyl); —CONH$_2$; —CONH(C$_1$–C$_4$-alkyl); —CON(di(C$_1$–C$_4$-alkyl)); CNH(NH$_2$); —SO$_2$NH$_2$; —SO$_2$NH(C$_1$–C$_4$-alkyl); —SO$_2$NH(phenyl); —SO$_2$N(di(C$_1$–C$_4$-alkyl)); (C$_1$–C$_4$-alkyl)SO$_2$NH—; (C$_1$–C$_4$-alkyl)SO$_2$N(C$_1$–C$_4$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, C$_1$–C$_3$-alkyl, C$_1$–C$_3$-alkoxy, OH, oxo and CF$_3$, and wherein said heterocycles can optionally be condensed to said group Hetar; and wherein all heteroaryl, phenyl, heteroaryl-containing and phenyl-containing groups, which are optionally present in said substituents of said group Hetar, can be substituted by one or more substituents chosen from halogens, pseudohalogens, C$_1$–C$_3$-alkyl, OH, C$_1$–C$_3$-alkoxy, and CF$_3$;

heteroaryl is a 5 to 10-membered, aromatic, mono- or bicyclic heterocycle containing one, two or three heteroatoms chosen from N, O, and S;

the group Hetar is a 5 to 10-membered, aromatic, mono- or bicyclic heterocycle containing one, two or three heteroatoms chosen from N, O, and S; and m is 0 or 2.

4. The acylated 1,2,3,4-tetrahydronaphthyl amine in any of its stereoisomeric forms or a mixture thereof in any ratio or a pharmaceutically acceptable salt thereof according to claim 1, wherein in the formula (I)

R$^1$ is H, halogen or C$_1$–C$_4$-alkyl;

R$^2$ and R$^3$ are each H;

R$^4$ independently has the same meaning as R$^1$;

A and B are each CH$_2$;

C is CH$_2$ or CH—CH$_3$;

R$^5$ is a group Hetar which can be unsubstituted or carry one or more substituents chosen from: F; Cl; Br; C$_1$–C$_3$-alkyl; C$_1$–C$_3$-alkoxymethyl; 2-amino-3,3,3-trifluoro-propyl-; CF$_3$; C$_3$–C$_5$-alkandiyl; phenyl; heteroaryl; benzyl; heteroaryl-methyl; OH; C$_1$–C$_3$-alkoxy; phenoxy; trifluoromethoxy; 2,2,2-trifluoroethoxy; (C$_1$–C$_4$-alkyl)COO; (C$_1$–C$_3$-alkyl)mercapto; phenylmercapto; (C$_1$–C$_3$-alkyl)sulfonyl; phenylsulfonyl; NH$_2$; (C$_1$–C$_4$-alkyl)amino; di(C$_1$–C$_4$-alkyl)amino; (C$_1$–C$_3$-alkyl)-CONH—; (C$_1$–C$_3$-alkyl)-SO$_2$NH—; (C$_1$–C$_3$-alkyl)-CO; phenyl-CO; —OCH$_2$O—; —OCF$_2$O—; —CH$_2$CH$_2$O—; COO(C$_1$–C$_4$-alkyl); —CONH$_2$; —CONH(C$_1$–C$_4$-alkyl); —CON(di(C$_1$–C$_4$-alkyl)); CN; —SO$_2$NH$_2$; —SO$_2$NH(C$_1$–C$_4$-alkyl); —SO$_2$N(di(C$_1$–C$_4$-alkyl)); pyrrolidinyl; piperidinyl; morpholinyl; and thiomorpholinyl; and wherein all heteroaryl, phenyl, heteroaryl-containing and phenyl-containing groups, which are optionally present in said substituents of said group Hetar, can be substituted by one or more substituents chosen from halogens, pseudohalogens, C$_1$–C$_3$-alkyl, OH, C$_1$–C$_3$-alkoxy, and CF$_3$;

heteroaryl is chosen from: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzthiazolyl, benzoxazolyl, quinolinyl, isoquinolinyl, quinoxalinyl, quinazolyl, indolyl, benzofuranyl, benzothiophenyl, and indazolyl;

the group Hetar is chosen from: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl.

5. An acylated 1,2,3,4-tetrahydronaphthyl amine according to the general formula (I) in any of its stereoisomeric forms or a mixture thereof in any ratio or a pharmaceutically acceptable salt thereof

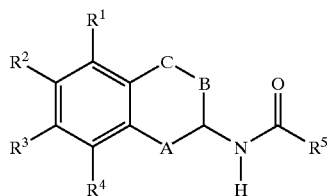

wherein R¹ is H, halogen or $C_1$–$C_4$-alkyl;
R² and R³ are each H;
R⁴ independently has the same meaning as R¹;
A and B are each $CH_2$;
C is $CH_2$ or CH—$CH_3$;
R⁵ is chosen from: benzo[1,3]dioxol-5-yl, 2,2-difluoro-benzo[1,3]dioxol-5-yl, 2,3-dihydrobenzofuran-5-yl, 1-(4-chloro-phenyl)-5-trifluoromethyl-1H-pyrazole-4-yl, 1-(4-fluoro-phenyl)-3,5-dimethyl-1H-pyrazole-4-yl, 1H-benzotriazole-5-yl, 1H-indole-4-yl, 1H-indole-6-yl, 1-isopropyl-2-trifluoromethyl-1H-benzoimidazole-5-yl, 1-methyl-3-oxo-1,2,3,4-tetrahydro-quinoxaline-6-yl, 1-phenyl-5-trifluoromethyl-1H-pyrazole-4-yl, 2-(2-hydroxy-pyridin-4-yl)-1H-benzoimidazole-5-yl, 2-(4-cyano-phenyl)-1H-benzoimidazole-5-yl, 2,4-dimethyl-oxazole-5-yl, 2,4-dimethyl-pyrimidine-5-yl, 2,4-dimethyl-thiazole-5-yl, 2,5-dimethyl-1H-pyrrole-3-yl, 2,5-dimethyl-1-phenyl-1H-pyrrole-3-yl, 2,5-dimethyl-1-pyridin-4-ylmethyl-1H-pyrrolyl, 2,5-dimethyl-2H-pyrazole-3-yl, 2,6-dichloro-pyrid-3-yl, 2,6-dimethoxy-pyrid-3-yl, 2,6-dimethyl-pyrid-3-yl, 2-amino-4,6-dimethyl-pyrid-3-yl, 2-amino-6-chloro-pyrid-3-yl, 2-amino-pyrid-3-yl, 2-chloro-6-methyl-pyrid-3-yl, 2-chloro-pyrid-4-yl, 2-cyclopropyl-4-methyl-thiazole-5-yl, 2-dimethylamino-4-methyl-thiazole-5-yl, 2-dimethylamino-pyrid-4-yl, 2-ethyl-5-methyl-2H-pyrazole-3-yl, 2-hydroxy-6-methyl-pyrid-3-yl, 2-methyl-1H-benzoimidazole-5-yl, 2-methyl-3H-benzoimidazole-5-yl, 2-methyl-pyrid-3-yl, 2-methyl-6-trifluoromethyl-pyrid-3-yl, 2-methyl-thiazole-5-yl, 2-morpholin-4-yl-pyridin-4-yl, 2-morpholin-4-yl-pyrimidine-5-yl, 2-pyrrolidin-1-yl-pyridin-4-yl, 3,5-dimethyl-1H-pyrazole-4-yl, 3-amino-5,6-dimethyl-pyrazine-2-yl, 3-amino-5-methyl-pyrazine-2-yl, 3-amino-pyrazine-2-yl, 3H-benzoimidazole-5-yl, 1H-benzoimidazole-5-yl, 3-methyl-isoxazole-4-yl, 4,6-dimethyl-pyrid-3-yl, 4-amino-2-ethylsulfanyl-pyrimidine-5-yl, 4-amino-2-methyl-pyrimidine-5-yl, 4-methyl-thiazole-5-yl, pyridine-2-yl, pyridine-3-yl, pyridine-4-yl, 5-thiophen-2-yl-pyrid-3-yl, 2-methyl-4-trifluoromethyl-thiazol-5-yl, 5,6,7,8-tetrahydro-quinoline-3-yl, 5-amino-1-phenyl-1H-pyrazole-4-yl, 5-methyl-1-phenyl-1H-pyrazole-4-yl, 5-methyl-isoxazole-3-yl, 5-methyl-pyrid-3-yl, 5-methyl-pyrazine-2-yl, 6-chloro-pyrid-3-yl, 6-cyano-pyrid-3-yl, 6-dimethylamino-pyrid-3-yl, 6-ethynyl-pyrid-3-yl, 6-methoxymethyl-pyrid-3-yl, 6-methoxy-pyrid-3-yl, 6-methyl-2-methylamino-pyrid-3-yl, 6-methylamino-pyrazine-2-yl, 6-methyl-pyrid-3-yl, 6-morpholin-4-yl-pyrid-3-yl, 6-pyrrolidin-1-yl-pyrid-3-yl, imidazo[1,2-a]pyridine-2-yl, 6-trifluoromethyl-pyrid-3-yl, and pyrimidine-4-yl.

6. A method for synthesis of a compound according to claim 1, which method comprises the coupling reaction of the respective 1,2,3,4-tetrahydronaphthyl amine with a respective acid or acid chloride in the presence of an appropriate base and/or an appropriate coupling agent, optionally followed by a functionalization of the thus-obtained compound.

7. A pharmaceutical preparation comprising an effective dose of at least one compound of the formula (I) as defined in claim 1 in any of its stereoisomeric forms or a mixture thereof in any ratio and/or a pharmaceutically acceptable salt thereof and a pharmaceutically acceptable carrier.

8. A pharmaceutical preparation according to claim 7, which pharmaceutical preparation is in the form of a pill, tablet, lacquered tablet, sugar-coated tablet, granule, hard or soft gelatin capsule, aqueous, alcoholic or oily solution, syrup, emulsion or suspension, suppository, solution for injection or infusion, ointment, tincture, spray, transdermal therapeutic systems, nasal spray, aerosol mixture, microcapsule, implant or rod.

9. A method of stimulating the expression of endothelial NO-synthase in a mammal, which method comprises administering said mammal a physiologically active amount of a compound according to the general formula (I) in any of its stereoisomeric forms or a mixture thereof in any ratio or a pharmaceutically acceptable salt thereof

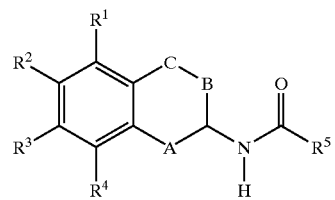

wherein, in the formula (I),
R¹ and R⁴ are independently from each other chosen from:
H; unsubstituted and at least monosubstituted $C_1$–$C_{10}$-alkyl, $C_2$–$C_{10}$-alkenyl and $C_2$–$C_{10}$-alkynyl, the substituents of which are chosen from F, OH, $C_1$–$C_8$-alkoxy, ($C_1$–$C_8$-alkyl)mercapto, CN, $COOR^6$, $CONR^7R^8$, and unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; $R^9CO$; $CONR^{10}R^{11}$; $COOR^{12}$; $CF_3$; halogens; pseudohalogens; $NR^{13}R^{14}$; $OR^{15}$; $S(O)_mR_{16}$; $SO_2NR^{17}R^{18}$; and $NO_2$;
R² and R³ are independently from each other chosen from:
H; halogens; pseudohalogens; unsubstituted and at least monosubstituted $C_1$–$C_{10}$-alkyl the substituents of which are chosen from OH, phenyl, and heteroaryl; OH; $C_1$–$C_{10}$-alkoxy; phenoxy; $S(O)_mR^{19}$; $CF_3$; CN; $NO_2$; ($C_1$–$C_{10}$-alkyl)amino; di($C_1$–$C_{10}$-alkyl)amino; ($C_1$–$C_6$-alkyl)-CONH—; unsubstituted and at least monosubstituted phenyl-CONH— and phenyl-$SO_2$—O—, the substituents of which are chosen from halogens, pseudohalogens, $CH_3$ and methoxy; ($C_1$–$C_6$-alkyl)$SO_2$—O—; unsubstituted and at least monosubstituted ($C_1$–$C_6$-alkyl)CO, the substituents of which are chosen from F, di($C_1$–$C_3$-alkyl)amino, pyrrolidinyl and piperidinyl; and phenyl-CO, the phenyl part of which can be substituted by one or more substituents chosen from $C_1$–$C_3$-alkyl, halogens and methoxy;

A is chosen from $CH_2$, CHOH and CH—($C_1$–$C_3$-alkyl);

B is chosen from $CH_2$ and CH—($C_1$–$C_3$-alkyl);

C independently has the same meaning as B;

$R^5$ is a group Ar or a group Hetar both of which can be unsubstituted or carry one or more substituents chosen from: halogens; pseudohalogens; $NH_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, ($C_1$–$C_{10}$-alkyl)amino, and di($C_1$–$C_{10}$-alkyl)amino, the substituents of which are chosen from F, OH, $C_1$–$C_8$-alkoxy, aryloxy, ($C_1$–$C_8$-alkyl)mercapto, $NH_2$, ($C_1$–$C_8$-alkyl)amino, and di($C_1$–$C_8$-alkyl)amino; $C_3$–$C_5$-alkandiyl; phenyl; heteroaryl; aryl-substituted $C_1$–$C_4$-alkyl; heteroaryl-substituted $C_1$–$C_4$-alkyl; $CF_3$; $NO_2$; OH; phenoxy; benzyloxy; ($C_1$–$C_{10}$-alkyl)COO; $S(O)_m R^{20}$; SH; phenylamino; benzylamino; ($C_1$–$C_{10}$-alkyl)-CONH—; ($C_1$–$C_{10}$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_{10}$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; $COOR^{21}$; $CONR^{22}R^{23}$; $CNH(NH_2)$; $SO_2NR^{24}R^{25}$; $R^{26}SO_2NH$—; $R^{37}SO_2N(C_1$–$C_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said group Ar or said group Hetar; and wherein all aryl, heteroaryl, phenyl, aryl-containing, heteroaryl-containing and phenyl-containing groups, which are optionally present in said substituents of said group Ar or said group Hetar, can be substituted by one or more substituents chosen from halogens, pseudohalogens, $C_1$–$C_3$-alkyl, OH, $C_1$–$C_3$-alkoxy, and $CF_3$;

$R^6$ is chosen from:

H; $C_1$–$C_{10}$-alkyl, which can be substituted by one or more substituents chosen from F, $C_1$–$C_8$-alkoxy, and di($C_1$–$C_8$-alkyl)amino; aryl-($C_1$–$C_4$-alkyl) and heteroaryl-($C_1$–$C_4$-alkyl), which can be substituted by one or more substituents chosen from halogens, $C_1$–$C_4$-alkoxy, and di($C_1$–$C_6$-alkyl)amino;

$R^7$ is chosen from:

H; $C_1$–$C_{10}$-alkyl which can be substituted by one or more substituents chosen from F, $C_1$–$C_8$-alkoxy, di($C_1$–$C_8$-alkyl)amino and phenyl; phenyl; indanyl; and heteroaryl; and wherein each of the aforementioned aromatic groups can be unsubstituted or carry one or more substituents chosen from halogens, pseudohalogens, $C_1$–$C_3$-alkyl, $C_1$–$C_3$-alkoxy and $CF_3$;

$R^8$ is H or $C_1$–$C_{10}$-alkyl;

$R^9$ is chosen from: $C_1$–$C_{10}$-alkyl which can be unsubstituted or carry one or more substituents chosen from: F, ($C_1$–$C_4$)-alkoxy, di($C_1$–$C_3$-alkyl)amino; and unsubstituted and at least monosubstituted phenyl and heteroaryl, the substituents of which are chosen from $C_1$–$C_3$-alkyl, $C_1$–$C_3$-alkoxy, halogens, pseudohalogens, and $CF_3$;

$R^{10}$ independently has the same meaning as $R^7$;

$R^{11}$ independently has the same meaning as $R^8$;

$R^{12}$ independently has the same meaning as $R^6$;

$R^{13}$ is chosen from: H; $C_1$–$C_6$-alkyl; unsubstituted and substituted phenyl, benzyl, heteroaryl, ($C_1$–$C_6$-alkyl)-CO, phenyl-CO, and heteroaryl-CO, the substituents of which are chosen from halogens, pseudohalogens, $C_1$–$C_3$-alkyl, $C_1$–$C_3$-alkoxy, and $CF_3$, and wherein one or more of these substituents can be present;

$R^{14}$ independently has the same meaning as $R^{13}$;

$R^{15}$ is chosen from: H; $C_1$–$C_{10}$-alkyl; ($C_1$–$C_3$-alkoxy)-$C_1$–$C_3$-alkyl; and substituted and unsubstituted benzyl, phenyl and heteroaryl, the substituents of which are chosen from halogens, pseudohalogens, $C_1$–$C_3$-alkyl, $C_1$–$C_3$-alkoxy, and $CF_3$, and wherein one or more of these substituents can be present;

$R^{16}$ is chosen from: $C_1$–$C_{10}$-alkyl which can be substituted by one or more substituents chosen from F, OH, $C_1$–$C_8$-alkoxy, aryloxy, ($C_1$–$C_8$-alkyl)mercapto, ($C_1$–$C_8$-alkyl)amino and di($C_1$–$C_8$-alkyl)amino; $CF_3$; and substituted and unsubstituted phenyl and heteroaryl, the substituents of which are chosen from halogens, pseudohalogens, $C_1$–$C_3$-alkyl, $C_1$–$C_3$-alkoxy and $CF_3$, and wherein one or more of these substitutents can be present;

$R^{17}$ independently has the same meaning as $R^7$;

$R^{18}$ independently has the same meaning as $R^8$;

$R^{19}$ independently has the same meaning as $R^{16}$;

$R^{20}$ independently has the same meaning as $R^{16}$;

$R^{21}$ independently has the same meaning as $R^6$;

$R^{22}$ independently has the same meaning as $R^7$;

$R^{23}$ independently has the same meaning as $R^8$;

$R^{24}$ independently has the same meaning as $R^7$;

$R^{25}$ independently has the same meaning as $R^8$;

$R^{26}$ independently has the same meaning as $R^{16}$;

$R^{27}$ independently has the same meaning as $R^{16}$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O, and S;

aryl is phenyl, naphth-1-yl or naphth-2-yl;

the group Ar is phenyl, naphth-1-yl or naphth-2-yl; and m is 0, 1 or 2.

10. The method according to claim 9, wherein in the formula (I)

$R^1$ is chosen from: H; $C_1$–$C_4$-alkyl; $C_1$–$C_4$-alkoxy; $CF_3$; halogens; pseudohalogens; ($C_1$–$C_4$-alkyl)-$S(O)_m$—; and unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$, and wherein heteroaryl is chosen from 5- and 6-membered heterocycles containing one or more heteroatoms chosen from N, O, and S;

$R^2$ and $R^3$ are independently from each other chosen from: H; halogens; pseudohalogens; and $C_1$–$C_3$-alkyl;

$R^4$ independently has the same meaning as $R^1$;

A is chosen from $CH_2$ and CHOH;

B and C are independently from each other chosen from $CH_2$ and CH—$CH_3$;

$R^5$ is a group Ar or a group Hetar both of which can be unsubstituted or carry one or more substituents chosen from: halogens; CN; $NH_3$; unsubstituted and at least monosubstituted $C_1$–$C_8$-alkyl, $C_2$–$C_8$-alkenyl, $C_2$–$C_8$-alkynyl, $C_1$–$C_8$-alkoxy, ($C_1$–$C_8$-alkyl)amino, and di($C_1$–$C_8$-alkyl)amino, the substituents of which are chosen from F, $C_1$–$C_6$-alkoxy, phenoxy, ($C_1$–$C_6$-alkyl)mercapto, $NH_2$, ($C_1$–$C_6$-alkyl)amino, and di($C_1$–$C_6$-alkyl)amino; $C_3$–$C_5$-alkandiyl; phenyl; heteroaryl; phenyl-substituted $C_1$–$C_2$-alkyl; heteroaryl-substituted $C_1$–$C_2$-alkyl; $CF_3$; OH; phenoxy; benzyloxy; ($C_1$–$C_6$-alkyl)COO; $S(O)_m(C_1$–$C_6)$-alkyl; $S(O)_m$-phenyl; $S(O)_m$-heteroaryl; SH; phenylamino; benzylamino; ($C_1$–$C_6$-alkyl)-CONH—; ($C_1$–$C_6$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_6$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; $COO(C_1$–$C_6$-alkyl); —$CONH_2$; —$CONH(C_1$–$C_6$-alkyl); —$CON(di(C_1$–$C_6$-alkyl));$ $CNH(NH_2)$; —$SO_2NH_2$; —$SO_2NH(C_1$–$C_6$-alkyl); —$SO_2NH(phenyl)$; —$SO_2N(di(C_1$–$C_6$-alkyl));$ ($C_1$–$C_6$-alkyl)$SO_2NH$—; ($C_1$–$C_6$-alkyl)$SO_2N(C_1$–$C_6$-alkyl)-; phenyl-$SO_2NH$—; phenyl-$SO_2N(C_1$–$C_6$-alkyl)-; heteroaryl-$SO_2NH$—; heteroaryl-$SO_2N(C_1$–$C_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said group Ar or said group Hetar; and wherein all heteroaryl, phenyl, heteroaryl-containing and phenyl-containing groups, which are optionally present in said substituents of said group Ar or said group Hetar, can be substituted by one or more substituents chosen from halogens, pseudohalogens, $C_1$–$C_3$-alkyl, OH, $C_1$–$C_3$-alkoxy, and $CF_3$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O, and S;

the group Ar is phenyl, naphth-1-yl or naphth-2-yl; and m is 0 or 2.

11. The method according to claim 9, wherein in the formula (I)

$R^1$ is H, halogen, or $C_1$–$C_4$-alkyl;

$R^2$ and $R^3$ are each H;

$R^4$ independently has the same meaning as $R^1$;

A is $CH_2$;

$R^5$ is phenyl or a group Hetar both of which can be unsubstituted or carry one or more substituents chosen from: halogens; CN; $NH_2$; unsubstituted and at least monosubstituted $C_1$–$C_6$-alkyl, $C_2$–$C_6$-alkenyl, $C_2$–$C_6$-alkynyl, $C_1$–$C_3$-alkoxy, ($C_1$–$C_4$-alkyl)amino, and di($C_1$–$C_4$-alkyl)amino, the substituents of which are chosen from F, $C_1$–$C_3$-alkoxy, ($C_1$–$C_3$-alkyl)mercapto, and $NH_2$; $C_3$–$C_5$-alkandiyl; phenyl; heteroaryl; phenyl-substituted $C_1$–$C_2$-alkyl; heteroaryl-substituted $C_1$–$C_2$-alkyl; $CF_3$; OH; ($C_1$–$C_4$-alkyl)COO; $S(O)_m(C_1$–$C_4)$-alkyl; ($C_1$–$C_4$-alkyl)-CONH—; ($C_1$–$C_4$-alkyl)-CON($C_1$–$C_4$-alkyl)-; ($C_1$–$C_4$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; $COO(C_1$–$C_6$-alkyl); —$CONH_2$; —$CONH(C_1$–$C_4$-alkyl); —$CON(di(C_1$–$C_4$-alkyl));$ $CNH(NH_2)$; —$SO_2NH_2$; —$SO_2NH(C_1$–$C_4$-alkyl); —$SO_2NH(phenyl)$; —$SO_2N(di(C_1$–$C_4$-alkyl));$ ($C_1$–$C_4$-alkyl)$SO_2NH$—; ($C_1$–$C_4$-alkyl)$SO_2N(C_1$–$C_4$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said phenyl or said group Hetar; and wherein all heteroaryl, phenyl, heteroaryl-containing and phenyl-containing groups, which are optionally present in said substituents of said phenyl or said group Hetar, can be substituted by one or more substituents chosen from halogens, pseudohalogens, $C_1$–$C_3$-alkyl, OH, $C_1$–$C_3$-alkoxy, and $CF_3$;

heteroaryl is a 5 to 10-membered, aromatic, mono- or bicyclic heterocycle containing one, two or three heteroatoms chosen from N, O, and S;

the group Hetar is a 5 to 10-membered, aromatic, mono- or bicyclic heterocycle containing one, two or three heteroatoms chosen from N, O, and S; and m is 0 or 2.

12. The method according to claim 9, wherein in the formula (I)

$R^1$ is H, halogen, or $C_1$–$C_4$-alkyl;

$R^2$ and $R^3$ are each H;

$R^4$ independently has the same meaning as $R^1$;

A and B are each $CH_2$;

C is $CH_2$ or $CH$—$CH_3$;

$R^5$ is phenyl or a group Hetar both of which can be unsubstituted or carry one or more substituents chosen from: F; Cl; Br; $C_1$–$C_3$-alkyl; $C_1$–$C_3$-alkoxymethyl; 2-amino-3,3,3-trifluoro-propyl-; $CF_3$; $C_3$–$C_5$-alkandiyl; phenyl; heteroaryl; benzyl; heteroarylmethyl; OH; $C_1$–$C_3$-alkoxy; phenoxy; trifluoromethoxy; 2,2,2-trifluoroethoxy; ($C_1$–$C_4$-alkyl)COO; ($C_1$–$C_3$-alkyl)mercapto; phenylmercapto; ($C_1$–$C_3$-alkyl)sulfonyl; phenylsulfonyl; $NH_2$; ($C_1$–$C_4$-alkyl)amino; di($C_1$–$C_4$-alkyl)amino; ($C_1$–$C_3$-alkyl)-CONH—; ($C_1$–$C_3$-alkyl)-$SO_2NH$—; ($C_1$–$C_3$-alkyl)-CO; phenyl-CO; —$OCH_2O$—; —$OCF_2O$—; —$CH_2CH_2O$—; $COO(C_1$–$C_4$-alkyl); —$CONH_2$; —$CONH(C_1$–$C_4$-alkyl); —$CON(di(C_1$–$C_4$-alkyl));$ CN; —$SO_2NH_2$; —$SO_2NH(C_1$–$C_4$-alkyl); —$SO_2N(di(C_1$–$C_4$-alkyl));$ pyrrolidinyl; piperidinyl; morpholinyl; and thiomorpholinyl; and wherein all heteroaryl, phenyl, heteroaryl-containing and phenyl-containing groups, which are optionally present in said substituents of said phenyl or said group Hetar, can be substituted by one or more substituents chosen from halogens, pseudohalogens, $C_1$–$C_3$-alkyl, OH, $C_1$–$C_3$-alkoxy, and $CF_3$;

heteroaryl is chosen from: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl;

the group Hetar is chosen from: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl.

13. The method according to claim 9, wherein in the formula (I)

$R^1$ is H, halogen or $C_1$–$C_4$-alkyl;

$R^2$ and $R^3$ are each H;

$R^4$ independently has the same meaning as $R^1$;

A and B are each $CH_2$;

C is $CH_2$ or CH—$CH_3$;

$R^5$ is chosen from: 4-fluorophenyl, 4-chlorophenyl, 4-bromophenyl, 4-($C_1$–$C_3$-alkoxy)-phenyl, 4-trifluoromethoxyphenyl, 2-bromo-4-fluorophenyl, 2-chloro-4-fluorophenyl, 3,4-dimethylphenyl, 2,4-dimethylphenyl, 4-chloro-2-methylphenyl, 2-hydroxy-4-methylphenyl, 2-hydroxy-4-ethoxyphenyl, 2-methoxy-4-methylphenyl, 4-phenoxyphenyl, 3-fluoro-4-methylphenyl, benzo[1,3]dioxol-5-yl, 2,2-difluoro-benzo[1,3]dioxol-5-yl, 2,3-dihydrobenzofuran-5-yl, 1-(4-chloro-phenyl)-5-trifluoromethyl-1H-pyrazole-4-yl, 1-(4-fluoro-phenyl)-3,5-dimethyl-1H-pyrazole-4-yl, 1H-benzotriazole-5-yl, 1H-indole-4-yl, 1H-indole-6-yl, 1-isopropyl-2-trifluoromethyl-1H-benzoimidazole-5-yl, 1-methyl-3-oxo-1,2,3,4-tetrahydro-quinoxaline-6-yl, 1-phenyl-5-trifluoromethyl-1H-pyrazole-4-yl, 2-(2-hydroxy-pyridin-4-yl)-1H-benzoimidazole-5-yl, 2-(4-cyano-phenyl)-1H-benzoimidazole-5-yl, 2,4-dimethyl-oxazole-5-yl, 2,4-dimethyl-pyrimidine-5-yl, 2,4-dimethyl-thiazole-5-yl, 2,5-dimethyl-1H-pyrrole-3-yl, 2,5-dimethyl-1-phenyl-1H-pyrrole-3-yl, 2,5-dimethyl-1-pyridin-4-ylmethyl-1H-pyrrolyl, 2,5-dimethyl-2H-pyrazole-3-yl, 2,6-dichloro-pyrid-3-yl, 2,6-dimethoxy-pyrid-3-yl, 2,6-dimethyl-pyrid-3-yl, 2-amino-4,6-dimethyl-pyrid-3-yl, 2-amino-6-chloro-pyrid-3-yl, 2-amino-pyrid-3-yl, 2-chloro-6-methyl-pyrid-3-yl, 2-chloro-pyrid-4-yl, 2-cyclopropyl-4-methyl-thiazole-5-yl, 2-dimethylamino-4-methyl-thiazole-5-yl, 2-dimethylamino-pyrid-4-yl, 2-ethyl-5-methyl-2H-pyrazole-3-yl, 2-hydroxy-6-methyl-pyrid-3-yl, 2-methyl-1H-benzoimidazole-5-yl, 2-methyl-3H-benzoimidazole-5-yl, 2-methyl-pyrid-3-yl, 2-methyl-6-trifluoromethyl-pyrid-3-yl, 2-methyl-thiazole-5-yl, 2-morpholin-4-yl-pyridin-4-yl, 2-morpholin-4-yl-pyrimidine-5-yl, 2-pyrrolidin-1-yl-pyridin-4-yl, 3,5-dimethyl-1H-pyrazole-4-yl, 3-amino-5,6-dimethyl-pyrazine-2-yl, 3-amino-5-methyl-pyrazine-2-yl, 3-amino-pyrazine-2-yl, 3-dimethylamino-4-methyl-phenyl, 3-dimethylamino-phenyl, 3H-benzoimidazole-5-yl, 1H-benzoimidazole-5-yl, 3-methanesulfonylamino-2-methyl-phenyl, 3-methanesulfonylamino-phenyl, 3-methyl-isoxazole-4-yl, 3-morpholin-4-yl-phenyl, 3-piperidin-1-yl-phenyl, 3-pyrrolidin-1-yl-phenyl, 4-(2,2,2-trifluoro-ethoxy)-phenyl, 4,6-dimethyl-pyrid-3-yl, 4-amino-2-ethyl sulfanyl-pyrimidine-5-yl, 4-amino-2-methyl-pyrimidine-5-yl, 4-chloro-3-methanesulfonylamino-phenyl, 4-chloro-3-sulfamoyl-phenyl, 4-methyl-3-methylamino-phenyl, 4-methyl-thiazole-5-yl, pyridine-2-yl, pyridine-3-yl, pyridine-4-yl, 5-thiophen-2-yl-pyrid-3-yl, 2-methyl-4-trifluoromethyl-thiazol-5-yl, 5,6,7,8-tetrahydro-quinoline-3-yl, 5-amino-1-phenyl-1H-pyrazole-4-yl, 5-methanesulfonyl-2-methyl-phenyl, 5-methyl-1-phenyl-1H-pyrazole-4-yl, 5-methyl-isoxazole-3-yl, 5-methyl-pyrid-3-yl, 5-methyl-pyrazine-2-yl, 6-chloro-pyrid-3-yl, 6-cyano-pyrid-3-yl, 6-dimethylamino-pyrid-3-yl, 6-ethynyl-pyrid-3-yl, 6-methoxymethyl-pyrid-3-yl, 6-methoxy-pyrid-3-yl, 6-methyl-2-methylamino-pyrid-3-yl, 6-methylamino-pyrazine-2-yl, 6-methyl-pyrid-3-yl, 6-morpholin-4-yl-pyrid-3-yl, 6-pyrrolidin-1-yl-pyrid-3-yl, imidazo[1,2-a]pyridine-2-yl, 6-trifluoromethyl-pyrid-3-yl, and pyrimidine-4-yl.

14. The method according to claim 9, wherein the mammal is a human.

15. A method of treating a mammal suffering from hypertension wherein the hypertension is chosen from essential hypertension, pulmonary hypertension, secondary hypertension, and renovascular hypertension, which method comprises administering to said mammal a physiologically active amount of a compound according to the general formula (I), in any of its stereoisomeric forms or a mixture thereof in any ratio or a pharmaceutically acceptable salt thereof

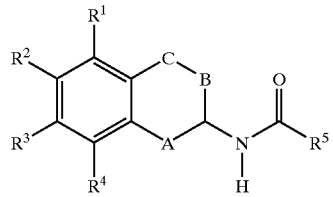

(I)

wherein, in the formula (I), $R^1$ and $R^4$ are independently from each other chosen from:

H; unsubstituted and at least monosubstituted $C_1$–$C_{10}$-alkyl, $C_2$–$C_{10}$-alkenyl and $C_2$–$C_{10}$-alkynyl, the substituents of which are chosen from F, OH, $C_1$–$C_8$-alkoxy, ($C_1$–$C_8$-alkyl)mercapto, CN, $COOR^6$, $CONR^7R^8$, and unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; $R^9CO$; $CONR^{10}R^{11}$; $COOR^{12}$; $CF_3$; halogens; pseudohalogens; $NR^{13}R^{14}$; $OR^{15}$; $S(O)_mR^{16}$; $SO_2NR^{17}R^{18}$; and $NO_2$;

$R^2$ and $R^3$ are independently from each other chosen from:

H; halogens; pseudohalogens; unsubstituted and at least monosubstituted $C_1$–$C_{10}$-alkyl the substituents of which are chosen from OH, phenyl, and heteroaryl; OH; $C_1$–$C_{10}$-alkoxy; phenoxy; $S(O)_mR^{19}$; $CF_3$; CN; $NO_2$; ($C_1$–$C_{10}$-alkyl)amino; di($C_1$–$C_{10}$-alkyl)amino; ($C_1$–$C_6$-alkyl)-CONH—; unsubstituted and at least monosubstituted phenyl-CONH— and phenyl-$SO_2$—O—, the substituents of which are chosen from halogens, pseudohalogens, $CH_3$ and methoxy; ($C_1$–$C_6$-alkyl)$SO_2$—O—; unsubstituted and at least monosubstituted ($C_1$–$C_6$-alkyl)CO, the substituents of which are chosen from F, di($C_1$–$C_3$-alkyl)amino, pyrrolidinyl and piperidinyl; and phenyl-CO, the phenyl part of which can be substituted by one or more substituents chosen from $C_1$–$C_3$-alkyl, halogens and methoxy;

A is chosen from $CH_2$, CHOH and CH—($C_1$–$C_3$-alkyl);

B is chosen from $CH_2$ and CH—($C_1$–$C_3$-alkyl);

C independently has the same meaning as B;

$R^5$ is a group Ar or a group Hetar both of which can be unsubstituted or carry one or more substituents chosen from: halogens; pseudohalogens; $NH_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, ($C_1$–$C_{10}$- alkyl)amino, and di($C_1$–$C_{10}$-alkyl)amino, the substituents of which are chosen from F, OH, $C_1$–$C_8$-alkoxy, aryloxy, ($C_1$–$C_8$-alkyl)mercapto, $NH_2$, ($C_1$–$C_8$-alkyl)amino, and di($C_1$–$C_8$-alkyl)amino; $C_3$–$C_5$-alkandiyl; phenyl; heteroaryl; aryl-substituted $C_1$–$C_4$-alkyl; heteroaryl-substitued $C_1$–$C_4$-alkyl; $CF_3$; $NO_2$; OH; phenoxy; benzyloxy; ($C_1$–$C_{10}$-alkyl)COO; $S(O)_m R^{20}$; SH; phenylamino; benzylamino; ($C_1$–$C_{10}$-alkyl)-CONH—; ($C_1$–$C_{10}$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_{10}$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; $COOR^{21}$; $CONR^{22}R^{23}$; $CNH(NH_2)$; $SO_2NR^{24}R^{25}$; $R^{26}SO_2NH$—; $R^{27}SO_2N(C_1$–$C_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said group Ar or said group Hetar; and wherein all aryl, heteroaryl, phenyl, aryl-containing, heteroaryl-containing and phenyl-containing groups, which are optionally present in said substituents of said group Ar or said group Hetar, can be substituted by one or more substituents chosen from halogens, pseudohalogens, $C_1$–$C_3$-alkyl, OH, $C_1$–$C_3$-alkoxy, and $CF_3$;

$R^6$ is chosen from:

H; $C_1$–$C_{10}$-alkyl, which can be substituted by one or more substituents chosen from F, $C_1$–$C_8$-alkoxy, and di($C_1$–$C_8$-alkyl)amino; aryl-($C_1$–$C_4$-alkyl) and heteroaryl-($C_1$–$C_4$-alkyl), which can be substituted by one or more substituents chosen from halogens, $C_1$–$C_4$-alkoxy, and di($C_1$–$C_6$-alkyl)amino;

$R^7$ is chosen from:

H; $C_1$–$C_{10}$-alkyl which can be substituted by one or more substituents chosen from F, $C_1$–$C_8$-alkoxy, di($C_1$–$C_8$-alkyl)amino and phenyl; phenyl; indanyl; and heteroaryl; and wherein each of the aforementioned aromatic groups can be unsubstituted or carry one or more substituents chosen from halogens, pseudohalogens, $C_1$–$C_3$-alkyl, $C_1$–$C_3$-alkoxy and $CF_3$;

$R^8$ is H or $C_1$–$C_{10}$-alkyl;

$R^9$ is chosen from: $C_1$–$C_{10}$-alkyl which can be unsubstituted or carry one or more substituents chosen from: F, ($C_1$–$C_4$)-alkoxy, di($C_1$–$C_3$-alkyl)amino; and unsubstituted and at least monosubstituted phenyl and heteroaryl, the substituents of which are chosen from $C_1$–$C_3$-alkyl, $C_1$–$C_3$-alkoxy, halogens, pseudohalogens, and $CF_3$;

$R^{10}$ independently has the same meaning as $R^7$;

$R^{11}$ independently has the same meaning as $R^8$;

$R^{12}$ independently has the same meaning as $R^6$;

$R^{13}$ is chosen from: H; $C_1$–$C_6$-alkyl; unsubstituted and substituted phenyl, benzyl, heteroaryl, ($C_1$–$C_6$-alkyl)-CO, phenyl-CO, and heteroaryl-CO, the substituents of which are chosen from halogens, pseudohalogens, $C_1$–$C_3$-alkyl, $C_1$–$C_3$-alkoxy, and $CF_3$, and wherein one or more of these substituents can be present;

$R^{14}$ independently has the same meaning as $R^{13}$;

$R^{15}$ is chosen from: H; $C_1$–$C_{10}$-alkyl; ($C_1$–$C_3$-alkoxy)-$C_1$–$C_3$-alkyl; and substituted and unsubstituted benzyl, phenyl and heteroaryl, the substituents of which are chosen from halogens, pseudohalogens, $C_1$–$C_3$-alkyl, $C_1$–$C_3$-alkoxy, and $CF_3$, and wherein one or more of these substituents can be present;

$R^{16}$ is chosen from: $C_1$–$C_{10}$-alkyl which can be substituted by one or more substituents chosen from F, OH, $C_1$–$C_8$-alkoxy, aryloxy, ($C_1$–$C_8$-alkyl)mercapto, ($C_1$–$C_8$-alkyl)amino and di($C_1$–$C_8$-alkyl)amino; $CF_3$; and substituted and unsubstituted phenyl and heteroaryl, the substituents of which are chosen from halogens, pseudohalogens, $C_1$–$C_3$-alkyl, $C_1$–$C_3$-alkoxy and $CF_3$, and wherein one or more of these substitutents can be present;

$R^{17}$ independently has the same meaning as $R^7$;

$R^{18}$ independently has the same meaning as $R^8$;

$R^{19}$ independently has the same meaning as $R^{16}$;

$R^{20}$ independently has the same meaning as $R^{16}$;

$R^{21}$ independently has the same meaning as $R^6$;

$R^{22}$ independently has the same meaning as $R^7$;

$R^{23}$ independently has the same meaning as $R^8$;

$R^{24}$ independently has the same meaning as $R^7$;

$R^{25}$ independently has the same meaning as $R^8$;

$R^{26}$ independently has the same meaning as $R^{16}$;

$R^{27}$ independently has the same meaning as $R^{16}$;

heteroaryl is a 5 to 10-membered, aromatic, mono- or bicyclic heterocycle containing one or more heteroatoms chosen from N, O, and S:

the group Hetar is a 5 to 10-membered, aromatic, mono- or bicyclic heterocycle containing one or more heteroatoms chosen from N, O, and S;

aryl is phenyl, naphth-1-yl or naphth-2-yl;

the group Ar is phenyl, naphth-1-yl or naphth-2-yl; and m is 0, 1 or 2;

wherein the physiologically active amount of the compound according to the general formula (I) in any of its stereoisomeric forms or a mixture thereof in any ratio or a pharmaceutically acceptable salt thereof stimulates the expression of endothelial NO-synthase in the mammal.

16. A method of treating a mammal suffering from diabetes complications wherein the diabetes complications are chosen from nephropathy and retinopathy, which method comprises administering to said mammal a physiologically active amount of a compound according to the general formula (I), in any of its stereoisomeric forms or a mixture thereof in any ratio or a pharmaceutically acceptable salt thereof

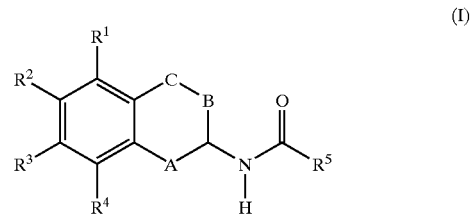

(I)

wherein, in the formula (I), $R^1$ and $R^4$ are independently from each other chosen from:

H; unsubstituted and at least monosubstituted $C_1$–$C_{10}$-alkyl, $C_2$–$C_{10}$-alkenyl and $C_2$–$C_{10}$-alkynyl, the substituents of which are chosen from F, OH, $C_1$–$C_8$-alkoxy, ($C_1$–$C_8$-alkyl)mercapto, CN, $COOR^6$, CONR$^7$R$^8$, and unsubstituted and at least monosubstituted phenyl and heteroaryl, the substituents of which are chosen from halogens, pseudohalogens, C$_1$–C$_3$-alkyl, C$_1$–C$_3$-alkoxy and CF$_3$; unsubstituted and at least monosubstituted phenyl and heteroaryl, the substituents of which are chosen from halogens, pseudohalogens, C$_1$–C$_3$-alkyl, C$_1$–C$_3$-alkoxy and CF$_3$; R$^9$CO; CONR$^{10}$R$^{11}$; COOR$^{12}$; CF$_3$; halogens; pseudohalogens; NR$^{13}$R$^{14}$; OR$^{15}$; S(O)$_m$R$_{16}$; SO$_2$NR$^{17}$R$^{18}$; and NO$_2$;

R$^2$ and R$^3$ are independently from each other chosen from:

H; halogens; pseudohalogens; unsubstituted and at least monosubstituted C$_1$–C$_{10}$-alkyl the substituents of which are chosen from OH, phenyl, and heteroaryl; OH; C$_1$–C$_{10}$-alkoxy; phenoxy; S(O)$_m$R$^{19}$; CF$_3$; CN; NO$_2$; (C$_1$–C$_{10}$-alkyl)amino; di(C$_1$–C$_{10}$-alkyl)amino; (C$_1$–C$_6$-alkyl)-CONH—; unsubstituted and at least monosubstituted phenyl-CONH— and phenyl-SO$_2$—O—, the substituents of which are chosen from halogens, pseudohalogens, CH$_3$ and methoxy; (C$_1$–C$_6$-alkyl)SO$_2$—O—; unsubstituted and at least monosubstituted (C$_1$–C$_6$-alkyl)CO, the substituents of which are chosen from F, di(C$_1$–C$_3$-alkyl)amino, pyrrolidinyl and piperidinyl; and phenyl-CO, the phenyl part of which can be substituted by one or more substituents chosen from C$_1$–C$_3$-alkyl, halogens and methoxy;

A is chosen from CH$_2$, CHOH and CH—(C$_1$–C$_3$-alkyl);

B is chosen from CH$_2$ and CH—(C$_1$–C$_3$-alkyl);

C independently has the same meaning as B;

R$^5$ is a group Ar or a group Hetar both of which can be unsubstituted or carry one or more substituents chosen from: halogens; pseudohalogens; NH$_2$; unsubstituted and at least monosubstituted C$_1$–C$_{10}$-alkyl, C$_2$–C$_{10}$-alkenyl, C$_2$–C$_{10}$-alkynyl, C$_1$–C$_{10}$-alkoxy, (C$_1$–C$_{10}$-alkyl)amino, and di(C$_1$–C$_{10}$-alkyl)amino, the substituents of which are chosen from F, OH, C$_1$–C$_8$-alkoxy, aryloxy, (C$_1$–C$_8$-alkyl)mercapto, NH$_2$, (C$_1$–C$_8$-alkyl)amino, and di(C$_1$–C$_8$-alkyl)amino; C$_3$–C$_5$-alkandiyl; phenyl; heteroaryl; aryl-substituted C$_1$–C$_4$-alkyl; heteroaryl-substituted C$_1$–C$_2$-alkyl; CF$_3$; NO$_2$; OH; phenoxy; benzyloxy; (C$_1$–C$_{10}$-alkyl)COO; S(O)$_m$R$^{20}$; SH; phenylamino; benzylamino; (C$_1$–C$_{10}$-alkyl)-CONH—; (C$_1$–C$_{10}$-alkyl)-CON(C$_1$–C$_4$-alkyl)-; phenyl-CONH—; phenyl-CON(C$_1$–C$_4$-alkyl)-; heteroaryl-CONH—; heteroaryl-CON(C$_1$–C$_4$-alkyl)-; (C$_1$–C$_{10}$-alkyl)-CO; phenyl-CO; heteroaryl-CO; CF$_3$—CO; —OCH$_2$O—; —OCF$_2$O—; —OCH$_2$CH$_2$O—; —CH$_2$CH$_2$O—; COOR$^{21}$; CONR$^{22}$R$^{23}$; CNH(NH$_2$); SO$_2$NR$^{24}$R$^{25}$; R$^{26}$SO$_2$NH—; R$^{27}$SO$_2$N(C$_1$–C$_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, C$_1$–C$_3$-alkyl, C$_1$–C$_3$-alkoxy, OH, oxo and CF$_3$, and wherein said heterocycles can optionally be condensed to said group Ar or said group Hetar; and wherein all aryl, heteroaryl, phenyl, aryl-containing, heteroaryl-containing and phenyl-containing groups, which are optionally present in said substituents of said group Ar or said group Hetar, can be substituted by one or more substituents chosen from halogens, pseudohalogens, C$_1$–C$_3$-alkyl, OH, C$_1$–C$_3$-alkoxy, and CF$_3$;

R$^6$ is chosen from:

H; C$_1$–C$_{10}$-alkyl, which can be substituted by one or more substituents chosen from F, C$_1$–C$_8$-alkoxy, and di(C$_1$–C$_8$-alkyl)amino; aryl-(C$_1$–C$_4$-alkyl) and heteroaryl-(C$_1$–C$_4$-alkyl), which can be substituted by one or more substituents chosen from halogens, C$_1$–C$_4$-alkoxy, and di(C$_1$–C$_6$-alkyl)amino;

R$^7$ is chosen from:

H; C$_1$–C$_{10}$-alkyl which can be substituted by one or more substituents chosen from F, C$_1$–C$_8$-alkoxy, di(C$_1$–C$_8$-alkyl)amino and phenyl; phenyl; indanyl; and heteroaryl; and wherein each of the aforementioned aromatic groups can be unsubstituted or carry one or more substituents chosen from halogens, pseudohalogens, C$_1$–C$_3$-alkyl, C$_1$–C$_3$-alkoxy and CF$_3$;

R$^8$ is H or C$_1$–C$_{10}$-alkyl;

R$^9$ is chosen from: C$_1$–C$_{10}$-alkyl which can be unsubstituted or carry one or more substituents chosen from: F, (C$_1$–C$_4$)-alkoxy, di(C$_1$–C$_3$-alkyl)amino; and unsubstituted and at least monosubstituted phenyl and heteroaryl, the substituents of which are chosen from C$_1$–C$_3$-alkyl, C$_1$–C$_3$-alkoxy, halogens, pseudohalogens, and CF$_3$;

R$^{10}$ independently has the same meaning as R$^7$;

R$^{11}$ independently has the same meaning as R$^8$;

R$^{12}$ independently has the same meaning as R$^6$;

R$^{13}$ is chosen from: H; C$_1$–C$_6$-alkyl; unsubstituted and substituted phenyl, benzyl, heteroaryl, (C$_1$–C$_6$-alkyl)-CO, phenyl-CO, and heteroaryl-CO, the substituents of which are chosen from halogens, pseudohalogens, C$_1$–C$_3$-alkyl, C$_1$–C$_3$-alkoxy, and CF$_3$, and wherein one or more of these substituents can be present;

R$^{14}$ independently has the same meaning as R$^{13}$;

R$^{15}$ is chosen from: H; C$_1$–C$_{10}$-alkyl; (C$_1$–C$_3$-alkoxy)-C$_1$–C$_3$-alkyl; and substituted and unsubstituted benzyl, phenyl and heteroaryl, the substituents of which are chosen from halogens, pseudohalogens, C$_1$–C$_3$-alkyl, C$_1$–C$_3$-alkoxy, and CF$_3$, and wherein one or more of these substituents can be present;

R$^{16}$ is chosen from: C$_1$–C$_{10}$-alkyl which can be substituted by one or more substituents chosen from F, OH, C$_1$–C$_8$-alkoxy, aryloxy, (C$_1$–C$_8$-alkyl)mercapto, (C$_1$–C$_8$-alkyl)amino and di(C$_1$–C$_8$-alkyl)amino; CF$_3$; and substituted and unsubstituted phenyl and heteroaryl, the substituents of which are chosen from halogens, pseudohalogens, C$_1$–C$_3$-alkyl, C$_1$–C$_3$-alkoxy and CF$_3$, and wherein one or more of these substitutents can be present;

R$^{17}$ independently has the same meaning as R$^7$;

R$^{18}$ independently has the same meaning as R$^8$;

R$^{19}$ independently has the same meaning as R$^{16}$;

R$^{20}$ independently has the same meaning as R$^{16}$;

R$^{21}$ independently has the same meaning as R$^6$;

R$^{22}$ independently has the same meaning as R$^7$;

R$^{23}$ independently has the same meaning as R$^8$;

R$^{24}$ independently has the same meaning as R$^7$;

R$^{25}$ independently has the same meaning as R$^8$;

R$^{26}$ independently has the same meaning as R$^{16}$;

R$^{27}$ independently has the same meaning as R$^{16}$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O, and S;

aryl is phenyl, naphth-1-yl or naphth-2-yl;

the group Ar is phenyl, naphth-1-yl or naphth-2-yl; and
m is 0, 1 or 2;

wherein the physiologically active amount of the compound according to the general formula (I) in any of its stereoisomeric forms or a mixture thereof in any ratio or a pharmaceutically acceptable salt thereof stimulates the expression of endothelial NO-synthase in the mammal.

17. A method of lowering cardiovascular risk of post-menopausal women and mammals contraceptives, which method comprises administering to said mammal a physiologically active amount of a compound according to the general formula (I), in any of its stereoisomeric forms or a mixture thereof in any ratio or a pharmaceutically acceptable salt thereof

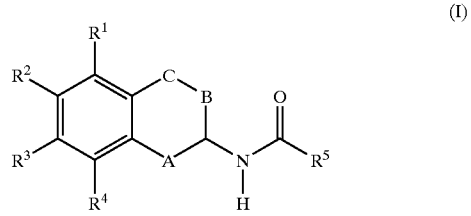

(I)

wherein, in the formula (I), $R^1$ and $R^4$ are independently from each other chosen from:

H; unsubstituted and at least monosubstituted $C_1$–$C_{10}$-alkyl, $C_2$–$C_{10}$-alkenyl and $C_2$–$C_{10}$-alkynyl, the substituents of which are chosen from F, OH, $C_1$–$C_8$-alkoxy, ($C_1$–$C_8$-alkyl)mercapto, CN, COOR$^6$, CONR$^7$R$^8$, and unsubstituted and at least monosubstituted phenyl and heteroaryl, the substituents of which are chosen from halogens, pseudohalogens, $C_1$–$C_3$-alkyl, $C_1$–$C_3$-alkoxy and CF$_3$; unsubstituted and at least monosubstituted phenyl and heteroaryl, the substituents of which are chosen from halogens, pseudohalogens, $C_1$–$C_3$-alkyl, $C_1$–$C_3$-alkoxy and CF$_3$; $R^9$CO; CONR$^{10}$R$^{11}$; COOR$^{12}$; CF$_3$; halogens; pseudohalogens; NR$^{13}$R$^{14}$; OR$^{15}$; S(O)$_m$R$^{16}$; SO$_2$NR$^{17}$R$^{18}$; and NO$_2$;

$R^2$ and $R^3$ are independently from each other chosen from:

H; halogens; pseudohalogens; unsubstituted and at least monosubstituted $C_1$–$C_{10}$-alkyl the substituents of which are chosen from OH, phenyl, and heteroaryl; OH; $C_1$–$C_{10}$-alkoxy; phenoxy; S(O)$_m$R$^{19}$; CF$_3$; CN; NO$_2$; ($C_1$–$C_{10}$-alkyl)amino; di($C_1$–$C_{10}$-alkyl)amino; ($C_1$–$C_6$-alkyl)-CONH—; unsubstituted and at least monosubstituted phenyl-CONH— and phenyl-SO$_2$—O—, the substituents of which are chosen from halogens, pseudohalogens, CH$_3$ and methoxy; ($C_1$–$C_6$-alkyl)SO$_2$—O—; unsubstituted and at least monosubstituted ($C_1$–$C_6$-alkyl)CO, the substituents of which are chosen from F, di($C_1$–$C_3$-alkyl)amino, pyrrolidinyl and piperidinyl; and phenyl-CO, the phenyl part of which can be substituted by one or more substituents chosen from $C_1$–$C_3$-alkyl, halogens and methoxy;

A is chosen from CH$_2$, CHOH and CH—($C_1$–$C_3$-alkyl);
B is chosen from CH$_2$ and CH—($C_1$–$C_3$-alkyl);
C independently has the same meaning as B;
$R^5$ is a group Ar or a group Hetar both of which can be unsubstituted or carry one or more substituents chosen from: halogens; pseudohalogens; NH$_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, ($C_1$–$C_{10}$-alkyl)amino, and di($C_1$–$C_{10}$-alkyl)amino, the substituents of which are chosen from F, OH, $C_1$–$C_8$-alkoxy, aryloxy, ($C_1$–$C_8$-alkyl)mercapto, NH$_2$, ($C_1$–$C_8$-alkyl)amino, and di($C_1$–$C_8$-alkyl)amino; $C_3$–$C_5$-alkandiyl; phenyl; heteroaryl; aryl-substituted $C_1$–$C_4$-alkyl; heteroaryl-substituted $C_1$–$C_2$-alkyl; CF$_3$; NO$_2$; OH; phenoxy; benzyloxy; ($C_1$–$C_{10}$-alkyl)COO; S(O)$_m$R$^{20}$; SH; phenylamino; benzylamino; ($C_1$–$C_{10}$-alkyl)-CONH—; ($C_1$–$C_{10}$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_{10}$-alkyl)-CO; phenyl-CO; heteroaryl-CO; CF$_3$—CO; —OCH$_2$O—; —OCF$_2$O—; —OCH$_2$CH$_2$O—; —CH$_2$CH$_2$O—; COOR$^{21}$; CONR$^{22}$R$^{23}$; CNH(NH$_2$); SO$_2$NR$^{24}$R$^{25}$; R$^{26}$SO$_2$NH—; R$^{27}$SO$_2$N($C_1$–$C_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and CF$_3$, and wherein said heterocycles can optionally be condensed to said group Ar or said group Hetar; and wherein all aryl, heteroaryl, phenyl, aryl-containing, heteroaryl-containing and phenyl-containing groups, which are optionally present in said substituents of said group Ar or said group Hetar, can be substituted by one or more substituents chosen from halogens, pseudohalogens, $C_1$–$C_3$-alkyl, OH, $C_1$–$C_3$-alkoxy, and CF$_3$;

$R^6$ is chosen from:

H; $C_1$–$C_{10}$-alkyl, which can be substituted by one or more substituents chosen from F, $C_1$–$C_8$-alkoxy, and di($C_1$–$C_8$-alkyl)amino; aryl-($C_1$–$C_4$-alkyl) and heteroaryl-($C_1$–$C_4$-alkyl), which can be substituted by one or more substituents chosen from halogens, $C_1$–$C_4$-alkoxy, and di($C_1$–$C_6$-alkyl)amino;

$R^7$ is chosen from:

H; $C_1$–$C_{10}$-alkyl which can be substituted by one or more substituents chosen from F, $C_1$–$C_8$-alkoxy, di($C_1$–$C_8$-alkyl)amino and phenyl; phenyl; indanyl; and heteroaryl; and wherein each of the aforementioned aromatic groups can be unsubstituted or carry one or more substituents chosen from halogens, pseudohalogens, $C_1$–$C_3$-alkyl, $C_1$–$C_3$-alkoxy and CF$_3$;

$R^8$ is H or $C_1$–$C_{10}$-alkyl;

$R^9$ is chosen from: $C_1$–$C_{10}$-alkyl which can be unsubstituted or carry one or more substituents chosen from: F, ($C_1$–$C_4$)-alkoxy, di($C_1$–$C_3$-alkyl)amino; and unsubstituted and at least monosubstituted phenyl and heteroaryl, the substituents of which are chosen from $C_1$–$C_3$-alkyl, $C_1$–$C_3$-alkoxy, halogens, pseudohalogens, and CF$_3$;

$R^{10}$ independently has the same meaning as $R^7$;
$R^{11}$ independently has the same meaning as $R^8$;
$R^{12}$ independently has the same meaning as $R^6$;
$R^{13}$ is chosen from: H; $C_1$–$C_6$-alkyl; unsubstituted and substituted phenyl, benzyl, heteroaryl, ($C_1$–$C_6$-alkyl)-CO, phenyl-CO, and heteroaryl-CO, the substituents of which are chosen from halogens, pseudohalogens, $C_1$–$C_3$-alkyl, $C_1$–$C_3$-alkoxy, and CF$_3$, and wherein one or more of these substituents can be present;

$R^{14}$ independently has the same meaning as $R^{13}$;
$R^{15}$ is chosen from: H; $C_1$–$C_{10}$-alkyl; ($C_1$–$C_3$-alkoxy)-$C_1$–$C_3$-alkyl; and substituted and unsubstituted benzyl, phenyl and heteroaryl, the substituents of which are chosen from halogens, pseudohalogens, $C_1$–$C_3$-alkyl, $C_1$–$C_3$-alkoxy, and $CF_3$, and wherein one or more of these substituents can be present;

$R^{16}$ is chosen from: $C_1$–$C_{10}$-alkyl which can be substituted by one or more substituents chosen from F, OH, $C_1$–$C_8$-alkoxy, aryloxy, ($C_1$–$C_8$-alkyl)mercapto, ($C_1$–$C_8$-alkyl)amino and di($C_1$–$C_8$-alkyl)amino; $CF_3$; and substituted and unsubstituted phenyl and heteroaryl, the substituents of which are chosen from halogens, pseudohalogens, $C_1$–$C_3$-alkyl, $C_1$–$C_3$-alkoxy and $CF_3$, and wherein one or more of these substitutents can be present;

$R^{17}$ independently has the same meaning as $R^7$;
$R^{18}$ independently has the same meaning as $R^8$;
$R^{19}$ independently has the same meaning as $R^{16}$;
$R^{20}$ independently has the same meaning as $R^{16}$;
$R^{21}$ independently has the same meaning as $R^6$;
$R^{22}$ independently has the same meaning as $R^7$;
$R^{23}$ independently has the same meaning as $R^8$;
$R^{24}$ independently has the same meaning as $R^7$;
$R^{25}$ independently has the same meaning as $R^8$;
$R^{26}$ independently has the same meaning as $R^{16}$;
$R^{27}$ independently has the same meaning as $R^{16}$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O, and S;

aryl is phenyl, naphth-1-yl or naphth-2-yl;

the group Ar is phenyl, naphth-1-yl or naphth-2-yl; and m is 0, 1 or 2;

wherein the physiologically active amount of the compound according to the general formula (I) in any of its stereoisomeric forms or a mixture thereof in any ratio or a pharmaceutically acceptable salt thereof stimulates the expression of endothelial NO-synthase in the mammal.

18. A method of treating a mammal suffering from a cardiovascular disease, which method comprises administering to said mammal a physiologically active amount of a compound according to the general formula (I), in any of its stereoisomeric forms or a mixture thereof in any ratio or a pharmaceutically acceptable salt thereof

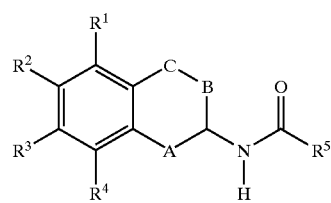

(I)

wherein, in the formula (I), $R^1$ and $R^4$ are independently from each other chosen from:

H; unsubstituted and at least monosubstituted $C_1$–$C_{10}$-alkyl, $C_2$–$C_{10}$-alkenyl and $C_2$–$C_{10}$-alkynyl, the substituents of which are chosen from F, OH, $C_1$–$C_8$-alkoxy, ($C_1$–$C_8$-alkyl)mercapto, CN, $COOR^6$, $CONR^7R^8$, and unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; $R^9CO$; $CONR^{10}R^{11}$; $COOR^{12}$; $CF_3$; halogens; pseudohalogens; $NR^{13}R^{14}$; $OR^{15}$; $S(O)_mR_{16}$; $SO_2NR^{17}R^{18}$; and $NO_2$;

$R^2$ and $R^3$ are independently from each other chosen from:

H; halogens; pseudohalogens; unsubstituted and at least monosubstituted $C_1$–$C_{10}$-alkyl the substituents of which are chosen from OH, phenyl, and heteroaryl; OH; $C_1$–$C_{10}$-alkoxy; phenoxy; $S(O)_mR^{19}$; $CF_3$; CN; $NO_2$; ($C_1$–$C_{10}$-alkyl)amino; di($C_1$–$C_{10}$-alkyl)amino; ($C_1$–$C_6$-alkyl)-CONH—; unsubstituted and at least monosubstituted phenyl-CONH— and phenyl-$SO_2$—O—, the substituents of which are chosen from halogens, pseudohalogens, $CH_3$ and methoxy; ($C_1$–$C_6$-alkyl)$SO_2$—O—; unsubstituted and at least monosubstituted ($C_1$–$C_6$-alkyl)CO, the substituents of which are chosen from F, di($C_1$–$C_3$-alkyl)amino, pyrrolidinyl and piperidinyl; and phenyl-CO, the phenyl part of which can be substituted by one or more substituents chosen from $C_1$–$C_3$-alkyl, halogens and methoxy;

A is chosen from $CH_2$, CHOH and CH—($C_1$–$C_3$-alkyl);

B is chosen from $CH_2$ and CH—($C_1$–$C_3$-alkyl);

C independently has the same meaning as B;

$R^5$ is a group Ar or a group Hetar both of which can be unsubstituted or carry one or more substituents chosen from: halogens; pseudohalogens; $NH_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, ($C_1$–$C_{10}$-alkyl)amino, and di($C_1$–$C_{10}$-alkyl)amino, the substituents of which are chosen from F, OH, $C_1$–$C_8$-alkoxy, aryloxy, ($C_1$–$C_8$-alkyl)mercapto, $NH_2$, ($C_1$–$C_8$-alkyl)amino, and di($C_1$–$C_8$-alkyl)amino; $C_3$–$C_5$-alkandiyl; phenyl; heteroaryl; aryl-substituted $C_1$–$C_4$-alkyl; heteroaryl-substituted $C_1$–$C_2$-alkyl; $CF_3$; $NO_2$; OH; phenoxy; benzyloxy; ($C_1$–$C_{10}$-alkyl)COO; $S(O)_mR^{20}$; SH; phenylamino; benzylamino; ($C_1$–$C_{10}$-alkyl)-CONH—; ($C_1$–$C_{10}$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_{10}$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; $COOR^{21}$; $CONR^{22}R^{23}$; CNH($NH_2$); $SO_2NR^{24}R^{25}$; $R^{26}SO_2NH$—; $R^{27}SO_2N(C_1$–$C_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said group Ar or said group Hetar; and wherein all aryl, heteroaryl, phenyl, aryl-containing, heteroaryl-containing and phenyl-containing groups, which are optionally present in said substituents of said group Ar or said group Hetar, can be substituted by one or more substituents chosen from halogens, pseudohalogens, $C_1$–$C_3$-alkyl, OH, $C_1$–$C_3$-alkoxy, and $CF_3$;

$R^6$ is chosen from:

H; $C_1$–$C_{10}$-alkyl, which can be substituted by one or more substituents chosen from F, $C_1$–$C_8$-alkoxy, and di($C_1$–$C_8$-alkyl)amino; aryl-($C_1$–$C_4$-alkyl) and heteroaryl-($C_1$–$C_4$-alkyl), which can be substituted by one or more substituents chosen from halogens, $C_1$–$C_4$-alkoxy, and di($C_1$–$C_6$-alkyl)amino;

$R^7$ is chosen from:

H; $C_1$–$C_{10}$-alkyl which can be substituted by one or more substituents chosen from F, $C_1$–$C_8$-alkoxy, di($C_1$–$C_8$-alkyl)amino and phenyl; phenyl; indanyl; and heteroaryl; and wherein each of the aforementioned aromatic groups can be unsubstituted or carry one or more substituents chosen from halogens, pseudohalogens, $C_1$–$C_3$-alkyl, $C_1$–$C_3$-alkoxy and $CF_3$;

$R^8$ is H or $C_1$–$C_{10}$-alkyl;

$R^9$ is chosen from: $C_1$–$C_{10}$-alkyl which can be unsubstituted or carry one or more substituents chosen from: F, ($C_1$–$C_4$)-alkoxy, di($C_1$–$C_3$-alkyl)amino; and unsubstituted and at least monosubstituted phenyl and heteroaryl, the substituents of which are chosen from $C_1$–$C_3$-alkyl, $C_1$–$C_3$-alkoxy, halogens, pseudohalogens, and $CF_3$;

$R^{10}$ independently has the same meaning as $R^7$;

$R^{11}$ independently has the same meaning as $R^8$;

$R^{12}$ independently has the same meaning as $R^6$;

$R^{13}$ is chosen from: H; $C_1$–$C_6$-alkyl; unsubstituted and substituted phenyl, benzyl, heteroaryl, ($C_1$–$C_6$-alkyl)-CO, phenyl-CO, and heteroaryl-CO, the substituents of which are chosen from halogens, pseudohalogens, $C_1$–$C_3$-alkyl, $C_1$–$C_3$-alkoxy, and $CF_3$, and wherein one or more of these substituents can be present;

$R^{14}$ independently has the same meaning as $R^{13}$;

$R^{15}$ is chosen from: H; $C_1$–$C_{10}$-alkyl; ($C_1$–$C_3$-alkoxy)-$C_1$–$C_3$-alkyl; and substituted and unsubstituted benzyl, phenyl and heteroaryl, the substituents of which are chosen from halogens, pseudohalogens, $C_1$–$C_3$-alkyl, $C_1$–$C_3$-alkoxy, and $CF_3$, and wherein one or more of these substituents can be present;

$R^{16}$ is chosen from: $C_1$–$C_{10}$-alkyl which can be substituted by one or more substituents chosen from F, OH, $C_1$–$C_8$-alkoxy, aryloxy, ($C_1$–$C_8$-alkyl)mercapto, ($C_1$–$C_8$-alkyl)amino and di($C_1$–$C_8$-alkyl)amino; $CF_3$; and substituted and unsubstituted phenyl and heteroaryl, the substituents of which are chosen from halogens, pseudohalogens, $C_1$–$C_3$-alkyl, $C_1$–$C_3$-alkoxy and $CF_3$, and wherein one or more of these substituents can be present;

$R^{17}$ independently has the same meaning as $R^7$;

$R^{18}$ independently has the same meaning as $R^8$;

$R^{19}$ independently has the same meaning as $R^{16}$;

$R^{20}$ independently has the same meaning as $R^{16}$;

$R^{21}$ independently has the same meaning as $R^6$;

$R^{22}$ independently has the same meaning as $R^7$;

$R^{23}$ independently has the same meaning as $R^8$;

$R^{24}$ independently has the same meaning as $R^7$;

$R^{25}$ independently has the same meaning as $R^8$;

$R^{26}$ independently has the same meaning as $R^{16}$;

$R^{27}$ independently has the same meaning as $R^{16}$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O, and S;

aryl is phenyl, naphth-1-yl or naphth-2-yl;

the group Ar is phenyl, naphth-1-yl or naphth-2-yl; and m is 0, 1 or 2;

wherein the physiologically active amount of the compound according to the general formula (I) in any of its stereoisomeric forms or a mixture thereof in any ratio or a pharmaceutically acceptable salt thereof stimulates the expression of endothelial NO-synthase in the mammal.

19. The method according to claim 18, wherein the compound of the general formula (I) is chosen from compounds of the general formula (I), wherein $R^1$ is chosen from: H; $C_1$–$C_4$-alkyl; $C_1$–$C_4$-alkoxy; $CF_3$; halogens; pseudohalogens; ($C_1$–$C_4$-alkyl)-S(O)$_m$—; and unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$, and wherein heteroaryl is chosen from 5- and 6-membered heterocycles containing one or more heteroatoms chosen from N, O, and S;

$R^2$ and $R^3$ are independently from each other chosen from: H; halogens; pseudohalogens; and $C_1$–$C_3$-alkyl;

$R^4$ independently has the same meaning as $R^1$;

A is chosen from $CH_2$ and CHOH;

B and C are independently from each other chosen from $CH_2$ and CH—$CH_3$;

$R^5$ is a group Ar or a group Hetar both of which can be unsubstituted or carry one or more substituents chosen from: halogens; CN; $NH_2$; unsubstituted and at least monosubstituted $C_1$–$C_8$-alkyl, $C_2$–$C_8$-alkenyl, $C_2$–$C_8$-alkynyl, $C_1$–$C_8$-alkoxy, ($C_1$–$C_8$-alkyl)amino, and di($C_1$–$C_8$-alkyl)amino, the substituents of which are chosen from F, $C_1$–$C_6$-alkoxy, phenoxy, ($C_1$–$C_6$-alkyl)mercapto, $NH_2$, ($C_1$–$C_6$-alkyl)amino, and di($C_1$–$C_6$-alkyl)amino; $C_3$–$C_5$-alkandiyl; phenyl; heteroaryl; phenyl-substituted $C_1$–$C_2$-alkyl; heteroaryl-substituted $C_1$–$C_2$-alkyl; $CF_3$; OH; phenoxy; benzyloxy; ($C_1$–$C_6$-alkyl)COO; S(O)$_m$($C_1$–$C_6$)-alkyl; S(O)$_m$-phenyl; S(O)$_m$-heteroaryl; SH; phenylamino; benzylamino; ($C_1$–$C_6$-alkyl)-CONH—; ($C_1$–$C_6$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_6$-alkyl)-CO; phenyl-CO; heteroaryl-CO; $CF_3$—CO; —OCH$_2$O—; —OCF$_2$O—; —OCH$_2$CH$_2$O—; —CH$_2$CH$_2$O—; COO($C_1$–$C_6$-alkyl); —CONH$_2$; —CONH($C_1$–$C_6$-alkyl); —CON(di($C_1$–$C_6$-alkyl)); CNH($NH_2$); —SO$_2$NH$_2$; —SO$_2$NH($C_1$–$C_6$-alkyl); —SO$_2$NH(phenyl); —SO$_2$N(di($C_1$–$C_6$-alkyl)); ($C_1$–$C_6$-alkyl)SO$_2$NH—; ($C_1$–$C_6$-alkyl)SO$_2$N($C_1$–$C_6$-alkyl)-; phenyl-SO$_2$NH—; phenyl-SO$_2$N($C_1$–$C_6$-alkyl)-; heteroaryl-SO$_2$NH—; heteroaryl-SO$_2$N($C_1$–$C_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said group Ar or said group Hetar; and wherein all heteroaryl, phenyl, heteroaryl-containing and phenyl-containing groups, which are optionally present in said substituents of said group Ar or said group Hetar, can be substituted by one or more substituents chosen from halogens, pseudohalogens, $C_1$–$C_3$-alkyl, OH, $C_1$–$C_3$-alkoxy, and $CF_3$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O, and S;

the group Ar is phenyl, naphth-1-yl or naphth-2-yl; and m is 0 or 2.

20. The method according to claim 18, wherein the compound according to of the general formula (I) is chosen from compounds of the general formula (I), wherein $R^1$ is H, halogen, or $C_1$–$C_4$-alkyl;

$R^2$ and $R^3$ are each H;

$R^4$ independently has the same meaning as $R^1$;

A is $CH_2$;

$R^5$ is phenyl or a group Hetar both of which can be unsubstituted or carry one or more substituents chosen from: halogens; CN; $NH_2$; unsubstituted and at least monosubstituted $C_1$–$C_6$-alkyl, $C_2$–$C_6$-alkenyl, $C_2$–$C_6$-alkynyl, $C_1$–$C_3$-alkoxy, ($C_1$–$C_4$-alkyl)amino, and di($C_1$–$C_4$-alkyl)amino, the substituents of which are chosen from F, $C_1$–$C_3$-alkoxy, ($C_1$–$C_3$-alkyl)mercapto, and $NH_2$; $C_3$–$C_5$-alkandryl; phenyl; heteroaryl; phenyl-substituted $C_1$–$C_2$-alkyl; heteroaryl-substituted $C_1$–$C_2$-alkyl; $CF_3$; OH; ($C_1$–$C_4$-alkyl)COO; $S(O)_m(C_1$–$C_4)$-alkyl; ($C_1$–$C_4$-alkyl)-CONH—; ($C_1$–$C_4$-alkyl)-CON($C_1$–$C_4$-alkyl)-; ($C_1$–$C_4$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; COO($C_1$–$C_6$-alkyl); —$CONH_2$; —CONH($C_1$–$C_4$-alkyl); —CON(di($C_1$–$C_4$-alkyl)); CNH($NH_2$); —$SO_2NH_2$; —$SO_2NH$($C_1$–$C_4$-alkyl); —$SO_2NH$(phenyl); —$SO_2N$(di($C_1$–$C_4$-alkyl)); ($C_1$–$C_4$-alkyl)$SO_2NH$—; ($C_1$–$C_4$-alkyl)$SO_2N$($C_1$–$C_4$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said phenyl or said group Hetar; and wherein all heteroaryl, phenyl, heteroaryl-containing and phenyl-containing groups, which are optionally present in said substituents of said phenyl or said group Hetar, can be substituted by one or more substituents; chosen from halogens, pseudohalogens, $C_1$–$C_3$-alkyl, OH, $C_1$–$C_3$-alkoxy, and $CF_3$;

heteroaryl is a 5 to 10-membered, aromatic, mono- or bicyclic heterocycle containing one, two or three heteroatoms chosen from N, O, and S;

the group Hetar is a 5 to 10-membered, aromatic, mono- or bicyclic heterocycle containing one, two or three heteroatoms chosen from N, O, and S; and m is 0 or 2.

21. The method according to claim 18, wherein the compound according to the general formula (I) is chosen from the compounds of the general formula (I) wherein $R^1$ is H, halogen, or $C_1$–$C_4$-alkyl;

$R^2$ and $R^3$ are each H;

$R^4$ independently has the same meaning as $R^1$;

A and B are each $CH_2$;

C is $CH_2$ or CH—$CH_3$;

$R^5$ is phenyl or a group Hetar both of which can be unsubstituted or carry one or more substituents chosen from: F; Cl; Br; $C_1$–$C_3$-alkyl; $C_1$–$C_3$-alkoxymethyl; 2-amino-3,3,3-trifluoro-propyl-; $CF_3$; $C_3$–$C_5$-alkandiyl; phenyl; heteroaryl; benzyl; heteroaryl-methyl; OH; $C_1$–$C_3$-alkoxy; phenoxy; trifluoromethoxy; 2,2,2-trifluoroethoxy; ($C_1$–$C_4$-alkyl)COO; ($C_1$–$C_3$-alkyl)mercapto; phenylmercapto; ($C_1$–$C_3$-alkyl)sulfonyl; phenylsulfonyl; $NH_2$; ($C_1$–$C_4$-alkyl)amino; di($C_1$–$C_4$-alkyl)amino; ($C_1$–$C_3$-alkyl)-CONH—; ($C_1$–$C_3$-alkyl)-$SO_2NH$—; ($C_1$–$C_3$-alkyl)-CO; phenyl-CO; —$OCH_2O$—; —$OCF_2O$—; —$CH_2CH_2O$—; COO($C_1$–$C_4$-alkyl); —$CONH_2$; —CONH($C_1$–$C_4$-alkyl); —CON(di($C_1$–$C_4$-alkyl)); CN; —$SO_2NH_2$; —$SO_2NH$($C_1$–$C_4$-alkyl); —$SO_2N$(di($C_1$–$C_4$-alkyl)); pyrrolidinyl; piperidinyl; morpholinyl; and thiomorpholinyl; and wherein all heteroaryl, phenyl, heteroaryl-containing and phenyl-containing groups, which are optionally present in said substituents of said phenyl or said group Hetar, can be substituted by one or more substituents chosen from halogens, pseudohalogens, $C_1$–$C_3$-alkyl, OH, $C_1$–$C_3$-alkoxy, and $CF_3$;

heteroaryl is chosen from: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl;

the group Hetar is chosen from: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl.

22. The method according to claim 18, wherein the compound according to the general formula (I) is chosen from the compounds of the general formula (I) wherein $R^1$ is H, halogen or $C_1$–$C_4$-alkyl;

$R^2$ and $R^3$ are each H;

$R^4$ independently has the same meaning as $R^1$;

A and B are each $CH_2$;

C is $CH_2$ or CH—$CH_3$;

$R^5$ is chosen from: 4-fluorophenyl, 4-chlorophenyl, 4-bromophenyl, 4-($C_1$–$C_3$-alkoxy)-phenyl, 4-trifluoromethoxyphenyl, 2-bromo-4-fluorophenyl, 2-chloro-4-fluorophenyl, 3,4-dimethylphenyl, 2,4-dimethylphenyl, 4-chloro-2-methylphenyl, 2-hydroxy-4-methylphenyl, 2-hydroxy-4-ethoxyphenyl, 2-methoxy-4-methylphenyl, 4-phenoxyphenyl, 3-fluoro-4-methylphenyl, benzo[1,3]dioxol-5-yl, 2,2-difluoro-benzo[1,3]dioxol-5-yl, 2,3-dihydrobenzofuran-5-yl, 1-(4-chloro-phenyl)-5-trifluoromethyl-1H-pyrazole-4-yl, 1-(4-fluoro-phenyl)-3,5-dimethyl-1H-pyrazole-4-yl, 1H-benzotriazole-5-yl, 1H-indole-4-yl, 1H-indole-6-yl, 1-isopropyl-2-trifluoromethyl-1H-benzoimidazole-5-yl, 1-methyl-3-oxo-1,2,3,4-tetrahydro-quinoxaline-6-yl, 1-phenyl-5-trifluoromethyl-1H-pyrazole-4-yl, 2-(2-hydroxy-pyridin-4-yl)-1H-benzoimidazole-5-yl, 2-(4-cyano-phenyl)-1H-benzoimidazole-5-yl, 2,4-dimethyl-oxazole-5-yl, 2,4-dimethyl-pyrimidine-5-yl, 2,4-dimethyl-thiazole-5-yl, 2,5-dimethyl-1H-pyrrole-3-yl, 2,5-dimethyl-1-phenyl-1H-pyrrole-3-yl, 2,5-dimethyl-1-pyridin-4-ylmethyl-1H-pyrrolyl, 2,5-dimethyl-2H-pyrazole-3-yl, 2,6-dichloro-pyrid-3-yl, 2,6-dimethoxy-pyrid-3-yl, 2,6-dimethyl-pyrid-3-yl, 2-amino-4,6-dimethyl-pyrid-3-yl, 2-amino-6-chloro-pyrid-3-yl, 2-amino-pyrid-3-yl, 2-chloro-6-methyl-pyrid-3-yl, 2-chloro-pyrid-4-yl, 2-cyclopropyl-4-methyl-thiazole-5-yl, 2-dimethylamino-4-methyl-thiazole-5-yl, 2-dimethylamino-pyrid-4-yl, 2-ethyl-5-methyl-2H-pyrazole-3-yl, 2-hydroxy-6-methyl-pyrid-3-yl, 2-methyl-1H-benzoimidazole-5-yl, 2-methyl-3H-benzoimidazole-5-yl, 2-methyl-pyrid-3-yl, 2-methyl-6-trifluoromethyl-pyrid-3-yl, 2-methyl-thiazole-5-yl, 2-morpholin-4-yl-pyridin-4-yl, 2-morpholin-4-yl-pyrimidine-5-yl, 2-pyrrolidin-1-yl-pyridin-4-yl, 3,5-dimethyl-1H-pyrazole-4-yl, 3-amino-5,6-dimethyl-pyrazine-2-yl, 3-amino-5-methyl-pyrazine-2-yl, 3-amino-pyrazine-2-yl, 3-dimethylamino-4-methyl-phenyl, 3-dimethylamino-phenyl, 3H-benzoimidazole-5-yl, 1H-benzoimidazole-5-yl, 3-methanesulfonylamino-2-methyl-phenyl, 3-methanesulfonylamino-phenyl, 3-methyl-isoxazole-4-yl, 3-morpholin-4-yl-phenyl, 3-piperidin-1-yl-phenyl, 3-pyrrolidin-1-yl-phenyl, 4-(2,2,2-trifluoro-ethoxy)-phenyl, 4,6-dimethyl-pyrid-3-yl, 4-amino-2-ethyl sulfanyl-pyrimidine-5-yl, 4-amino-2-methyl-pyrimidine-5-yl, 4-chloro-3-methanesulfonylamino-phenyl, 4-chloro-3-sulfamoyl-phenyl, 4-methyl-3-methylamino-phenyl, 4-methyl-thiazole-5-yl, pyridine-2-yl, pyridine-3-yl, pyridine-4-yl, 5-thiophen-2-yl-pyrid-3-yl, 2-methyl-4-trifluoromethyl-thiazol-5-yl, 5,6,7,8-tetrahydro-quinoline-3-yl, 5-amino-1-phenyl-1H-pyrazole-4-yl, 5-methanesulfonyl-2-methyl-phenyl, 5-methyl-1-phenyl-1H-pyrazole-4-yl, 5-methyl-isoxazole-3-yl, 5-methyl-pyrid-3-yl, 5-methyl-pyrazine-2-yl, 6-chloro-pyrid-3-yl, 6-cyano-pyrid-3-yl, 6-dimethylamino-pyrid-3-yl, 6-ethynyl-pyrid-3-yl, 6-methoxymethyl-pyrid-3-yl, 6-methoxy-pyrid-3-yl, 6-methyl-2-methylamino-pyrid-3-yl, 6-methylamino-pyrazine-2-yl, 6-methyl-pyrid-3-yl, 6-morpholin-4-yl-pyrid-3-yl, 6-pyrrolidin-1-yl-pyrid-3-yl, imidazo[1,2-a]pyridine-2-yl, 6-trifluoromethyl-pyrid-3-yl, and pyrimidine-4-yl.

23. The method according to claim 18, wherein the mammal is a human.

24. A method of treating a mammal suffering from a disease chosen from stable and unstable angina pectoris, coronary heart disease, Prinzmetal angina, acute coronary syndrome, heart failure, myocardial infarction, stroke, thrombosis, peripheral artery occlusive disease, endothelial dysfunction, atherosclerosis, restenosis, endothelial damage after PTCA, hypertension, chronic glomerulonephritis, erectile dysfunction, ventricular arrhythmia, diabetes, diabetes complications, angiogenesis, asthma bronchiale, chronic renal failure, cirrhosis of the liver, osteoporosis, diseases with symptoms of restricted memory performance and/or a restricted ability to learn, which method comprises administering to said mammal a physiologically active amount of a compound according to the general formula (I), in any of its stereoisomeric forms or a mixture thereof in any ratio or a pharmaceutically acceptable salt thereof

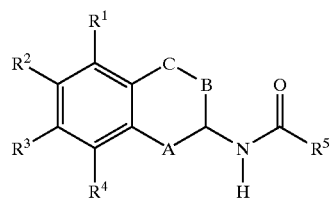

(I)

wherein $R^1$ is H, halogen or $C_1$–$C_4$-alkyl;

$R^2$ and $R^3$ are each H;

$R^4$ independently has the same meaning as $R^1$;

A and B are each $CH_2$;

C is $CH_2$ or CH—$CH_3$;

$R^5$ is chosen from: benzo[1,3]dioxol-5-yl, 2,2-difluoro-benzo[1,3]dioxol-5-yl, 2,3-dihydrobenzofuran-5-yl, 1-(4-chloro-phenyl)-5-trifluoromethyl-1H-pyrazole-4-yl, 1-(4-fluoro-phenyl)-3,5-dimethyl-1H-pyrazole-4-yl, 1H-benzotriazole-5-yl, 1H-indole-4-yl, 1H-indole-6-yl, 1-isopropyl-2-trifluoromethyl-1H-benzoimidazole-5-yl, 1-methyl-3-oxo-1,2,3,4-tetrahydro-quinoxaline-6-yl, 1-phenyl-5-trifluoromethyl-1H-pyrazole-4-yl, 2-(2-hydroxy-pyridin-4-yl)-1H-benzoimidazole-5-yl, 2-(4-cyano-phenyl)-1H-benzoimidazole-5-yl, 2,4-dimethyl-oxazole-5-yl, 2,4-dimethyl-pyrimidine-5-yl, 2,4-dimethyl-thiazole-5-yl, 2,5-dimethyl-1H-pyrrole-3-yl, 2,5-dimethyl-1-phenyl-1H-pyrrole-3-yl, 2,5-dimethyl-1-pyridin-4-ylmethyl-1H-pyrrolyl, 2,5-dimethyl-2H-pyrazole-3-yl, 2,6-dichloro-pyrid-3-yl, 2,6-dimethoxy-pyrid-3-yl, 2,6-dimethyl-pyrid-3-yl, 2-amino-4,6-dimethyl-pyrid-3-yl, 2-amino-6-chloro-pyrid-3-yl, 2-amino-pyrid-3-yl, 2-chloro-6-methyl-pyrid-3-yl, 2-chloro-pyrid-4-yl, 2-cyclopropyl-4-methyl-thiazole-5-yl, 2-dimethylamino-4-methyl-thiazole-5-yl, 2-dimethylamino-pyrid-4-yl, 2-ethyl-5-methyl-2H-pyrazole-3-yl, 2-hydroxy-6-methyl-pyrid-3-yl, 2-methyl-1H-benzoimidazole-5-yl, 2-methyl-3H-benzoimidazole-5-yl, 2-methyl-pyrid-3-yl, 2-methyl-6-trifluoromethyl-pyrid-3-yl, 2-methyl-thiazole-5-yl, 2-morpholin-4-yl-pyridin-4-yl, 2-morpholin-4-yl-pyrimidine-5-yl, 2-pyrrolidin-1-yl-pyridin-4-yl, 3,5-dimethyl-1H-pyrazole-4-yl, 3-amino-5,6-dimethyl-pyrazine-2-yl, 3-amino-5-methyl-pyrazine-2-yl, 3-amino-pyrazine-2-yl, 3H-benzoimidazole-5-yl, 1H-benzoimidazole-5-yl, 3-methyl-isoxazole-4-yl, 4,6-dimethyl-pyrid-3-yl, 4-amino-2-ethylsulfanyl-pyrimidine-5-yl, 4-amino-2-methyl-pyrimidine-5-yl, 4-methyl-thiazole-5-yl, pyridine-2-yl, pyridine-3-yl, pyridine-4-yl, 5-thiophen-2-yl-pyrid-3-yl, 2-methyl-4-trifluoromethyl-thiazol-5-yl, 5,6,7,8-tetrahydro-quinoline-3-yl, 5-amino-1-phenyl-1H-pyrazole-4-yl, 5-methyl-1-phenyl-1H-pyrazole-4-yl, 5-methyl-isoxazole-3-yl, 5-methyl-pyrid-3-yl, 5-methyl-pyrazine-2-yl, 6-chloro-pyrid-3-yl, 6-cyano-pyrid-3-yl, 6-dimethylamino-pyrid-3-yl, 6-ethynyl-pyrid-3-yl, 6-methoxymethyl-pyrid-3-yl, 6-methoxy-pyrid-3-yl, 6-methyl-2-methylamino-pyrid-3-yl, 6-methylamino-pyrazine-2-yl, 6-methyl-pyrid-3-yl, 6-morpholin-4-yl-pyrid-3-yl, 6-pyrrolidin-1-yl-pyrid-3-yl, imidazo[1,2-a]pyridine-2-yl, 6-trifluoromethyl-pyrid-3-yl, and pyrimidine-4-yl.

25. The method according to claim 24, wherein the hypertension is chosen from essential hypertension, pulmonary hypertension, secondary hypertension, and renovascular hypertension.

26. The method according to claim 24, wherein the diabetes complications are chosen from nephropathy and retinopathy.

27. The method according to claim 24, which method lowers cardiovascular risk of postmenopausal women and mammals taking contraceptives.

28. The method according to claim 24, wherein the mammal is a human.

29. A method of treating a mammal suffering from a cardiovascular disease, which method comprises administering to said mammal a physiologically active amount of a compound according to the general formula (I), in any of its stereoisomeric forms or a mixture thereof in any ratio or a pharmaceutically acceptable salt thereof

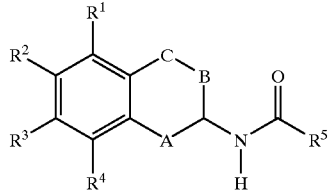

(I)

wherein $R^1$ is H, halogen or $C_1$–$C_4$-alkyl;
$R^2$ and $R^3$ are each H;
$R^4$ independently has the same meaning as $R^1$;
A and B are each $CH_2$;
C is $CH_2$ or CH—$CH_3$;
$R^5$ is chosen from: benzo[1,3]dioxol-5-yl, 2,2-difluoro-benzo[1,3]dioxol-5-yl, 2,3-dihydrobenzofuran-5-yl, 1-(4-chloro-phenyl)-5-trifluoromethyl-1H-pyrazole-4-yl, 1-(4-fluoro-phenyl)-3,5-dimethyl-1H-pyrazole-4-yl, 1H-benzotriazole-5-yl, 1H-indole-4-yl, 1H-indole-6-yl, 1-isopropyl-2-trifluoromethyl-1H-benzoimidazole-5-yl, 1-methyl-3-oxo-1,2,3,4-tetrahydro-quinoxaline-6-yl, 1-phenyl-5-trifluoromethyl-1H-pyrazole-4-yl, 2-(2-hydroxy-pyridin-4-yl)-1H-benzoimidazole-5-yl, 2-(4-cyano-phenyl)-1H-benzoimidazole-5-yl, 2,4-dimethyl-oxazole-5-yl, 2,4-dimethyl-pyrimidine-5-yl, 2,4-dimethyl-thiazole-5-yl, 2,5-dimethyl-1H-pyrrole-3-yl, 2,5-dimethyl-1-phenyl-1H-pyrrole-3-yl, 2,5-dimethyl-1-pyridin-4-ylmethyl-1H-pyrrolyl, 2,5-dimethyl-2H-pyrazole-3-yl, 2,6-dichloro-pyrid-3-yl, 2,6-dimethoxy-pyrid-3-yl, 2,6-dimethyl-pyrid-3-yl, 2-amino-4,6-dimethyl-pyrid-3-yl, 2-amino-6-chloro-pyrid-3-yl, 2-amino-pyrid-3-yl, 2-chloro-6-methyl-pyrid-3-yl, 2-chloro-pyrid-4-yl, 2-cyclopropyl-4-methyl-thiazole-5-yl, 2-dimethylamino-4-methyl-thiazole-5-yl, 2-dimethylamino-pyrid-4-yl, 2-ethyl-5-methyl-2H-pyrazole-3-yl, 2-hydroxy-6-methyl-pyrid-3-yl, 2-methyl-1H-benzoimidazole-5-yl, 2-methyl-3H-benzoimidazole-5-yl, 2-methyl-pyrid-3-yl, 2-methyl-6-trifluoromethyl-pyrid-3-yl, 2-methyl-thiazole-5-yl, 2-morpholin-4-yl-pyridin-4-yl, 2-morpholin-4-yl-pyrimidine-5-yl, 2-pyrrolidin-1-yl-pyridin-4-yl, 3,5-dimethyl-1H-pyrazole-4-yl, 3-amino-5,6-dimethyl-pyrazine-2-yl, 3-amino-5-methyl-pyrazine-2-yl, 3-amino-pyrazine-2-yl, 3H-benzoimidazole-5-yl, 1H-benzoimidazole-5-yl, 3-methyl-isoxazole-4-yl, 4,6-dimethyl-pyrid-3-yl, 4-amino-2-ethylsulfanyl-pyrimidine-5-yl, 4-amino-2-methyl-pyrimidine-5-yl, 4-methyl-thiazole-5-yl, pyridine-2-yl, pyridine-3-yl, pyridine-4-yl, 5-thiophen-2-yl-pyrid-3-yl, 2-methyl-4-trifluoromethyl-thiazol-5-yl, 5,6,7,8-tetrahydro-quinoline-3-yl, 5-amino-1-phenyl-1H-pyrazole-4-yl, 5-methyl-1-phenyl-1H-pyrazole-4-yl, 5-methyl-isoxazole-3-yl, 5-methyl-pyrid-3-yl, 5-methyl-pyrazine-2-yl, 6-chloro-pyrid-3-yl, 6-cyano-pyrid-3-yl, 6-dimethylamino-pyrid-3-yl, 6-ethynyl-pyrid-3-yl, 6-methoxymethyl-pyrid-3-yl, 6-methoxy-pyrid-3-yl, 6-methyl-2-methylamino-pyrid-3-yl, 6-methylamino-pyrazine-2-yl, 6-methyl-pyrid-3-yl, 6-morpholin-4-yl-pyrid-3-yl, 6-pyrrolidin-1-yl-pyrid-3-yl, imidazo[1,2-a]pyridine-2-yl, 6-trifluoromethyl-pyrid-3-yl, and pyrimidine-4-yl.

30. The method according to claim 29, wherein the mammal is a human.

31. A method of treating a mammal suffering from a disease chosen from stable and unstable angina pectoris, coronary heart disease, acute coronary syndrome, heart failure, myocardial infarction, thrombosis, peripheral artery occlusive disease, endothelial dysfunction, atherosclerosis, restenosis, endothelial damage after PTCA, hypertension, and osteoporosis, which method comprises administering to said mammal a physiologically active amount of a compound according to the general formula (I), in any of its stereoisomeric forms or a mixture thereof in any ratio or a pharmaceutically acceptable salt thereof

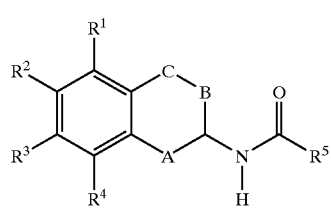

(I)

wherein, in the formula (I),
$R^1$ and $R^4$ are independently from each other chosen from:
H; unsubstituted and at least monosubstituted $C_1$–$C_{10}$-alkyl, $C_2$–$C_{10}$-alkenyl and $C_2$–$C_{10}$-alkynyl, the substituents of which are chosen from F, OH, $C_1$–$C_8$-alkoxy, ($C_1$–$C_8$-alkyl)mercapto, CN, $COOR^6$, $CONR^7R^8$, and unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; $R^9CO$; $CONR^{10}R^{11}$; $COOR^{12}$; $CF_3$; halogens; pseudohalogens; $NR^{13}R^{14}$; $OR^{15}$; $S(O)_mR_{16}$; $SO_2NR^{17}R^{18}$; and $NO_2$;
$R^2$ and $R^3$ are independently from each other chosen from:
H; halogens; pseudohalogens; unsubstituted and at least monosubstituted $C_1$–$C_{10}$-alkyl the substituents of which are chosen from OH, phenyl, and heteroaryl; OH; $C_1$–$C_{10}$-alkoxy; phenoxy; $S(O)_mR^{19}$; $CF_3$; CN; $NO_2$; ($C_1$–$C_{10}$-alkyl)amino; di($C_1$–$C_{10}$-alkyl)amino; ($C_1$–$C_6$-alkyl)-CONH—; unsubstituted and at least monosubstituted phenyl-CONH— and phenyl-$SO_2$—O—, the substituents of which are chosen from halogens, pseudohalogens, $CH_3$ and methoxy; ($C_1$–$C_6$-alkyl)$SO_2$—O—; unsubstituted and at least monosubstituted ($C_1$–$C_6$-alkyl)CO, the substituents of which are chosen from F, di($C_1$–$C_3$-alkyl)amino, pyrrolidinyl and piperidinyl; and phenyl-CO, the phenyl part of which can be substituted by one or more substituents chosen from $C_1$–$C_3$-alkyl, halogens and methoxy;
A is chosen from $CH_2$, CHOH and CH—($C_1$–$C_3$-alkyl);
B is chosen from $CH_2$ and CH—($C_1$–$C_3$-alkyl);
C independently has the same meaning as B;
$R^5$ is a group Ar or a group Hetar both of which can be unsubstituted or carry one or more substituents chosen from: halogens; pseudohalogens; $NH_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, ($C_1$–$C_{10}$- alkyl)amino, and di($C_1$–$C_{10}$-alkyl)amino, the substituents of which are chosen from F, OH, $C_1$–$C_8$-alkoxy, aryloxy, ($C_1$–$C_8$-alkyl)mercapto, $NH_2$, ($C_1$–$C_8$-alkyl)amino, and di($C_1$–$C_8$-alkyl)amino; $C_3$–$C_5$-alkandiyl; phenyl; heteroaryl; aryl-substituted $C_1$–$C_4$-alkyl; heteroaryl-substituted $C_1$–$C_2$-alkyl; $CF_3$; $NO_2$; OH; phenoxy; benzyloxy; ($C_1$–$C_{10}$-alkyl)COO; $S(O)_m R^{20}$; SH; phenylamino; benzylamino; ($C_1$–$C_{10}$-alkyl)-CONH—; ($C_1$–$C_{10}$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_{10}$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; $COOR^{21}$; $CONR^{22}R^{23}$; $CNH(NH_2)$; $SO_2NR^{24}R^{25}$; $R^{26}SO_3NH$—; $R^{27}SO_3N(C_1$–$C_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said group Ar or said group Hetar; and wherein all aryl, heteroaryl, phenyl, aryl-containing, heteroaryl-containing and phenyl-containing groups, which are optionally present in said substituents of said group Ar or said group Hetar, can be substituted by one or more substituents chosen from halogens, pseudohalogens, $C_1$–$C_3$-alkyl, OH, $C_1$–$C_3$-alkoxy, and $CF_3$;

$R^6$ is chosen from:

H; $C_1$–$C_{10}$-alkyl, which can be substituted by one or more substituents chosen from F, $C_1$–$C_8$-alkoxy, and di($C_1$–$C_8$-alkyl)amino; aryl-($C_1$–$C_4$-alkyl) and heteroaryl-($C_1$–$C_4$-alkyl), which can be substituted by one or more substituents chosen from halogens, $C_1$–$C_4$-alkoxy, and di($C_1$–$C_6$-alkyl)amino;

$R^7$ is chosen from:

H; $C_1$–$C_{10}$-alkyl which can be substituted by one or more substituents chosen from F, $C_1$–$C_8$-alkoxy, di($C_1$–$C_8$-alkyl)amino and phenyl; phenyl; indanyl; and heteroaryl; and wherein each of the aforementioned aromatic groups can be unsubstituted or carry one or more substituents chosen from halogens, pseudohalogens, $C_1$–$C_3$-alkyl, $C_1$–$C_3$-alkoxy and $CF_3$;

$R^8$ is H or $C_1$–$C_{10}$-alkyl;

$R^9$ is chosen from: $C_1$–$C_{10}$-alkyl which can be unsubstituted or carry one or more substituents chosen from: F, ($C_1$–$C_4$)-alkoxy, di($C_1$–$C_3$-alkyl)amino; and unsubstituted and at least monosubstituted phenyl and heteroaryl, the substituents of which are chosen from $C_1$–$C_3$-alkyl, $C_1$–$C_3$-alkoxy, halogens, pseudohalogens, and $CF_3$;

$R^{10}$ independently has the same meaning as $R^7$;

$R^{11}$ independently has the same meaning as $R^8$;

$R^{12}$ independently has the same meaning as $R^6$;

$R^{13}$ is chosen from: H; $C_1$–$C_6$-alkyl; unsubstituted and substituted phenyl, benzyl, heteroaryl, ($C_1$–$C_6$-alkyl)-CO, phenyl-CO, and heteroaryl-CO, the substituents of which are chosen from halogens, pseudohalogens, $C_1$–$C_3$-alkyl, $C_1$–$C_3$-alkoxy, and $CF_3$, and wherein one or more of these substituents can be present;

$R^{14}$ independently has the same meaning as $R^{13}$;

$R^{15}$ is chosen from: H; $C_1$–$C_{10}$-alkyl; ($C_1$–$C_3$-alkoxy)-$C_1$–$C_3$-alkyl; and substituted and unsubstituted benzyl, phenyl and heteroaryl, the substituents of which are chosen from halogens, pseudohalogens, $C_1$–$C_3$-alkyl, $C_1$–$C_3$-alkoxy, and $CF_3$, and wherein one or more of these substituents can be present;

$R^{16}$ is chosen from: $C_1$–$C_{10}$-alkyl which can be substituted by one or more substituents chosen from F, OH, $C_1$–$C_8$-alkoxy, aryloxy, ($C_1$–$C_8$-alkyl)mercapto, ($C_1$–$C_8$-alkyl)amino and di($C_1$–$C_8$-alkyl)amino; $CF_3$; and substituted and unsubstituted phenyl and heteroaryl, the substituents of which are chosen from halogens, pseudohalogens, $C_1$–$C_3$-alkyl, $C_1$–$C_3$-alkoxy and $CF_3$, and wherein one or more of these substitutents can be present;

$R^{17}$ independently has the same meaning as $R^7$;

$R^{18}$ independently has the same meaning as $R^8$;

$R^{19}$ independently has the same meaning as $R^{16}$;

$R^{20}$ independently has the same meaning as $R^{16}$;

$R^{21}$ independently has the same meaning as $R^6$;

$R^{22}$ independently has the same meaning as $R^7$;

$R^{23}$ independently has the same meaning as $R^8$;

$R^{24}$ independently has the same meaning as $R^7$;

$R^{25}$ independently has the same meaning as $R^8$;

$R^{26}$ independently has the same meaning as $R^{16}$;

$R^{27}$ independently has the same meaning as $R^{16}$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O, and S;

aryl is phenyl, naphth-1-yl or naphth-2-yl;

the group Ar is phenyl, naphth-1-yl or naphth-2-yl; and m is 0, 1 or 2.

32. The method according to claim 31, wherein the compound according to the general formula (I) is chosen from compounds of the general formula (I), wherein $R^1$ is chosen from: H; $C_1$–$C_4$-alkyl; $C_1$–$C_4$-alkoxy; $CF_3$; halogens; pseudohalogens; ($C_1$–$C_4$-alkyl)-$S(O)_m$—; and unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$, and wherein heteroaryl is chosen from 5- and 6-membered heterocycles containing one or more heteroatoms chosen from N, O, and S;

$R^2$ and $R^3$ are independently from each other chosen from: H; halogens; pseudohalogens; and $C_1$–$C_3$-alkyl;

$R^4$ independently has the same meaning as $R^1$;

A is chosen from $CH_2$ and CHOH;

B and C are independently from each other chosen from $CH_2$ and CH—$CH_3$;

$R^5$ is a group Ar or a group Hetar both of which can be unsubstituted or carry one or more substituents chosen from: halogens; CN; $NH_2$; unsubstituted and at least monosubstituted $C_1$–$C_8$-alkyl, $C_2$–$C_8$-alkenyl, $C_2$–$C_8$-alkynyl, $C_1$–$C_8$-alkoxy, ($C_1$–$C_8$-alkyl)amino, and di($C_1$–$C_8$-alkyl)amino, the substituents of which are chosen from F, $C_1$–$C_6$-alkoxy, phenoxy, ($C_1$–$C_6$-alkyl)mercapto, $NH_2$, ($C_1$–$C_6$-alkyl)amino, and di($C_1$–$C_6$-alkyl)amino; $C_3$–$C_5$-alkandiyl; phenyl; heteroaryl; phenyl-substituted $C_1$–$C_2$-alkyl; $CF_3$; OH; phenoxy; benzyloxy; ($C_1$–$C_6$-alkyl)COO; $S(O)_m(C_1$–$C_6)$-alkyl; $S(O)_m$-phenyl; $S(O)_m$-heteroaryl; SH; phenylamino; benzylamino; ($C_1$–$C_6$-alkyl)-CONH—; ($C_1$–$C_6$-alkyl)-CON($C_1$–$C_4$-alkyl)-; phenyl-CONH—; phenyl-CON ($C_1$–$C_4$-alkyl)-; heteroaryl-CONH—; heteroaryl-CON($C_1$–$C_4$-alkyl)-; ($C_1$–$C_6$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; COO($C_1$–$C_6$-alkyl); —$CONH_2$; —CONH($C_1$–$C_6$-alkyl); —CON(di ($C_1$–$C_6$-alkyl)); CNH($NH_2$); —$SO_2NH_2$; —$SO_2$NH ($C_1$–$C_6$-alkyl); —$SO_2$NH(phenyl); —$SO_2$N(di($C_1$–$C_6$-alkyl)); ($C_1$–$C_6$-alkyl)$SO_2$NH—; ($C_1$–$C_6$-alkyl)$SO_2$N ($C_1$–$C_6$-alkyl)-; phenyl-$SO_2$NH—; phenyl-$SO_2$N ($C_1$–$C_6$-alkyl)-; heteroaryl-$SO_2$NH—; heteroaryl-$SO_2$N($C_1$–$C_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said group Ar or said group Hetar; and wherein all heteroaryl, phenyl, heteroaryl-containing and phenyl-containing groups, which are optionally present in said substituents of said group Ar or said group Hetar, can be substituted by one or more substituents chosen from halogens, pseudohalogens, $C_1$–$C_3$-alkyl, OH, $C_1$–$C_3$-alkoxy, and $CF_3$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O, and S;

the group Ar is phenyl, naphth-1-yl or naphth-2-yl; and m is 0 or 2.

33. The method according to claim 31, wherein the compound according to the general formula (I) is chosen from the compounds of the general formula (I), wherein $R^1$ is H, halogen, or $C_1$–$C_4$-alkyl;

$R^2$ and $R^3$ are each H;

$R^4$ independently has the same meaning as $R^1$;

A is $CH_2$;

$R^5$ is phenyl or a group Hetar both of which can be unsubstituted or carry one or more substituents chosen from: halogens; CN; $NH_2$; unsubstituted and at least monosubstituted $C_1$–$C_6$-alkyl, $C_2$–$C_6$-alkenyl, $C_2$–$C_6$-alkynyl, $C_1$–$C_3$-alkoxy, ($C_1$–$C_4$-alkyl)amino, and di($C_1$–$C_4$-alkyl)amino, the substituents of which are chosen from F, $C_1$–$C_3$-alkoxy, ($C_1$–$C_3$-alkyl)mercapto, and $NH_2$; $C_3$–$C_5$-alkandiyl; phenyl; heteroaryl; phenyl-substituted $C_1$–$C_2$-alkyl; heteroaryl-substituted $C_1$–$C_2$-alkyl; $CF_3$; OH; ($C_1$–$C_4$-alkyl)COO; $S(O)_m$($C_1$–$C_4$)-alkyl; ($C_1$–$C_4$-alkyl)-CONH—; ($C_1$–$C_4$-alkyl)-CON ($C_1$–$C_4$-alkyl)-; ($C_1$–$C_4$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; COO($C_1$–$C_6$-alkyl); —$CONH_2$; —CONH($C_1$–$C_4$-alkyl); —CON(di ($C_1$–$C_4$-alkyl)); CNH($NH_2$); —$SO_2NH_2$; —$SO_2$NH ($C_1$–$C_4$-alkyl); —$SO_2$NH(phenyl); —$SO_2$N(di($C_1$–$C_4$-alkyl)); ($C_1$–$C_4$-alkyl)$SO_2$NH—; ($C_1$–$C_4$-alkyl)$SO_2$N ($C_1$–$C_4$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said phenyl or said group Hetar; and wherein all heteroaryl, phenyl, heteroaryl-containing and phenyl-containing groups, which are optionally present in said substituents of said phenyl or said group Hetar, can be substituted by one or more substituents; chosen from halogens, pseudohalogens, $C_1$–$C_3$-alkyl, OH, $C_1$–$C_3$-alkoxy, and $CF_3$;

heteroaryl is a 5 to 10-membered, aromatic, mono- or bicyclic heterocycle containing one, two or three heteroatoms chosen from N, O, and S;

the group Hetar is a 5 to 10-membered, aromatic, mono- or bicyclic heterocycle containing one, two or three heteroatoms chosen from N, O, and S; and m is 0 or 2.

34. The method according to claim 31, wherein the compound according to the general formula (I) is chosen from the compounds of the general formula (I) wherein $R^1$ is H, halogen, or $C_1$–$C_4$-alkyl;

$R^2$ and $R^3$ are each H;

$R^4$ independently has the same meaning as $R^1$;

A and B are each $CH_2$;

C is $CH_2$ or CH—$CH_3$;

$R^5$ is phenyl or a group Hetar both of which can be unsubstituted or carry one or more substituents chosen from: F; Cl; Br; $C_1$–$C_3$-alkyl; $C_1$–$C_3$-alkoxymethyl; 2-amino-3,3,3-trifluoro-propyl-; $CF_3$; $C_3$–$C_5$-alkandiyl; phenyl; heteroaryl; benzyl; heteroarylmethyl; OH; $C_1$–$C_3$-alkoxy; phenoxy; trifluoromethoxy; 2,2,2-trifluoroethoxy; ($C_1$–$C_4$-alkyl)COO; ($C_1$–$C_3$-alkyl)mercapto; phenylmercapto; ($C_1$–$C_3$-alkyl)sulfonyl; phenylsulfonyl; $NH_2$; ($C_1$–$C_4$-alkyl) amino; di($C_1$–$C_4$-alkyl)amino; ($C_1$–$C_3$-alkyl)-CONH—; ($C_1$–$C_3$-alkyl)-$SO_2$NH—; ($C_1$–$C_3$-alkyl)-CO; phenyl-CO; —$OCH_2O$—; —$OCF_2O$—; —$CH_2CH_2O$—; COO($C_1$–$C_4$-alkyl); —$CONH_2$; —CONH($C_1$–$C_4$-alkyl); —CON(di($C_1$–$C_4$-alkyl)); CN; —$SO_2NH_2$; —$SO_2$NH($C_1$–$C_4$-alkyl); —$SO_2$N(di ($C_1$–$C_4$-alkyl)); pyrrolidinyl; piperidinyl; morpholinyl; and thiomorpholinyl; and wherein all heteroaryl, phenyl, heteroaryl-containing and phenyl-containing groups, which are optionally present in said substituents of said phenyl or said group Hetar, can be substituted by one or more substituents chosen from halogens, pseudohalogens, $C_1$–$C_3$-alkyl, OH, $C_1$–$C_3$-alkoxy, and $CF_3$;

heteroaryl is chosen from: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl;

the group Hetar is chosen from: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl.

35. The method according to claim 31, wherein the compound according to the general formula (I) is chosen from the compounds of the general formula (I) wherein $R^1$ is H, halogen or $C_1$–$C_4$-alkyl;

$R^2$ and $R^3$ are each H;

$R^4$ independently has the same meaning as $R^1$;

A and B are each $CH_2$;

C is $CH_3$ or $CH$—$CH_3$;

$R^5$ is chosen from: 4-fluorophenyl, 4-chlorophenyl, 4-bromophenyl, 4-($C_1$–$C_3$-alkoxy)-phenyl, 4-trifluoromethoxyphenyl, 2-bromo-4-fluorophenyl, 2-chloro-4-fluorophenyl, 3,4-dimethylphenyl, 2,4-dimethylphenyl, 4-chloro-2-methylphenyl, 2-hydroxy-4-methylphenyl, 2-hydroxy-4-ethoxyphenyl, 2-methoxy-4-methylphenyl, 4-phenoxyphenyl, 3-fluoro-4-methylphenyl, benzo[1,3]dioxol-5-yl, 2,2-difluoro-benzo[1,3]dioxol-5-yl, 2,3-dihydrobenzofuran-5-yl, 1-(4-chloro-phenyl)-5-trifluoromethyl-1H-pyrazole-4-yl, 1-(4-fluoro-phenyl)-3,5-dimethyl-1H-pyrazole-4-yl, 1H-benzotriazole-5-yl, 1H-indole-4-yl, 1H-indole-6-yl, 1-isopropyl-2-trifluoromethyl-1H-benzoimidazole-5-yl, 1-methyl-3-oxo-1,2,3,4-tetrahydro-quinoxaline-6-yl, 1-phenyl-5-trifluoromethyl-1H-pyrazole-4-yl, 2-(2-hydroxy-pyridin-4-yl)-1H-benzoimidazole-5-yl, 2-(4-cyano-phenyl)-1H-benzoimidazole-5-yl, 2,4-dimethyl-oxazole-5-yl, 2,4-dimethyl-pyrimidine-5-yl, 2,4-dimethyl-thiazole-5-yl, 2,5-dimethyl-1H-pyrrole-3-yl, 2,5-dimethyl-1-phenyl-1H-pyrrole-3-yl, 2,5-dimethyl-1-pyridin-4-ylmethyl-1H-pyrrolyl, 2,5-dimethyl-2H-pyrazole-3-yl, 2,6-dichloro-pyrid-3-yl, 2,6-dimethoxy-pyrid-3-yl, 2,6-dimethyl-pyrid-3-yl, 2-amino-4,6-dimethyl-pyrid-3-yl, 2-amino-6-chloro-pyrid-3-yl, 2-amino-pyrid-3-yl, 2-chloro-6-methyl-pyrid-3-yl, 2-chloro-pyrid-4-yl, 2-cyclopropyl-4-methyl-thiazole-5-yl, 2-dimethylamino-4-methyl-thiazole-5-yl, 2-dimethylamino-pyrid-4-yl, 2-ethyl-5-methyl-2H-pyrazole-3-yl, 2-hydroxy-6-methyl-pyrid-3-yl, 2-methyl-1H-benzoimidazole-5-yl, 2-methyl-3H-benzoimidazole-5-yl, 2-methyl-pyrid-3-yl, 2-methyl-6-trifluoromethyl-pyrid-3-yl, 2-methyl-thiazole-5-yl, 2-morpholin-4-yl-pyridin-4-yl, 2-morpholin-4-yl-pyrimidine-5-yl, 2-pyrrolidin-1-yl-pyridin-4-yl, 3,5-dimethyl-1H-pyrazole-4-yl, 3-amino-5,6-dimethyl-pyrazine-2-yl, 3-amino-5-methyl-pyrazine-2-yl, 3-amino-pyrazine-2-yl, 3-dimethylamino-4-methyl-phenyl, 3-dimethylamino-phenyl, 3H-benzoimidazole-5-yl, 1H-benzoimidazole-5-yl, 3-methanesulfonylamino-2-methyl-phenyl, 3-methanesulfonylamino-phenyl, 3-methyl-isoxazole-4-yl, 3-morpholin-4-yl-phenyl, 3-piperidin-1-yl-phenyl, 3-pyrrolidin-1-yl-phenyl, 4-(2,2,2-trifluoro-ethoxy)-phenyl, 4,6-dimethyl-pyrid-3-yl, 4-amino-2-ethyl sulfanyl-pyrimidine-5-yl, 4-amino-2-methyl-pyrimidine-5-yl, 4-chloro-3-methanesulfonylamino-phenyl, 4-chloro-3-sulfamoyl-phenyl, 4-methyl-3-methylamino-phenyl, 4-methyl-thiazole-5-yl, pyridine-2-yl, pyridine-3-yl, pyridine-4-yl, 5-thiophen-2-yl-pyrid-3-yl, 2-methyl-4-trifluoromethyl-thiazol-5-yl, 5,6,7,8-tetrahydro-quinoline-3-yl, 5-amino-1-phenyl-1H-pyrazole-4-yl, 5-methanesulfonyl-2-methyl-phenyl, 5-methyl-1-phenyl-1H-pyrazole-4-yl, 5-methyl-isoxazole-3-yl, 5-methyl-pyrid-3-yl, 5-methyl-pyrazine-2-yl, 6-chloro-pyrid-3-yl, 6-cyano-pyrid-3-yl, 6-dimethylamino-pyrid-3-yl, 6-ethynyl-pyrid-3-yl, 6-methoxymethyl-pyrid-3-yl, 6-methoxy-pyrid-3-yl, 6-methyl-2-methylamino-pyrid-3-yl, 6-methylamino-pyrazine-2-yl, 6-methyl-pyrid-3-yl, 6-morpholin-4-yl-pyrid-3-yl, 6-pyrrolidin-1-yl-pyrid-3-yl, imidazo[1,2-a]pyridine-2-yl, 6-trifluoromethyl-pyrid-3-yl, and pyrimidine-4-yl.

36. The method according to claim 31, wherein the mammal is a human.

37. A method of treating a mammal suffering from a cardiovascular disease, which method comprises administering to said mammal a physiologically active amount of a compound according to the general formula (I), in any of its stereoisomeric forms or a mixture thereof in any ratio or a pharmaceutically acceptable salt thereof

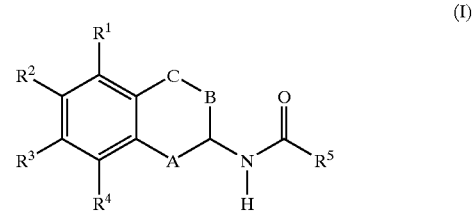

(I)

wherein, in the formula (I), $R^1$ and $R^4$ are independently from each other chosen from:

H; unsubstituted and at least monosubstituted $C_1$–$C_{10}$-alkyl, $C_2$–$C_{10}$-alkenyl and $C_2$–$C_{10}$-alkynyl, the substituents of which are chosen from F, OH, $C_1$–$C_8$-alkoxy, ($C_1$–$C_8$-alkyl)mercapto, CN, $COOR^6$, $CONR^7R^8$, and unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$; $R^9CO$; $CONR^{10}R^{11}$; $COOR^{12}$; $CF_3$; halogens; pseudohalogens; $NR^{13}R^{14}$; $OR^{15}$; $S(O)_mR_{16}$; $SO_2NR^{17}R^{18}$; and $NO_2$;

$R^2$ and $R^3$ are independently from each other chosen from:

H; halogens; pseudohalogens; unsubstituted and at least monosubstituted $C_1$–$C_{10}$-alkyl the substituents of which are chosen from OH, phenyl, and heteroaryl; OH; $C_1$–$C_{10}$-alkoxy; phenoxy; $S(O)_mR^{19}$; $CF_3$; CN; $NO_2$; ($C_1$–$C_{10}$-alkyl)amino; di($C_1$–$C_{10}$-alkyl)amino; ($C_1$–$C_6$-alkyl)-CONH—; unsubstituted and at least monosubstituted phenyl-CONH— and phenyl-$SO_2$—O—, the substituents of which are chosen from halogens, pseudohalogens, $CH_3$ and methoxy; ($C_1$–$C_6$-alkyl)$SO_2$—O—; unsubstituted and at least monosubstituted ($C_1$–$C_6$-alkyl)CO, the substituents of which are chosen from F, di($C_1$–$C_3$-alkyl)amino, pyrrolidinyl and piperidinyl; and phenyl-CO, the phenyl part of which can be substituted by one or more substituents chosen from $C_1$–$C_3$-alkyl, halogens and methoxy;

A is chosen from $CH_2$, CHOH and CH—($C_1$–$C_3$-alkyl);

B is chosen from $CH_2$ and CH—($C_1$–$C_3$-alkyl);

C independently has the same meaning as B;

$R^5$ is a group Ar or a group Hetar both of which can be unsubstituted or carry one or more substituents chosen from: halogens; pseudohalogens; $NH_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, ($C_1$–$C_{10}$-alkyl)amino, and di($C_1$–$C_{10}$-alkyl)amino, the substituents of which are chosen from F, OH, $C_1$–$C_8$-alkoxy, aryloxy, ($C_1$–$C_8$-alkyl)mercapto, $NH_2$, ($C_1$–$C_8$-alkyl)amino, and di($C_1$–$C_8$-alkyl)amino; $C_3$–$C_5$-alkandiyl; phenyl; heteroaryl; aryl-substituted $C_1$–$C_4$-alkyl; heteroaryl-substituted $C_1$–$C_2$-alkyl; $CF_3$; $NO_2$; OH; phenoxy; benzyloxy; ($C_1$–$C_{10}$-alkyl)COO; $S(O)_mR^{20}$; SH; phenylamino; benzylamino; ($C_1$–$C_{10}$-alkyl)-CONH—; ($C_1$–$C_{10}$-alkyl)-CON($C_1$–$C_4$-alkyl)-;

phenyl-CONH—; phenyl-CON($C_1$–$C_4$-alkyl)-; heteroaryl-CONH—; heteroaryl-CON($C_1$–$C_4$-alkyl)-; ($C_1$–$C_{10}$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; $COOR^{21}$; $CONR^{22}R^{23}$; $CNH(NH_2)$; $SO_2NR^{24}R^{25}$; $R^{26}SO_2NH$—; $R^{27}SO_2N(C_1$–$C_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, $C_1$–$C_3$-alkyl, $C_1$–$C_3$-alkoxy, OH, oxo and $CF_3$, and wherein said heterocycles can optionally be condensed to said group Ar or said group Hetar; and wherein all aryl, heteroaryl, phenyl, aryl-containing, heteroaryl-containing and phenyl-containing groups, which are optionally present in said substituents of said group Ar or said group Hetar, can be substituted by one or more substituents chosen from halogens, pseudohalogens, $C_1$–$C_3$-alkyl, OH, $C_1$–$C_3$-alkoxy, and $CF_3$;

$R^6$ is chosen from:

H; $C_1$–$C_{10}$-alkyl, which can be substituted by one or more substituents chosen from F, $C_1$–$C_8$-alkoxy, and di($C_1$–$C_8$-alkyl)amino; aryl-($C_1$–$C_4$-alkyl) and heteroaryl-($C_1$–$C_4$-alkyl), which can be substituted by one or more substituents chosen from halogens, $C_1$–$C_4$-alkoxy, and di($C_1$–$C_6$-alkyl)amino;

$R^7$ is chosen from:

H; $C_1$–$C_{10}$-alkyl which can be substituted by one or more substituents chosen from F, $C_1$–$C_8$-alkoxy, di($C_1$–$C_8$-alkyl)amino and phenyl; phenyl; indanyl; and heteroaryl; and wherein each of the aforementioned aromatic groups can be unsubstituted or carry one or more substituents chosen from halogens, pseudohalogens, $C_1$–$C_3$-alkyl, $C_1$–$C_3$-alkoxy and $CF_3$;

$R^8$ is H or $C_1$–$C_{10}$-alkyl;

$R^9$ is chosen from: $C_1$–$C_{10}$-alkyl which can be unsubstituted or carry one or more substituents chosen from: F, ($C_1$–$C_4$)-alkoxy, di($C_1$–$C_3$-alkyl)amino; and unsubstituted and at least monosubstituted phenyl and heteroaryl, the substituents of which are chosen from $C_1$–$C_3$-alkyl, $C_1$–$C_3$-alkoxy, halogens, pseudohalogens, and $CF_3$;

$R^{10}$ independently has the same meaning as $R^7$;

$R^{11}$ independently has the same meaning as $R^8$;

$R^{12}$ independently has the same meaning as $R^6$;

$R^{13}$ is chosen from: H; $C_1$–$C_6$-alkyl; unsubstituted and substituted phenyl, benzyl, heteroaryl, ($C_1$–$C_6$-alkyl)-CO, phenyl-CO, and heteroaryl-CO, the substituents of which are chosen from halogens, pseudohalogens, $C_1$–$C_3$-alkyl, $C_1$–$C_3$-alkoxy, and $CF_3$, and wherein one or more of these substituents can be present;

$R^{14}$ independently has the same meaning as $R^{13}$;

$R^{15}$ is chosen from: H; $C_1$–$C_{10}$-alkyl; ($C_1$–$C_3$-alkoxy)-$C_1$–$C_3$-alkyl; and substituted and unsubstituted benzyl, phenyl and heteroaryl, the substituents of which are chosen from halogens, pseudohalogens, $C_1$–$C_3$-alkyl, $C_1$–$C_3$-alkoxy, and $CF_3$, and wherein one or more of these substituents can be present;

$R^{16}$ is chosen from: $C_1$–$C_{10}$-alkyl which can be substituted by one or more substituents chosen from F, OH, $C_1$–$C_8$-alkoxy, aryloxy, ($C_1$–$C_8$-alkyl)mercapto, ($C_1$–$C_8$-alkyl)amino and di($C_1$–$C_8$-alkyl)amino; $CF_3$; and substituted and unsubstituted phenyl and heteroaryl, the substituents of which are chosen from halogens, pseudohalogens, $C_1$–$C_3$-alkyl, $C_1$–$C_3$-alkoxy and $CF_3$, and wherein one or more of these substituents can be present;

$R^{17}$ independently has the same meaning as $R^7$;
$R^{18}$ independently has the same meaning as $R^8$;
$R^{19}$ independently has the same meaning as $R^{16}$;
$R^{20}$ independently has the same meaning as $R^{16}$;
$R^{21}$ independently has the same meaning as $R^6$;
$R^{22}$ independently has the same meaning as $R^7$;
$R^{23}$ independently has the same meaning as $R^8$;
$R^{24}$ independently has the same meaning as $R^7$;
$R^{25}$ independently has the same meaning as $R^8$;
$R^{26}$ independently has the same meaning as $R^{16}$;
$R^{27}$ independently has the same meaning as $R^{16}$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O, and S;

aryl is phenyl, naphth-1-yl or naphth-2-yl;

the group Ar is phenyl, naphth-1-yl or naphth-2-yl; and m is 0, 1 or 2.

38. The method according to claim 37, wherein the compound according to the general formula (I) is chosen from compounds of the general formula (I), wherein $R^1$ is chosen from: H; $C_1$–$C_4$-alkyl; $C_1$–$C_4$-alkoxy; $CF_3$; halogens; pseudohalogens; ($C_1$–$C_4$-alkyl)-$S(O)_m$—; and unsubstituted and at least monosubstituted phenyl and heteroaryl, the substituents of which are chosen from halogens, pseudohalogens, $C_1$–$C_3$-alkyl, $C_1$–$C_3$-alkoxy and $CF_3$, and wherein heteroaryl is chosen from 5- and 6-membered heterocycles containing one or more heteroatoms chosen from N, O, and S;

$R^2$ and $R^3$ are independently from each other chosen from: H; halogens; pseudohalogens; and $C_1$–$C_3$-alkyl;

$R^4$ independently has the same meaning as $R^1$;

A is chosen from $CH_2$ and CHOH;

B and C are independently from each other chosen from $CH_2$ and CH—$CH_3$;

$R^5$ is a group Ar or a group Hetar both of which can be unsubstituted or carry one or more substituents chosen from: halogens; CN; $NH_2$; unsubstituted and at least monosubstituted $C_1$–$C_8$-alkyl, $C_2$–$C_8$-alkenyl, $C_2$–$C_8$-alkynyl, $C_1$–$C_8$-alkoxy, ($C_1$–$C_8$-alkyl)amino, and di($C_1$–$C_8$-alkyl)amino, the substituents of which are chosen from F, $C_1$–$C_6$-alkoxy, phenoxy, ($C_1$–$C_6$-alkyl) mercapto, $NH_2$, ($C_1$–$C_6$-alkyl)amino, and di($C_1$–$C_6$-alkyl)amino; $C_3$–$C_5$-alkandiyl; phenyl; heteroaryl; phenyl-substituted $C_1$–$C_2$-alkyl; heteroaryl-substituted $C_1$–$C_2$-alkyl; $CF_3$; OH; phenoxy; benzyloxy; ($C_1$–$C_6$-alkyl)COO; $S(O)_m$($C_1$–$C_6$)-alkyl; $S(O)_m$-phenyl; $S(O)_m$-heteroaryl; SH; phenylamino; benzylamino; ($C_1$–$C_6$-alkyl)-CONH—; ($C_1$–$C_6$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_6$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; COO($C_1$–$C_6$-alkyl); —$CONH_2$; —CONH($C_1$–$C_6$-alkyl); —CON(di($C_1$–$C_6$-alkyl)); $CNH(NH_2)$; —$SO_2NH_2$; —$SO_2NH(C_1$–$C_6$-alkyl); —$SO_2NH(phenyl)$; —$SO_2N(di(C_1$–$C_6$-alkyl))$; ($C_1$–$C_6$-alkyl)$SO_2NH$—; ($C_1$–$C_6$-alkyl)$SO_2N(C_1$–$C_6$- alkyl)-; phenyl-SO$_2$NH—; phenyl-SO$_2$N(C$_1$–C$_6$-alkyl)-; heteroaryl-SO$_2$NH—; heteroaryl-SO$_2$N(C$_1$–C$_6$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, C$_1$–C$_3$-alkyl, C$_1$–C$_3$-alkoxy, OH, oxo and CF$_3$, and wherein said heterocycles can optionally be condensed to said group Ar or said group Hetar; and wherein all heteroaryl, phenyl, heteroaryl-containing and phenyl-containing groups, which are optionally present in said substituents of said group Ar or said group Hetar, can be substituted by one or more substituents chosen from halogens, pseudohalogens, C$_1$–C$_3$-alkyl, OH, C$_1$–C$_3$-alkoxy, and CF$_3$;

heteroaryl is a 5 to 10-membered, aromatic, mono- or bicyclic heterocycle containing one or more heteroatoms chosen from N, O, and S;

the group Hetar is a 5 to 10-membered, aromatic, mono- or bicyclic heterocycle containing one or more heteroatoms chosen from N, O, and S;

the group Ar is phenyl, naphth-1-yl or naphth-2-yl; and m is 0 or 2.

39. The method according to claim 37, wherein the compound according to the general formula (I) is chosen from the compounds of the general formula (I), wherein R$^1$ is H, halogen, or C$_1$–C$_4$-alkyl;

R$^2$ and R$^3$ are each H;

R$^4$ independently has the same meaning as R$^1$;

A is CH$_2$;

R$^5$ is phenyl or a group Hetar both of which can be unsubstituted or carry one or more substituents chosen from: halogens; CN; NH$_2$; unsubstituted and at least monosubstituted C$_1$–C$_6$-alkyl, C$_2$–C$_6$-alkenyl, C$_2$–C$_6$-alkynyl, C$_1$–C$_3$-alkoxy, (C$_1$–C$_4$-alkyl)amino, and di(C$_1$–C$_4$-alkyl)amino, the substituents of which are chosen from F, C$_1$–C$_3$-alkoxy, (C$_1$–C$_3$-alkyl)mercapto, and NH$_2$; C$_3$–C$_5$-alkandiyl; phenyl; heteroaryl; phenyl-substituted C$_1$–C$_2$-alkyl; CF$_3$; OH; (C$_1$–C$_4$-alkyl)COO; S(O)$_m$(C$_1$–C$_4$)-alkyl; (C$_1$–C$_4$-alkyl)-CONH—; (C$_1$–C$_4$-alkyl)-CON(C$_1$–C$_4$-alkyl)-; (C$_1$–C$_4$-alkyl)-CO; phenyl-CO; heteroaryl-CO; CF$_3$—CO; —OCH$_2$O—; —OCF$_2$O—; —OCH$_2$CH$_2$O—; —CH$_2$CH$_2$O—; COO(C$_1$–C$_6$-alkyl); —CONH$_2$; —CONH(C$_1$–C$_4$-alkyl); —CON(di(C$_1$–C$_4$-alkyl)); CNH(NH$_2$); —SO$_2$NH$_2$; —SO$_2$NH(C$_1$–C$_4$-alkyl); —SO$_2$NH(phenyl); —SO$_2$N(di(C$_1$–C$_4$-alkyl)); (C$_1$–C$_4$-alkyl)SO$_2$NH—; (C$_1$–C$_4$-alkyl)SO$_2$N(C$_1$–C$_4$-alkyl)-; and saturated and at least monounsaturated aliphatic, mononuclear 5- to 7-membered heterocycles containing 1 to 3 heteroatoms chosen from N, O, and S, which heterocycles can be substituted by one or more substituents chosen from halogens, C$_1$–C$_3$-alkyl, C$_1$–C$_3$-alkoxy, OH, oxo and CF$_3$, and wherein said heterocycles can optionally be condensed to said phenyl or said group Hetar; and wherein all heteroaryl, phenyl, heteroaryl-containing and phenyl-containing groups, which are optionally present in said substituents of said phenyl or said group Hetar, can be substituted by one or more substituents; chosen from halogens, pseudohalogens, C$_1$–C$_3$-alkyl, OH, C$_1$–C$_3$-alkoxy, and CF$_3$;

heteroaryl is a 5 to 10-membered, aromatic, mono- or bicyclic heterocycle containing one, two or three heteroatoms chosen from N, O, and S;

the group Hetar is a 5 to 10-membered, aromatic, mono- or bicyclic heterocycle containing one, two or three heteroatoms chosen from N, O, and S; and m is 0 or 2.

40. The method according to claim 37, wherein the compound according to the general formula (I) is chosen from the compounds of the general formula (I) wherein R$^1$ is H, halogen, or C$_1$–C$_4$-alkyl;

R$^2$ and R$^3$ are each H;

R$^4$ independently has the same meaning as R$^1$;

A and B are each CH$_2$;

C is CH$_2$ or CH—CH$_3$;

R$^5$ is phenyl or a group Hetar both of which can be unsubstituted or carry one or more substituents chosen from: F; Cl; Br; C$_1$–C$_3$-alkyl; C$_1$–C$_3$-alkoxymethyl; 2-amino-3,3,3-trifluoro-propyl-; CF$_3$; C$_3$–C$_5$-alkandiyl; phenyl; heteroaryl; benzyl; heteroarylmethyl; OH; C$_1$–C$_3$-alkoxy; phenoxy; trifluoromethoxy; 2,2,2-trifluoroethoxy; (C$_1$–C$_4$-alkyl)COO; (C$_1$–C$_3$-alkyl)mercapto; phenylmercapto; (C$_1$–C$_3$-alkyl)sulfonyl; phenylsulfonyl; NH$_2$; (C$_1$–C$_4$-alkyl)amino; di(C$_1$–C$_4$-alkyl)amino; (C$_1$–C$_3$-alkyl)-CONH—; (C$_1$–C$_3$-alkyl)-SO$_2$NH—; (C$_1$–C$_3$-alkyl)-CO; phenyl-CO; —OCH$_2$O—; —OCF$_2$O—; —CH$_2$CH$_2$O—; COO(C$_1$–C$_4$-alkyl); —CONH$_2$; —CONH(C$_1$–C$_4$-alkyl); —CON(di(C$_1$–C$_4$-alkyl)); CN; —SO$_2$NH$_2$; —SO$_2$NH(C$_1$–C$_4$-alkyl); —SO$_2$N(di(C$_1$–C$_4$-alkyl)); pyrrolidinyl; piperidinyl; morpholinyl; and thiomorpholinyl; and wherein all heteroaryl, phenyl, heteroaryl-containing and phenyl-containing groups, which are optionally present in said substituents of said phenyl or said group Hetar, can be substituted by one or more substituents chosen from halogens, pseudohalogens, C$_1$–C$_3$-alkyl, OH, C$_1$–C$_3$-alkoxy, and CF$_3$;

heteroaryl is chosen from: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl;

the group Hetar is chosen from: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl.

41. The method according to claim 37, wherein the compound according to the general formula (I) is chosen from the compounds of the general formula (I) wherein R$^1$ is H, halogen or C$_1$–C$_4$-alkyl;

R$^2$ and R$^3$ are each H;

R$^4$ independently has the same meaning as R$^1$;

A and B are each CH$_2$;

C is CH$_2$ or CH—CH$_3$;

R$^5$ is chosen from: 4-fluorophenyl, 4-chlorophenyl, 4-bromophenyl, 4-(C$_1$–C$_3$-alkoxy)-phenyl, 4-trifluoromethoxyphenyl, 2-bromo-4-fluorophenyl, 2-chloro-4-fluorophenyl, 3,4-dimethylphenyl, 2,4-dimethylphenyl, 4-chloro-2-methylphenyl, 2-hydroxy-4-methylphenyl, 2-hydroxy-4-ethoxyphenyl, 2-methoxy-4-methylphenyl, 4-phenoxyphenyl, 3-fluoro-4-methylphenyl, benzo[1,3]dioxol-5-yl, 2,2-difluoro-benzo[1,3]dioxol-5-yl, 2,3-dihydrobenzofuran-5-yl, 1-(4-chloro-phenyl)-5-trifluoromethyl-1H-pyrazole-4-yl, 1-(4-fluoro-phenyl)-3,5-dimethyl-1H-pyrazole-4-yl, 1H-benzotriazole-5-yl, 1H-indole-4-yl, 1H-indole-6-yl, 1-isopropyl-2-trifluoromethyl-1H-benzoimidazole-5-yl, 1-methyl-3-oxo-1,2,3,4-tetrahydro-quinoxaline-6-yl, 1-phenyl-5-trifluoromethyl-1H-pyrazole-4-yl, 2-(2-hydroxy-pyridin-4-yl)-1H-benzoimidazole-5-yl, 2-(4-cyano-phenyl)-1H-benzoimidazole-5-yl, 2,4-dimethyl-oxazole-5-yl, 2,4-dimethyl-pyrimidine-5-yl, 2,4-dimethyl-thiazole-5-yl, 2,5-dimethyl-1H-pyrrole-3-yl, 2,5-dimethyl-1-phenyl-1H-pyrrole-3-yl, 2,5-dimethyl-1-pyridin-4-ylmethyl-1H-pyrrolyl, 2,5-dimethyl-2H-pyrazole-3-yl, 2,6-dichloro-pyrid-3-yl, 2,6-dimethoxy-pyrid-3-yl, 2,6-dimethyl-pyrid-3-yl, 2-amino-4,6-dimethyl-pyrid-3-yl, 2-amino-6-chloro-pyrid-3-yl, 2-amino-pyrid-3-yl, 2-chloro-6-methyl-pyrid-3-yl, 2-chloro-pyrid-4-yl, 2-cyclopropyl-4-methyl-thiazole-5-yl, 2-dimethylamino-4-methyl-thiazole-5-yl, 2-dimethylamino-pyrid-4-yl, 2-ethyl-5-methyl-2H-pyrazole-3-yl, 2-hydroxy-6-methyl-pyrid-3-yl, 2-methyl-1H-benzoimidazole-5-yl, 2-methyl-3H-benzoimidazole-5-yl, 2-methyl-pyrid-3-yl, 2-methyl-6-trifluoromethyl-pyrid-3-yl, 2-methyl-thiazole-5-yl, 2-morpholin-4-yl-pyridin-4-yl, 2-morpholin-4-yl-pyrimidine-5-yl, 2-pyrrolidin-1-yl-pyridin-4-yl, 3,5-dimethyl-1H-pyrazole-4-yl, 3-amino-5,6-dimethyl-pyrazine-2-yl, 3-amino-5-methyl-pyrazine-2-yl, 3-amino-pyrazine-2-yl, 3-dimethylamino-4-methyl-phenyl, 3-dimethylamino-phenyl, 3H-benzoimidazole-5-yl, 1H-benzoimidazole-5-yl, 3-methanesulfonylamino-2-methyl-phenyl, 3-methanesulfonylamino-phenyl, 3-methyl-isoxazole-4-yl, 3-morpholin-4-yl-phenyl, 3-piperidin-1-yl-phenyl, 3-pyrrolidin-1-yl-phenyl, 4-(2,2,2-trifluoro-ethoxy)-phenyl, 4,6-dimethyl-pyrid-3-yl, 4-amino-2-ethyl sulfanyl-pyrimidine-5-yl, 4-amino-2-methyl-pyrimidine-5-yl, 4-chloro-3-methanesulfonylamino-phenyl, 4-chloro-3-sulfamoyl-phenyl, 4-methyl-3-methylamino-phenyl, 4-methyl-thiazole-5-yl, pyridine-2-yl, pyridine-3-yl, pyridine-4-yl, 5-thiophen-2-yl-pyrid-3-yl, 2-methyl-4-trifluoromethyl-thiazol-5-yl, 5,6,7,8-tetrahydro-quinoline-3-yl, 5-amino-1-phenyl-1H-pyrazole-4-yl, 5-methanesulfonyl-2-methyl-phenyl, 5-methyl-1-phenyl-1H-pyrazole-4-yl, 5-methyl-isoxazole-3-yl, 5-methyl-pyrid-3-yl, 5-methyl-pyrazine-2-yl, 6-chloro-pyrid-3-yl, 6-cyano-pyrid-3-yl, 6-dimethylamino-pyrid-3-yl, 6-ethynyl-pyrid-3-yl, 6-methoxymethyl-pyrid-3-yl, 6-methoxy-pyrid-3-yl, 6-methyl-2-methylamino-pyrid-3-yl, 6-methylamino-pyrazine-2-yl, 6-methyl-pyrid-3-yl, 6-morpholin-4-yl-pyrid-3-yl, 6-pyrrolidin-1-yl-pyrid-3-yl, imidazo[1,2-a]pyridine-2-yl, 6-trifluoromethyl-pyrid-3-yl, and pyrimidine-4-yl.

42. The method according to claim 37, wherein the mammal is a human.

\* \* \* \* \*